(12) United States Patent
Jacques et al.

(10) Patent No.: US 10,358,477 B2
(45) Date of Patent: Jul. 23, 2019

(54) IL-15RALPHA SUSHI DOMAIN—IL-15 FUSION PROTEINS

(75) Inventors: Yannick Jacques, Nantes (FR); Ariane Plet, Nantes (FR); Erwan Mortier, Nantes (FR); Agnes Quemener, Nantes (FR); Patricia Vusio, Saint Sebastien sur Loire (FR)

(73) Assignee: INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 1501 days.

(21) Appl. No.: 12/090,930

(22) PCT Filed: Oct. 6, 2006

(86) PCT No.: PCT/IB2006/003917
§ 371 (c)(1),
(2), (4) Date: Aug. 6, 2008

(87) PCT Pub. No.: WO2007/046006
PCT Pub. Date: Apr. 26, 2007

(65) Prior Publication Data
US 2009/0238791 A1 Sep. 24, 2009

(30) Foreign Application Priority Data
Oct. 20, 2005 (EP) .................... 05292210

(51) Int. Cl.
*C07K 14/715* (2006.01)
*C07K 14/54* (2006.01)

(52) U.S. Cl.
CPC ...... *C07K 14/7155* (2013.01); *C07K 14/5443* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,011,912 A | 4/1991 | Hopp et al. | |
| 5,073,627 A * | 12/1991 | Curtis et al. ................. | 530/351 |
| 5,108,910 A | 4/1992 | Curtis et al. | |
| 6,787,132 B1 | 9/2004 | Gabizon et al. | |
| 7,112,436 B1 | 9/2006 | Rose-John | |
| 7,198,781 B1 | 4/2007 | Revel et al. | |
| 8,124,084 B2 * | 2/2012 | Lefrancois et al. ....... | 424/134.1 |
| 2006/0263857 A1 * | 11/2006 | Lefrancois et al. ....... | 435/69.52 |

FOREIGN PATENT DOCUMENTS

| | | |
|---|---|---|
| EP | 971728 B1 | 12/2002 |
| EP | 811065 B1 | 9/2006 |
| JP | 2001-509371 | 7/2001 |
| WO | 95/27722 A1 | 4/1995 |
| WO | 95/30695 A2 | 11/1995 |
| WO | 9741232 | 11/1997 |
| WO | 99/02552 A2 | 1/1999 |
| WO | 0222805 | 3/2002 |
| WO | 2004035622 A2 | 4/2004 |
| WO | 2005/085282 A1 | 9/2005 |
| WO | 2005085282 | 9/2005 |
| WO | 2007001677 | 1/2007 |
| WO | 2007/084342 A2 | 7/2007 |
| WO | 2007/095643 A2 | 8/2007 |

OTHER PUBLICATIONS

Dubois et al. Natural splicing of exon 2 of human interleukin-15 receptor alpha-chain mRNA results in a shortened form with a distinct pattern of expression. J Biol Chem. Sep. 17, 1999; 274(38): 26978-84.*
Giron-Michel Julien et al., "Membrane-bound and soluble IL-15/IL-15Ralpha complexes display differential signaling and functions on human hematopoietic progenitors", Blood, Oct. 1, 2005, vol. 106, No. 7, pp. 2302-2310, XP002394327.
Matsumoto Mitsuhiro et al., "On-column refolding and characterization of soluble human interleukin-15 receptor alpha-chain produced in *Escherichia coli*", Protein Expression and Purification, Sep. 2003, vol. 31, No. 1, pp. 64-71, XP002394328.
Wei Xq et al., "The sushi domain of soluble IL-15 receptor alpha is essential for binding IL-15 and inhibiting inflammatory and allogenic responses in vitro and in vivo", Journal of Immunology, Jul. 1, 2001, vol. 167, No. 1, pp. 277-282, XP002394329.
Ruchatz H et al., "Soluble IL-15 receptor alpha-chain administration prevents murine collagen-induced arthritis: a role for IL-15 in development of antigen-induced immunopathology", Journal of Immunology, 1998, vol. 160, pp. 5654-5660, XP002941876.
Molter Erwan et al., "Soluble interleukin-15 receptor alpha (IL-15Ralpha)-sushi as a selective and potent agonist of IL-15 action through IL-15R beta/gamma. Hyperagonist IL-15 x IL-15R alph fusion proteins", The Jurnal of Biological Chemistry, Jan. 20, 2006, vol. 281, No. 3, pp. 1612-1619, XP002394330.
International Search Report of PCT/IB2006/003917 filed Oct. 6, 2006.
Pflanz, S., et al. (1999). "A fusion protein of interleukin-11 and soluble interleukin-11 receptor acts as a superagonist on cells expressing gp130." FEBS Lett 450(1-2): 117-122.
Quemener, A., et al. (2006). "Docking of human interleukin-15 to its specific receptor alpha chain: correlation between molecular modeling and mutagenesis experimental data." Proteins 65(3): 623-636.

(Continued)

*Primary Examiner* — Dong Jiang
(74) *Attorney, Agent, or Firm* — Kagan Binder, PLLC

(57) ABSTRACT

The present invention relates to the stimulation of the IL-15Rbeta/gamma signalling pathway, to thereby induce and/or stimulate the activation and/or proliferation of IL-15Rbeta/gamma-positive cells, such as NK and/or T cells. Appropriate compounds include compounds comprising at least one IL-15Rbeta/gamma binding entity, directly or indirectly linked by covalence to at least one polypeptide which contains the sushi domain of the extracellular region of an IL-15Ralpha.

10 Claims, 42 Drawing Sheets
Specification includes a Sequence Listing.

(56) References Cited

OTHER PUBLICATIONS

Bamborough, P., et al. (1994). "The interleukin-2 and interleukin-4 receptors studied by molecular modelling." Structure 2(9): 839-851.
Bernard, J., et al. (2004). "Identification of an interleukin-15alpha receptor-binding site on human interleukin-15." J Biol Chem 279(23): 24313-24322.
Grabstein, K. H., et al. (1994). "Cloning of a T cell growth factor that interacts with the beta chain of the interleukin-2 receptor." Science 264(5161): 965-968.
Giri, J. G., et al. (1994). "Utilization of the beta and gamma chains of the IL-2 receptor by the novel cytokine IL-15." EMBO J 13(12): 2822-2830.
Anderson, D. M., et al. (1995). "Functional characterization of the human interleukin-15 receptor alpha chain and close linkage of IL15RA and IL2RA genes." J Biol Chem 270(50): 29862-29869.
Burton, J. D., et al. (1994). "A lymphokine, provisionally designated interleukin T and produced by a human adult T-cell leukemia line, stimulates T-cell proliferation and the induction of lymphokine-activated killer cells." Proc Natl Acad Sci U S A 91(11): 4935-4939.
Carson, W. E., et al. (1994). "Interleukin (IL) 15 is a novel cytokine that activates human natural killer cells via components of the IL-2 receptor." J Exp Med 180(4): 1395-1403.
Wilkinson, P. C. and F. Y. Liew (1995). "Chemoattraction of human blood T lymphocytes by interleukin-15." J Exp Med 181(3): 1255-1259.
Kennedy, M. K., et al. (2000). "Reversible defects in natural killer and memory CD8 T cell lineages in interleukin 15-deficient mice." J Exp Med 191(5): 771-780.
Lodolce, J. P., et al. (2001). "T cell-independent interleukin 15Ralpha signals are required for bystander proliferation." J Exp Med 194(8): 1187-1194.
Marks-Konczalik, J., et al. (2000). "IL-2-induced activation-induced cell death is inhibited in IL-15 transgenic mice." Proc Natl Acad Sci U S A 97(21): 11445-11450.
Ku, C. C., et al. (2000). "Control of homeostasis of CD8+ memory T cells by opposing cytokines." Science 288(5466): 675-678.
Li, X. C., et al. (2001). "IL-15 and IL-2: a matter of life and death for T cells in vivo." Nat Med 7(1): 114-118.
Dubois, S., et al. (2002). "IL-15Ralpha recycles and presents IL-15 in trans to neighboring cells." Immunity 17(5): 537-547.
Burkett, P. R., et al. (2003). "IL-15Rα expression on CD8+ T cells is dispensable for T cell memory." Proc Natl Acad Sci U S A 100(8): 4724-4729.
Schluns, K. S., et al. (2004). "Distinct cell types control lymphoid subset development by means of IL-15 and IL-15 receptor alpha expression." Proc Natl Acad Sci U S A 101(15): 5616-5621.
Kobayashi, H., et al. (2005). "Role of trans-cellular IL-15 presentation in the activation of NK cell-mediated killing, which leads to enhanced tumor immunosurveillance." Blood 105(2): 721-727.
Norman, D. G., et al. (1991). "Three-dimensional structure of a complement control protein module in solution." J Mol Biol 219(4): 717-725.
Schulz, O., et al. (1998). "Proteolytic cleavage of CD25, the alpha subunit of the human T cell interleukin 2 receptor, by Der p 1, a major mite allergen with cysteine protease activity." J Exp Med 187(2): 271-275.
Sheu, B. C., et al. (2001). "A novel role of metalloproteinase in cancer-mediated immunosuppression." Cancer Res 61(1): 237-242.
Mortier, E., et al. (2004). "Natural, proteolytic release of a soluble form of human IL-15 receptor alpha-chain that behaves as a specific, high affinity IL-15 antagonist." J Immunol 173(3): 1681-1688.
Smith, X. G., et al. (2000). "Selective blockade of IL-15 by soluble IL-15 receptor alpha-chain enhances cardiac allograft survival." J Immunol 165(6): 3444-3450.
Farner, N. L., et al. (1997). "Alteration of the CD34+ Tf-1 beta cell line profile in response to long-term exposure to IL-15." Cytokine 9(5): 316-327.

Meissner, U., et al. (2001). "A soluble form of the murine common gamma chain is present at high concentrations in vivo and suppresses cytokine signaling." Blood 97(1): 183-191.
Jones, S. A. and S. Rose-John (2002). "The role of soluble receptors in cytokine biology: the agonistic properties of the sIL-6R/IL-6 complex." Biochim Biophys Acta 1592(3): 251-263.
Heaney, M. L. and D. W. Golde (1998). "Soluble receptors in human disease." J Leukoc Biol 64(2): 135-146.
Rose-John, S. and P. C. Heinrich (1994). "Soluble receptors for cytokines and growth factors: generation and biological function." Biochem J 300 ( Pt 2): 281-290.
Davis, S., et al. (1993). "Released form of CNTF receptor alpha component as a soluble mediator of CNTF responses." Science 259(5102): 1736-1739.
Karow, J., et al. (1996). "Mediation of interleukin-11-dependent biological responses by a soluble form of the interleukin-11 receptor." Biochem J 318 ( Pt 2): 489-495.
Elson, G. C., et al. (2000). "CLF associates with CLC to form a functional heteromeric ligand for the CNTF receptor complex." Nat Neurosci 3(9): 867-872.
Sandau, M. M., et al. (2004). "Cutting edge: transpresentation of IL-15 by bone marrow-derived cells necessitates expression of IL-15 and IL-15R alpha by the same cells." J Immunol 173(11): 6537-6541.
Koka R., et al. (2003). "Interleukin (IL)-15R□-deficient natural killer cells survive in normal but not IL-15R□-deficient mice." J Exp Med 197(8): 977-984.
Bulanova, E., et al. (2003). "Mast cells express novel functional IL-15 receptor alpha isoforms." J Immunol 170(10): 5045-5055.
Fischer, M., et al. (1997). "I. A bioactive designer cytokine for human hematopoietic progenitor cell expansion." Nat Biotechnol 15(2): 142-145.
Hopp, T. P., et al. (1988). "A short polypeptide marker sequence useful for recombinant protein identification and purification." Biotechnology 6(10): 1204-1210.
Andersson, L., et al. (2000). "Large-scale synthesis of peptides." Biopolymers 55(3): 227-250.
Lehours, P., et al. (2000). "Subunit structure of the high and low affinity human interleukin-15 receptors." Eur Cytokine Netw 11(2): 207-215.
Fernandez-Botran, R. (1991). "Soluble cytokine receptors: their role in immunoregulation." FASEB J 5(11): 2567-2574.
Burkett, P. R., et al. (2004). "Coordinate expression and trans presentation of interleukin (IL)-15R□ and IL-15 supports natural killer cell and memory CD8+ T cell homeostasis." J Exp Med 200(7): 825-834.
Pettit, D. K., et al. (1997). "Structure-function studies of interleukin 15 using site-specific mutagenesis, polyethylene glycol conjugation, and homology modeling." J Biol Chem 272(4): 2312-2318.
Forcina, G., et al. (2004). "Interleukin-15 modulates interferon-gamma and beta-chemokine production in patients with HIV infection: implications for immune-based therapy." Cytokine 25(6): 283-290.
Scheller, J. and S. Rose-John (2006). "Interleukin-6 and its receptor: from bench to bedside." Med Microbiol Immunol 195(4): 173-183.
R&D Systems, I. (2012). Recombinant Mouse IL-15 R□ Fc Chimera. I. R&D Systems. Minneapolis, Minn.
Bouchaud, G., et al. (2008). "The exon-3-encoded domain of IL-15ralpha contributes to IL-15 high-affinity binding and is crucial for the IL-15 antagonistic effect of soluble IL-15Ralpha." J Mol Biol 382(1): 1-12.
Dubois, S., et al. (2008). "Preassociation of IL-15 with IL-15R alpha-IgG1-Fc enhances its activity on proliferation of NK and CD8+/CD44high T cells and its antitumor action." J Immunol 180(4): 2099-2106.
Budagian, V., et al. (2004). "Natural soluble interleukin-15Ra is generated by cleavage that involves the tumor necrosis factor-a-converting enzyme (TACE/ADAM17)." J Biol Chem 279(39): 40368-40375.
Rubinstein, M. P., et al. (2006). "Converting IL-15 to a superagonist by binding to soluble IL-15R□." Proc Natl Acad Sci U S A 103(24): 9166-9171.

(56) References Cited

OTHER PUBLICATIONS

Kanakura, Y., et al. (1993). "Functional expression of interleukin 2 receptor in a human factor-dependent megakaryoblastic leukemia cell line: evidence that granulocyte-macrophage colony-stimulating factor inhibits interleukin 2 binding to its receptor." Cancer Res 53(3): 675-680.
Carson, W. and M. A. Caligiuri (1998). "Interleukin-15 as a potential regulator of the innate immune response." Braz J Med Biol Res 31(1): 1-9.
Bamford, R. N., et al. (1994). "The interleukin (IL) 2 receptor beta chain is shared by IL-2 and a cytokine, provisionally designated IL-T, that stimulates T-cell proliferation and the induction of lymphokine-activated killer cells." Proc Natl Acad Sci U S A 91(11): 4940-4944.
Avanzi, G. C., et al. (1988). "Selective growth response to IL-3 of a human leukaemic cell line with megakaryoblastic features." Br J Haematol 69(3): 359-366.
R&D Systems, I. (2016). Human IL-2 RB Antibody. I. R&D Systems. Minneapolis, Minn.,: 1.
R&D Systems, I. (2016). Human IL-15 Antibody. I. R&D Systems. Minneapolis, Minn.,: 1.
Nakamura, Y., et al. (1994). "Heterodimerization of the IL-2 receptor beta- and gamma-chain cytoplasmic domains is required for signalling." Nature 369(6478): 330-333.
Hammerstrom, A. E., et al. (2011). "Cancer immunotherapy: sipuleucel-T and beyond." Pharmacotherapy 31(8): 813-828.
Gerritsen, W. R. (2012). "The evolving role of immunotherapy in prostate cancer." Ann Oncol 23 Suppl 8: viii22-27.
Dudley, M. E. and S. A. Rosenberg (2003). "Adoptive-cell-transfer therapy for the treatment of patients with cancer." Nat Rev Cancer 3(9): 666-675.
Ruggeri, L., et al. (2002). "Effectiveness of donor natural killer cell alloreactivity in mismatched hematopoietic transplants." Science 295(5562): 2097-2100.
de Gast, G. C., et al. (2000). "Phase I trial of combined immunotherapy with subcutaneous granulocyte macrophage colony-stimulating factor, low-dose interleukin 2, and interferon alpha in progressive metastatic melanoma and renal cell carcinoma." Clin Cancer Res 6(4): 1267-1272.
Margolin, K. A. (2000). "Interleukin-2 in the treatment of renal cancer." Semin Oncol 27(2): 194-201.
Meazza, R., et al. (2011). "Role of common-gamma chain cytokines in NK cell development and function: perspectives for immunotherapy." J Biomed Biotechnol 2011: 861920.
Rosenberg, S. A., et al. (1994). "Treatment of patients with metastatic melanoma with autologous tumor-infiltrating lymphocytes and interleukin 2." J Natl Cancer Inst 86(15): 1159-1166.
Eklund, J. W. and T. M. Kuzel (2004). "A review of recent findings involving interleukin-2-based cancer therapy." Curr Opin Oncol 16(6): 542-546.
Guo, H. and X. Qian (2010). "Clinical applications of adoptive natural killer cell immunotherapy for cancer: current status and future prospects." Onkologie 33(7): 389-395.
Hallett, W. H. and W. J. Murphy (2004). "Natural killer cells: biology and clinical use in cancer therapy." Cell Mol Immunol 1(1): 12-21.
Plautz, G. E., et al. (2003). "Considerations on clinical use of T cell immunotherapy for cancer." Arch Immunol Ther Exp (Warsz) 51(4): 245-257.
Huntington, N. D., et al. (2009). "IL-15 trans-presentation promotes human NK cell development and differentiation in vivo." J Exp Med 206(1): 25-34.
Huntington, N. D., et al. (2011). "IL-15 transpresentation promotes both human T-cell reconstitution and T-cell-dependent antibody responses in vivo." Proc Natl Acad Sci U S A 108(15): 6217-6222.
Bessard, A., et al. (2009). "High antitumor activity of RLI, an interleukin-15 (IL-15)-IL-15 receptor alpha fusion protein, in metastatic melanoma and colorectal cancer." Mol Cancer Ther 8(9): 2736-2745.
Schluns, K. S., et al. (2005). "The roles of interleukin-15 receptor alpha: trans-presentation, receptor component, or both?" Int J Biochem Cell Biol 37(8): 1567-1571.
Van Belle, T. and J. Grooten (2005). "IL-15 and IL-15Ralpha in CD4+T cell immunity." Arch Immunol Ther Exp (Warsz) 53(2): 115-126.
Ferrari-Lacraz, S., et al. (2004). "Targeting IL-15 receptor-bearing cells with an antagonist mutant IL-15/Fc protein prevents disease development and progression in murine collagen-induced arthritis." J Immunol 173(9): 5818-5826.
Oh, S., et al. (2004). "IL-15/IL-15Ralpha-mediated avidity maturation of memory CD8+ T cells." Proc Natl Acad Sci U S A 101(42): 15154-15159.
Neely, G. G., et al. (2004). "Monocyte surface-bound IL-15 can function as an activating receptor and participate in reverse signaling." J Immunol 172(7): 4225-4234.
Rose, T., et al. (2003). "Structural analysis and modeling of a synthetic interleukin-2 mimetic and its interleukin-2Rbeta2 receptor." J Biol Chem 278(25): 22868-22876.
Schluns, K. S., et al. (2002). "Cutting edge: requirement for IL-15 in the generation of primary and memory antigen-specific CD8 T cells." J Immunol 168(10): 4827-4831.
Liu, K., et al. (2002). "IL-15 mimics T cell receptor crosslinking in the induction of cellular proliferation, gene expression, and cytotoxicity in CD8+ memory T cells." Proc Natl Acad Sci U S A 99(9): 6192-6197.
Olosz, F. and T. R. Malek (2002). "Structural basis for binding multiple ligands by the common cytokine receptor gamma-chain." J Biol Chem 277(14): 12047-12052.
Waldmann, T. A. (2002). "The IL-2/IL-15 receptor systems: targets for immunotherapy." J Clin Immunol 22(2): 51-56.
Ferrari-Lacraz, S., et al. (2001). "An antagonist IL-15/Fc protein prevents costimulation blockade-resistant rejection." J Immunol 167(6): 3478-3485.
Pereno, R., et al. (1999). "IL-15/IL-15R alpha intracellular trafficking in human cells and protection from apoptosis." Ann N Y Acad Sci 876: 236-245.
Prinz, M., et al. (1998). "Alternative splicing of mouse IL-15 is due to the use of an internal splice site in exon 5." Brain Res Mol Brain Res 63(1): 155-162.
Lodolce, J. P., et al. (1998). "IL-15 receptor maintains lymphoid homeostasis by supporting lymphocyte homing and proliferation." Immunity 9(5): 669-676.
Waldmann, T., et al. (1998). "Interleukin-2, interleukin-15, and their receptors." Int Rev Immunol 16(3-4): 205-226.
Ohteki, T., et al. (1997). "Role for IL-15/IL-15 receptor beta-chain in natural killer 1.1+ T cell receptor-alpha beta+ cell development" J Immunol 159(12): 5931-5935.
DiSanto, J. P. (1997). "Cytokines: shared receptors, distinct functions." Curr Biol 7(7): R424-426.
Kennedy, M. K. and L. S. Park (1996). "Characterization of interleukin-15 (IL-15) and the IL-15 receptor complex." J Clin Immunol 16(3): 134-143.
Cosman, D., et al. (1995). "Interleukin 15 and its receptor." Ciba Found Symp 195: 221-229; discussion 229-231.
Stoklasek, T. A., et al. (2006). "Combined IL-15/IL-15Ralpha immunotherapy maximizes IL-15 activity in vivo." J Immunol 177(9): 6072-6080.
Lorenzen, I., et al. (2006). "The structure of the interleukin-15 alpha receptor and its implications for ligand binding." J Biol Chem 281(10): 6642-6647.
Giri, et al. (1995) "Identification and cloning of a novel IL-15 binding protein that is structurally related to the a chain of the IL-2 receptor", The EMBO Journal, 14(15), pp. 3654-3663.

\* cited by examiner

Human interleukin-15 receptor alpha chain precursor (IL15Ralpha) mRNA,
complete cds (1610 bp)
ACCESSION NUMBER U31628 (VERSION U31628.1 GI:1125055)

```
   1 cccagagcag cgctcgccac ctcccccccgg cctgggcagc gctcgcccgg ggagtccagc
  61 ggtgtcctgt ggagctgccg ccatggcccc gcggcgggcg cgggctgccc ggaccctcgg
 121 tctcccgccg ctgctactgc tgctgctgct cggccgcccg gcgacgcggg gcatcacgtg
 181 ccctcccccc atgtccgtgg aacacgcaga catctggtc aagagctaca gcttgtactc
 241 cagggagcgg tacattgta actctggttt caagcgtaaa gccggcacgt ccagcctgac
 301 ggagtgcgtg ttgaacaagg ccacgaatgt cgcccactgg acaaccccca gtctcaaatg
 361 cattagagac ctgcccctgg ttcaccaaag gccagcgcca cctcacacag taacgacggc
 421 agggtgacc ccacagccaa agagcctctc ccctctgga aaagagcccg cagcttcatc
 481 tccagctca aacaacacag cggccacaca agcagtatt gtcccgggct cctcccacg
 541 gccttcaaaa tcaccttcca caggaaccac agagataagc agtcatgagt gcatccgcct
 601 cacccccctct cagacaacag ccaagaactg gaactcaca caccactgtg gctatctcca cgtccactgt
 661 gccagtgtg tatccacagg gccacagcga ctgtgtctct cctgcatgc tacctcaagt caaggcaaac
 721 cctgctgtgt gggctgagcg ctgtgtctct cctgcatgc tacctcaagt caaggcaaac
 781 tcccccgctg gccagcgttg aaatggaagc catgaggct ctgccggtga ctgcctggac
 841 cagcagcaga gatgaagact tggaaaactg ctctcaccac ctatgaaact cgggaaacc
 901 agcccagcta agtccggagt gaaggagcct ctctgcttta gctaaagacg actgagaaga
 961 ggtgcaagga agcgggctcc aggagcaagc tcaccaggcc tctcagaagt cccagcagga
1021 tctcacgac tgccgggtcg gcgcctcctg cgcgagggag caggttctcc gcattcccat
1081 gggcaccacc tgcctgcctg tcgtgcttg gacccagggc ccagcttccc aggagagacc
1141 aaaggcttct gagcaggatt tttatttcat tacagtgtga gctgcctgga atacatgtgg
1201 taatgaaata aaaaccctgc ccgaatcttt ccgtcccctca tcctaacttg cagttcacag
1261 agaaaagtga catacccaaa gctctctgtc aattacaagg cttctcctgg cgtgggagac
1321 gtctacaggg aagacaccag cgtttgggct tctaaccacc ctgtctccag ctgtctgca
1381 cacatggaca gggacctggg aaggtggga gagatgctga gccagcgaa tcctctccat
1441 tgaaggattc aggaagaaga aactcaact cagtgccatt ttacgaatat atgcgtttat
1501 atttatactt cctgtctat tatatctata cattatatat tatttgtatt ttgacattgt
1561 acctttgtata aacaaaataa aacatctatt ttcaatattt ttaaaatgca
```

SEQ ID NO:1

FIGURE 8

83..883 of IL15-Ralpha SEQ ID NO:1 = CDS =

```
 83         atggcccc gcggcgggcg cgcggctgcc ggaccctcgg
121 tctcccgcg ctgctactgc tgctgctgct ccggcgcccg gcgacgcggg gcatcacgtg
181 ccctcccccc atgtccgtgg aacacgcaga catctgggtc aagagctaca gcttgtactc
241 cagggagcgg tacatttgta actctggttt caagcgtaaa gccggcacgt ccagcctgac
301 ggagtgcgtg tacatttgta ccacgaatgt cgcccactgg acaaccccca gtctcaaatg
361 cattagagac cctgccctgg ttcaccaaag gccagcgcca cccttccacag taacgacggc
421 aggggtgacc ccacagccag agagcctctc cccttctgga aaagagcccg cagcttcatc
481 tccagctca aacaacacag cggccacaac agcagctatt gtcccgggct cccagctgat
541 gcctcaaaa tcacccttcca caggaaccac agagataagc agtcatgagt cctccacacgg
601 cacccctct cagacaacag ccaagaactg ggaactcaca gcatccgcct cccaccagcc
661 gccaggtgtg tatccacagg gccagcgca caccactgtg gctatctcca cgtccactgt
721 cctgctgtgt gggctgagcg ctgtctct ctggcatgc taacctcaagt caaggcaaac
781 tccccgctg gccagcgttg aatgaagct catggaggct ctgccgtga cttgggggac
841 cagcagcaga gatgaagact tggaaaactg ctctcaccac cta         SEQ ID NO:2
```

Human interleukin-15 receptor alpha chain (267 aa)
ACCESSION NUMBER AAC50312 (VERSION AAC50312.1 GI:1125056)

```
  1 maprrargcr tlglpalll lllrppatrg itcpppmsve hadiwvksys lysreryicn
 61 sgfkrkagts sltecvlnka tnvahwttps lkcirdpalv hqrpappstv ttagvtpqpe
121 slspsgkepa asspssnnta attaaivpgs qlmpskspst gtteisshes shgtpsqtta
181 knweltasas hqppgvypqg hsdttvaist stvllcglsa vsllacylks rqtpplasve
241 meamealpvt wgtssrdedl encshhl                           SEQ ID NO:3
```

FIGURE 9

83..172 of IL-15Ralpha SEQ ID NO:1 = CDS of sig_peptide =

```
 83                      atggcccc gcggcgggcg cgcggctgcc ggaccctcgg
121 tctcccggcg ctgctactgc tgctgctgct ccggccgccg gcgacgcggg gc
                                                        SEQ ID NO:4
```

1..30 of IL15-Ralpha protein SEQ ID NO:3 = sig_peptide =
                                                        SEQ ID NO:5
```
  1 maprrargcr tlglpalll lllrppatrg
```

173..883 of IL15-Ralpha SEQ ID NO:1 = CDS of mat_peptide =

```
173                                                              atcacgtg
181 cctcccccc atgtccgtgg aacacgaga catctgggtc aagagctaca gcttgtactc
241 cagggagcgg tacatttgta actctggttt caagcgtaaa gccggcacgt ccagcctgac
301 ggagtgcgtg ttgaacaagg ccacgaatgt cgcccactgg acaacccca gtctcaaatg
361 cattagagac cctgccctgg ttcaccaaag gccagagcca cccttccaca gccttcatc
421 agggtgacc ccacagccag agagcctctc cccttctga aaagagcccg cagctccatc
481 tcccagctca aacaacacag cggccacaac agcagctatt gtcccgggct cccagctgat
541 gcctttcaaaa tcaccttcca caggaaccac agagataagc agtcatgagt cctcccacgg
601 cacccctct cagacaacag ccaagaactg ggaactcaca gcatccgcct ccacccagcc
661 gccaggtgtg tatccacagg gccacagcga caccactgtg gctatctcca cgtccactgt
721 cctgctgtgt gggctgagcg ctgtctct ctgcatgc tacctcaagt caagcaaaac
781 tcccccgctg gccagcgttg aaatggaagc catggaggct ctgccggtga cttggggac
841 cagcagcaga gatgaagact ggaaaactg ctctcaccac cta
                                                        SEQ ID NO:6
```

31..267 of IL15-Ralpha protein SEQ ID NO:3 = mat_peptide =
```
 31                                itcpppmsve hadiwvksys lysreryicn
 61 sgfkrkagts sltecvlnka tnvahwttps lkcirdpalv hqrpappstv ttagvtpqpe
121 slspsgkepa asspssnnta attaaivpgs qlmpskspst gtteisshes shgtpsqtta
181 knweltasas hqppgvypqg hsdttvaist stvllcglsa vsllacylks rqtpplasve
241 meamealpvt wgtssrdedl encshhl
                                                        SEQ ID NO:7
```

FIGURE 10

1..170 of IL15-Ralpha SEQ ID NO:1 = exon 1 of human IL15-Ralpha =

```
  1 cccagagcag cgctcgccac ctcccccgg cctggcag gctcgcccg ggagtccagc
 61 ggtgtcctgt ggagctgccg ccatggccgc ccctcgccc gcggcggggcg ccgggctgcc ggaccctcgg
121 tctcccggcg ctgctactgc tgctgctgct ccggccgcgc gcgacgcggg
                                                              SEQ ID NO:8
```

171..365 of IL15-Ralpha SEQ ID NO:1 = exon 2 of human IL15-Ralpha =
gcatcacgtg

```
171
181 ccctccccc atgtccgtgg aacacgcaga catctgggtc aagagctaca gcttgtactc
241 cagggagcgg tacattgta actctgttt caagcgtaaa gccggcacgt ccagcctgac
301 ggagtgcgtg ttgaacaagg ccacgaatgt cgccactgg acaaccccca gtctcaaatg
361 catta                                                      SEQ ID NO:9
```

366..464 of IL15-Ralpha SEQ ID NO:1 = exon 3 of human IL15R-alpha
```
366      gagac cctgccctgg ttcaccaaag gccagcgcca cctccacag taacgacggc
421 agggtgacc ccacagccaa agagccctc cccttctgga aaag
                                                              SEQ ID NO:10
```

465..665 of IL15-Ralpha SEQ ID NO:1 = exon 4 of human IL15R-alpha =
agcccg cagcttcatc

```
465
481 tccagctca aacaacacag cggccacaac agcagctatt gtcccgggct ccagctgat
541 gcctttcaaaa tcaccttcca caggaaccac agagataagc agtcatgagt cctcccacg
601 cacccctct cagacaacag ccaagaactg ggaactcaca gcatccgcct cccaccagcc
661 gccag                                                      SEQ ID NO:11
```

666..698 of IL15-Ralpha SEQ ID NO:1 = exon 5 of human IL15R-alpha =
```
666 gtgtg tatccacagg gccacagcga caccactg
                                                              SEQ ID NO:12
```

FIGURE 11

179..361 of human IL-15Ralpha SEQ ID NO:1 =
sequence coding for the human IL-15Ralpha sushi domain =

```
179                                                                          tg
181 ccctcccccc atgtccgtgg aacacgcaga catctgggtc aagagctaca gcttgtactc
241 cagggagcgg tacatttgta actctggttt caagcgtaaa gccggcacgt ccagcctgac
301 ggagtgcgtg ttgaacaagg ccacgaatgt cgcccactgg acaaccccca gtctcaaatg
361 c
                                                                  SEQ ID NO:13
```

33..93 of human IL-15Ralpha protein SEQ ID NO:3 =
human IL-15Ralpha sushi domain =

```
33           cpppmsve hadiwvksys lysreryicn
61  sgfkrkagts sltecvlnka tnvahwttps lkc
                                                                  SEQ ID NO:14
```

173..361 of human IL-15Ralpha SEQ ID NO:1 =
sequence coding for (it + the human IL-15Ralpha sushi domain) =

```
173                                                                    atcacgtg
181 ccctcccccc atgtccgtgg aacacgcaga catctgggtc aagagctaca gcttgtactc
241 cagggagcgg tacatttgta actctggttt caagcgtaaa gccggcacgt ccagcctgac
301 ggagtgcgtg ttgaacaagg ccacgaatgt cgcccactgg acaaccccca gtctcaaatg
361 c
                                                                  SEQ ID NO:15
```

31..93 of human IL-15Ralpha protein SEQ ID NO:3 =
it + human IL-15Ralpha sushi domain =

```
31         itcpppmsve hadiwvksys lysreryicn
61 sgfkrkagts sltecvlnka tnvahwttps lkc
                                                                  SEQ ID NO:16
```

FIGURE 12

176..361 of human IL-15Ralpha SEQ ID NO:1 =
sequence coding for (t + the human IL-15Ralpha sushi domain) =

```
176                                                                acgtg
181 ccctcccccc atgtccgtgg aacacgcaga catctgggtc aagagctaca gcttgtactc
241 cagggagcgg tacatttgta actctgtttt caagcgtaaa gccggcacgt ccagcctgac
301 ggagtgcgtg ttgaacaagg ccacgaatgt cgcccactgg acaaccccca gtctcaaatg
361 c                                                        SEQ ID NO: 17
```

32..93 of human IL-15Ralpha protein SEQ ID NO:3 =
t + human IL-15Ralpha sushi domain =

```
32                                 tcpppmsve hadiwvksys lysreryicn
61 sgfkrkagts sltecvlnka tnvahwttps lkc                    SEQ ID NO: 18
```

FIGURE 13

362..403 of human IL-15Ralpha SEQ ID NO:1 =
sequence coding for the hinge region of human IL15-Ralpha =                    SEQ ID NO: 19
362 attagagac cctgccctgg ttcaccaaag gccagcgcca ccc 94..107 of human IL-15Ralpha SEQ ID NO:3 =
hinge region of human IL15-Ralpha =                                             SEQ ID NO: 20

94 irdpalvhqrp app

362..370 of human IL-15Ralpha SEQ ID NO:1 =
sequence coding for a fragment of the hinge region of human IL15-Ralpha =
362 attagagac 94..96 of human IL-15Ralpha SEQ ID NO:3 =
fragment of the hinge region of human IL15-Ralpha =

94 ird

362..364 of human IL-15Ralpha SEQ ID NO:1 =
sequence coding for a fragment of the hinge region of human IL15-Ralpha =
362 att 94..94 of human IL-15Ralpha SEQ ID NO:3 =
fragment of the hinge region of human IL15-Ralpha =

179..364 of human IL-15Ralpha SEQ ID NO:1 =
sequence coding for (the human IL-15Ralpha sushi domain + i) =

179                                                                                    tg
181 ccctccccccc atgtccgtgg aacacgcaga catctgggtc aagagctaca gcttgtactc
241 cagggagcgg tacatttgta actctgtttt caagcgtaaa gccggcacgt ccagcctgac
301 ggagtgcgtg ttgaacaagg ccacgaatgt cgcccactgg acaaccccca gtctcaaatg
364 catt

SEQ ID NO: 21

33..94 of human IL-15Ralpha protein SEQ ID NO:3 =
human IL-15Ralpha sushi domain + i =

33                                  cppppmsve hadiwvksys lysreryicn
61 sgfkrkagts sltecvlnka tnvahwttps lkci

SEQ ID NO: 22

173..364 of human IL-15Ralpha SEQ ID NO:1 =
sequence coding for (it + the human IL-15Ralpha sushi domain + i) =

173                                                               atcacgtg
181 ccctccccccc atgtccgtgg aacacgcaga catctgggtc aagagctaca gcttgtactc
241 cagggagcgg tacatttgta actctgtttt caagcgtaaa gccggcacgt ccagcctgac
301 ggagtgcgtg ttgaacaagg ccacgaatgt cgcccactgg acaaccccca gtctcaaatg
361 catt

SEQ ID NO: 23

31..94 of human IL-15Ralpha protein SEQ ID NO:3 =
it + human IL-15Ralpha sushi domain + i =

31                                itcpppmsve hadiwvksys lysreryicn
61 sgfkrkagts sltecvlnka tnvahwttps lkci

SEQ ID NO: 24

FIGURE 15

176..364 of human IL-15Ralpha SEQ ID NO:1 =
sequence coding for (t + the human IL-15Ralpha sushi domain + i) =

```
176                                                                    acgtg
181 ccctccccc atgtccgtgg aacacgcaga catctgggtc aagagctaca gcttgtactc
241 cagggagcgg tacatttgta actctgtttt caagcgtaaa gccggcacgt ccagcctgac
301 ggagtgcgtg ttgaacaagg ccacgaatgt cgcccactgg acaaccccca gtctcaaatg
361 catt
                                                              SEQ ID NO: 25
```

32..94 of human IL-15Ralpha protein SEQ ID NO:3 =
t + human IL-15Ralpha sushi domain + i =

```
33                             tcpppmsve hadiwvksys lysreryicn
61 sgfkrkagts sltecvlnka tnvahwttps lkci
                                                            SEQ ID NO: 26
```

173..370 of human IL-15Ralpha SEQ ID NO:1 =
sequence coding for (it + human IL-15Ralpha sushi domain + ird) =

```
173                                                                  atcacgtg
181 ccctccccc atgtccgtgg aacacgcaga catctgggtc aagagctaca gcttgtactc
241 cagggagcgg tacatttgta actctgtttt caagcgtaaa gccggcacgt ccagcctgac
301 ggagtgcgtg ttgaacaagg ccacgaatgt cgcccactgg acaaccccca gtctcaaatg
361 cattagagac
                                                              SEQ ID NO :27
```

31..96 of human IL-15Ralpha protein SEQ ID NO:3 =
it + human IL-15Ralpha sushi domain + ird =

```
31                          itcpppmsve hadiwvksys lysreryicn
61 sgfkrkagts sltecvlnka tnvahwttps lkcird
                                                            SEQ ID NO:28
```

FIGURE 16

173..403 of human IL-15Ralpha SEQ ID NO:1 =
sequence coding for (it + human IL-15Ralpha sushi domain + hinge region) =
173                                                                      atcacgtg
181 ccctcccccc atgtccgtgg aacacgcaga catctgggtc aagagctaca gcttgtactc
241 cagggagcgg tacatttgta actctgttt caagcgtaaa gccggcacgt ccagcctgac
301 ggagtgcgtg ttgaacaagg ccacgaatgt cgccactgg acaacccca gtctcaaatg
361 cattgagacc cctgccctgg ttcaccaaag gccagcgcca ccc          SEQ ID NO:29

31..107 of human IL-15Ralpha protein SEQ ID NO :3 =
it + human IL-15Ralpha sushi domain + hinge region =
        itcpppmsve hadiwvksys lysreryicn
31
61 sgfkrkagts sltecvlnka tnvahwttps lkcirdpalv hqrpapp  SEQ ID NO:30

FIGURE 17

Region rich in glycosylation sites of human IL-15Ralpha:

nucleic acid sequence =
404..709 of human IL-15Ralpha protein SEQ ID NO:1 =

```
404                                                    tccacag taacgacggc
421 agggtgacc ccacagccag agagcctctc cccttctgga aaagagcccg cagcttcatc
481 tccagctca aacaacacag cggccacaac agcagctatt gtcccgggct cccagctgat
541 gccttcaaaa tcaccttcca caggaaccac agagataagc agtcatgagt cctcccacgg
601 caccccctct cagacaaacag ccaagaactg ggaactcaca gcatccgcct cccaccagcc
661 gccaggtgtg tatccacagg gccacagcga caccactgtg gctatctcc
```

SEQ ID NO: 31 amino acid sequence =
108..209 of human IL-15Ralpha protein SEQ ID NO:3 =

```
108                                                                 stv ttagvtpqpe
121 slspsgkepa asspssnnta attaaivpgs qlmpskspst gtteisshes shgtpsgtta
181 knweltasas hqppgvypqg hsdttvais
```

SEQ ID NO: 32

FIGURE 18 sequence coding for the exon3-encoded part of the region rich in glycosylation sites of human IL-15Ralpha =

404..464 of human IL-15Ralpha SEQ ID NO:1 =

```
404                                                    atcacgtg
421 agggtgacc ccacagccag agagcctctc cccttctgga aaa g          tccacag taacgacggc
                                                              SEQ ID NO: 33
```

108..127 of human IL-15Ralpha protein SEQ ID NO :3 =
exon3-encoded part of region rich in glycosylation sites of human IL-15Ralpha =

```
108                                                    stv ttagvtpqpe
121 slspsgk                                                   SEQ ID NO: 34
``` sequence coding for (it + human IL-15Ralpha sushi domain + i +
all exon3-encoded amino acids) =

173..464 of human IL-15Ralpha SEQ ID NO:1 =

```
173                                                                          atcacgtg
181 ccctcccccc atgtccgtgg aacacgcaga catctgggtc aagagctaca gcttgtactc
241 cagggagcgg tacatttgta actctgtttt caagcgtaaa gccggcacgt ccagcctgac
301 ggagtgccgtg ttgaacaagg ccacgaatgt cgcccactgg acaaccccca gtctcaaatg
361 cattgagacc cctgccctgg ttcaccaaag gccacgcgca cctccacag taacgacggc
421 agggtgacc ccacagccag agagcctctc cccttctgga aaag             SEQ ID NO :35
```

31..127 of human IL-15Ralpha protein SEQ ID NO :3 =
it + human IL-15Ralpha sushi domain + i + all exon3-encoded
amino acids =

```
31                                                     itcpppmsve hadiwvksys lysreryicn
61  sgfkrkagts sltecvlnka tnvahwttps lkcirdpalv hqrpappstv ttagvtpqpe
121 slspsgk                                                   SEQ ID NO:36
```

FIGURE 19

83..697 of human IL-15Ralpha =
sequence coding for a fragment of soluble extracellular domain of
human IL-15Ralpha =

```
 83                   atggcccc gcgcggggcg cgcggctgcc ggaccctcgg
121 tctcccgcg ctgctactgc tgctgctgct ccggccgccg gcgaccgcgg gcatcacgtg
181 ccctcccccc atgtccgtgg aacacgcaga catctggtc aagagctaca gcttgtactc
241 cagggagcgg tacattttgta actctggttt caagctgtaaa gccggcacgt ccagcctgac
301 ggagtgcgtg ttgaacaagg ccacgaatgt cgccactgg acaaccccca gtctcaaatg
361 cattagagac cctgccctgg ttcaccaaag gccagcgcca ccctccacag taaggacggc
421 aggggtgacc ccaagcctctc ccttctgga aagagcccg cagcttcatc
481 tccagctca aacaacacag cggccacaac agcagctatt gtcccgggct cccagctgat
541 gccttcaaaa tcacctttcca caggaaccac agagataagc agtcatgagt cctcccacgg
601 cacccctct cagacaacag ccaagaactg ggaactcaca gcatccgcct cccaccagcc
661 gccaggtgtg tatccacagg gccacagcga caccact
```

SEQ ID NO:37

1..205 of human IL-15Ralpha =
fragment of soluble extracellular domain of human IL-15Ralpha =

```
  1 maprrargcr tlglpallll lllrppatrg itcpppmsve hadiwvksys lysreryicn
 61 sgfkrkagts sltecvlnka tnvahwttps lkcirdpalv hqrpappstv ttagvtpqpe
121 slspsgkepa asspssnnta attaaivpgs qlmpskspst gtteisshes shgtpsqtta
181 knweltasas hqppgvypqg hsdtt
```

SEQ ID NO:38

FIGURE 20

83..709 of human IL-15Ralpha =
sequence coding for a soluble extracellular domain of
human IL-15Ralpha =

```
 83                      atggcccc gcgcggggcg cgcggctgcc ggaccctcgg
121 tctcccgccg ctgctactgc tgctgctgct ccggccgccg gcgccgcggg gcatcacgtg
181 ccctccccc atgtccgtgg aacacgcaga catctggtc aagagctaca gcttgtactc
241 cagggagcgg tacatttgta actctggttt caagcgtaaa gccggcacgt ccagcctgac
301 ggagtgcgtg ttgaacaagg ccacgaatgt cgcccactgg acaaccccca gtctcaaatg
361 cattagagac cctgccctgg ttcaccaaag gccagcgcca ccctccacag taacgacggc
421 aggggtgacc ccacagccag agagcctctc ccctctgga aaagagcccg cagcttcatc
481 tccagctca aacaacacag cggccacaac agcagctatt gtcccgggct cccagctgat
541 gccttcaaaa tcaccttcca caggaaccac agagataagc agtcatgagt cctccacgg
601 caccccctct cagacaacag ccaagaactg ggaactcaca gcatccgcct cccaccagcc
661 gccaggtgtg tatccacagg gccacagcga caccactgtg gctatctcc
```

SEQ ID NO: 39

1..209 of human IL-15Ralpha =
a soluble extracellular domain of human IL-15Ralpha =

```
  1 maprrargcr tlglpalll lllrppatrg itcpppmsve hadiwvksys lysreryicn
 61 sgfkrkagts sltecvlnka tnvahwttps lkcirdpalv hqrpappstv ttagvtpqpe
121 slspsgkepa asspssnnta attaaivpgs qlmpskspst gtteisshes shgtpsqtta
181 knweltasas hqppgvypqg hsdttvais
```

SEQ ID NO: 40

FIGURE 21

173..697 of human IL-15Ralpha =
sequence coding for a fragment of a soluble, signal peptide deleted,
extracellular domain of human IL-15Ralpha =

```
173                                                                atcacgtg
181  ccctccccc  atgtccgtgg  aacacgcaga  catctggtc   aagagctaca  gcttgtactc
241  cagggagcgg  tacatttgta  actctggttt  caagcgtaaa  gccggcacgt  ccagcctgac
301  ggagtgcgtg  ttgaacaagg  ccacgaatgt  cgcccactgg  acaaccccca  gtctcaaatg
361  cattagagac  cctgccctgg  ttcaccaaag  gccagcgcca  ccctgcacag  taacgacggc
421  agggtgacc   ccacagccag  agccctctc   ccttctgga   aaagagcccg  cagcttcatc
481  tcccagctca  aacacacag   cggccacaac  agcagtatt   gtcccgggct  ccagctgat
541  gccttcaaaa  tcaccttcca  caggaaccac  agagataagc  agtcatgagt  cctcccacgg
601  cacccctct   cagacaaacag ccaagaactg  ggaactcaca  gcatccgcct  cccaccagcc
661  gccaggtgtg  tatccacagg  gccacagcga  caccact

SEQ ID NO:41
```

31..205 of human IL-15Ralpha =
fragment of a soluble, signal peptide deleted, extracellular
domain of human IL-15Ralpha =

```
 31                                   itcpppmsve hadiwvksys lysreryicn
 61  sgfkrkagts sltecvlnka tnvahwttps lkcirdpalv hqrpappstv ttagvtpqpe
121  slspsgkepa asspssnnta attaaivpgs qlmpskspst gtteisshes shgtpsqtta
181  knweltasas hqppgvypqg hsdtt

SEQ ID NO:42
```

FIGURE 22

173..709 of human IL-15Ralpha =
sequence coding for a soluble, signal peptide deleted,
extracellular domain of human IL-15Ralpha =

```
173                                                                atcacgtg
181 ccctcccccc atgtccgtgg aacacgcaga catctgggtc aagagctaca gcttgtactc
241 cagggagcgg tacatttgta actctggttt caagcgtaaa gccggcacgt ccagcctgac
301 ggagtgcgtg ttgaacaagg ccacgaatgt cgcccactgg acaaccccca gtctcaaatg
361 cattagagac cctgccctgg ttcaccaaag gccagcgcca ccctccacag taacgacggc
421 aggggtgacc ccacagccag agagcctctc ccctctgga aagagcccg cagcttcatc
481 tcccagctca aacaacacag cggccacaac agcagctatt gtcccgggct ccagctgat
541 gccttcaaaa tcacctttcca caggaaccac agagataagc agaactcaca agtcatgagt cctcccacgg
601 cacccctct cagacaacag ccaagaactg ggaactcaca gcatccgcct cccaccagcc
661 gccaggtgtg tatccacagg gccacagcga ccactgtg gctatctcc
                                                            SEQ ID NO:43
```

31..209 of human IL-15Ralpha =
a soluble, signal peptide deleted, extracellular
domain of human IL-15Ralpha =

```
 31                        itcpppmsve hadiwvksys lysreryicn
 61 sgfkrkagts sltecvlnka tnvahwttps lkcirdpalv hqrpappstv ttagvtpqpe
121 slspsgkepa asspssnnta attaaivpgs qlmpskspst gtteisshes shgtpsqtta
181 knweltasas hqppgvypqg hsdttvais
                                                            SEQ ID NO:44
```

FIGURE 23

Homo sapiens interleukin 15 (IL15), transcript variant 3, mRNA (1496 bp)
ACCESSION NUMBER NM_000585 (VERSION NM_000585.2 GI:26787979) =

```
   1 gactccggt ggcaggcgcc cggggaatc ccagctgact cgctcactgc cttcgaagtc
  61 cggcgcccc cggagggaa ctgggtggcc gcaccctccc ggctgcggtg gctgtcgccc
 121 cccaccctgc agccaggact cgatggagaa tccattccaa tatatgcca tgtggctctt
 181 tggagcaatg ttccatcatg ttccatgctg ctgctgacgt cacatggagc acagaaatca
 241 atgttagcag atagccagcc catacaagat cgtattgtat tgtaggaggc atcgtggatg
 301 gatgctgct ggaaacccct tgccatagcc agctcttctt caatacttaa ggattaccg
 361 tggctttgag taatgagaat ttcgaaacca catttgagaa gtatttccat ccagtgctac
 421 ttgtgttttac ttctaaacag tcattttcta actgaagctg gcattcatgt cttcattttg
 481 ggctgtttca gtgcagggct tcctaaaaca gaagccaact gggtgaatgt aataagtgat
 541 ttgaaaaaaa ttgaagatct tattcaatct atgcatattg atgctactt atatacggaa
 601 agtgatgttc acccagttg caaagtaaca gcaatgaagt gctttctctt ggagttacaa
 661 gttatttcac ttgagtccgg agatcgcaagt atccatgata cagtagaaaa tctgatcatc
 721 ctagcaaaca acagtttgtc ttctaatggg aatgtaacag aatctgatg caaagaatgt
 781 gaggaactgg aggaaaaaaa tattaaagaa tttttgcaga gttttgtaca tattgtccaa
 841 atgttcatca acacttcttg attgcaattg attcttttta aagtgttttct gttattaaca
 901 aacatcactc tgctgcttag acataacaaa acactcggca tttcaaatgt gctgtcaaaa
 961 caagttttc tgtcaagaag atgatcagag cttggatcag atgaactctt agaaatgaag
1021 gcagaaaaat gtcattgagt atatagtgta ctatgaactt ctctcagact tactttactc
1081 atttttttaa tttattattg aaattgtaca tatttgtgga ataatgtaaa atgttgaata
1141 aaaatatgta caagtgttgt tttttaagtt gcactgatat tttacctctt attgcaaaat
1201 agcatttgtt taaggtgtgt agtcaaatta tgtattggtg gggctgggta ccaatgctgc
1261 aggtcaaacag ctatgctggt aggctcctgc cagtgtggaa ccactgacta ctggcctca
1321 ttgacttcct tactaagcat agcaaacaga ggaagaattt gttatcagta agaaaagaa
1381 gaactatatg tgaatcctct tctttatact gtaatttagt tattgatgta taaagcaact
1441 gttatgaaat aaagaaattg caataactgg caaaaaaaaa aaaaaaaaaa aaaaaa
```

SEQ ID NO: 45

FIGURE 24

Interleukin 15 isoform 1 precursor [Homo sapiens] (162 aa) =
ACCESSION  NP_000576 (VERSION  NP_000576.1  GI:10835153) =
           [CDS          373..858 of SEQ ID NO :45] =
  1 mriskphlrs isiqcylcll lnshflteag ihvfilgcfs aglpkteanw vnvisdlkki
 61 edliqsmhid atlytesdvh psckvtamkc fllelqvisl esgdasihdt venliillann
121 slssngnvte sgckeceele eknikeflqs fvhivqmfin ts           SEQ ID NO: 46

Sequence coding for human wild-type mature IL-15 =
      517..858 of SEQ ID NO:45 =

517                                      aact gggtgaatgt aataagtgat
541 ttgaaaaaaa ttgaagatct tattcaatct atgcatattg atgctacttt atatacggaa
601 agtgatgttc acccagttgc caaagtaaca gcaatgaagt gctttctctt ggagttacaa
661 gttatttcac ttgagtccgg agatgcaagt attcatgata cagtagaaaa tctgatcatc
721 ctagcaaaca acagtttgtc ttctaatggg aatgtaacag aatctggatg caaagaatgt
781 gaggaactgg aggaaaaaaa tattaaagaa ttttttcaga gttttgtaca tattgtccaa
841 atgttcatca acacttct                                       SEQ ID NO: 47

Human wild-type mature IL-15 =
   49..162 of SEQ ID NO:46 =

49                                              nw vnvisdlkki
 61 edliqsmhid atlytesdvh psckvtamkc fllelqvisl esgdasihdt venliillann
121 slssngnvte sgckeceele eknikeflqs fvhivqmfin ts          SEQ ID NO: 48

FIGURE 25

LINKER 20:
nucleic acid sequence =
agcgggcggctcagggggtggaggatctctggtggtggaagtggaggtggcgggtctctgcag
SEQ ID NO: 49 amino acid sequence =
sggsgggsgggsggggslq
SEQ ID NO: 50

LINKER 26:
nucleic acid sequence =
tctggtggcggatcagggggtggcggatctggcggggtggaagtggaggtggcggatctggcggaggttcactgcag
SEQ ID NO: 51 amino acid sequence =
sgggsggggsggggsggggslq
SEQ ID NO: 52

FIGURE 26

Flag tag and Factor Xa binding site:

nucleic acid sequence =
gactacaaggatgacgatgacaagatagaaggtagg          SEQ ID NO: 53 amino acid sequence =
dykddddkiegr          SEQ ID NO: 54

Flag tag and Factor Xa binding site:

nucleic acid sequence =
accacgcgtgactacaaggatgacgatgacaagatagaaggtagg          SEQ ID NO:55 amino acid sequence =
ttrdykddddkiegr          SEQ ID NO:56

Signal peptide of bovine preprolactine:

nucleic acid sequence =
atggacagca aaggttcgtc gcagaaagca gggtcccgcc tgctcctgct gctggtggtg tcaaatctac
tcttgtgcca gggtgtggtc tcc          SEQ ID NO:57 amino acid sequence =
mdskgssqkagsrllllvvsnllclcqgvvs          SEQ ID NO:58

Kozak sequences:

IL-15R Kozak sequence:
gcc gcc

Preprolactine Kozak sequence:
gcc acc

FIGURE 27

Fusion proteins [sushi domain of IL-15Ralpha + IL15]:

RLI fusion protein :
= signal peptide of IL-15Ralpha + Flag tag and Xa binding site + it + sushi + i + rd + eleven exon3-encoded aa + linker 20 + human wild-type mature IL-15 nucleic acid sequence:
= Kozak sequence + SEQ ID NO: 4 + SEQ ID NO: 52 + SEQ ID NO: 29 + SEQ ID NO: 49 + SEQ ID NO: 47 + STOP codon = gccgccatggccccgcgcgcggcgcggcctgcctccggctctccggcgctgctgctcctgctgctgcccggccccgcc
gacgcggggcgactacaaggatgacgatgacaagatagaaggtaggaacacatgccctcccccatgcgtccgtgaacacgcagaca
tctgggtcaagagctacagtcttgtactccaggagcttgcgccgaatgtcgcccactggagacagcattgtaactctgtttcaagccgcacgtccagctg
acagagtgcgtgttgaacaaggccacgagcgcccagcgtgtttgaggggtctcaggtgtgaagcatcgcccactggagacagttcatattgatgcgacagttggtccttca
ccaaaggccagccagccgcgggcagggtgagtcagggggtgaggtatcttgaagatcttaattcaatctattgatctttatatacgaaaagtgattgtt
tgaatgtaataagtgattgaaaaaatgatgaagatgcttttctcttgagttaaccagtctggaaacagcatgatttaacagacagagaaattgatctgagatgcaagtattca
cacccccagttgcaaagtaacagagaagttgctttctcttgagttcactcttgagctgcagatgcaagtattca
tgatacagtagaaaatctgatcatcctagcaaacaacagtttgtcttctcaatggaatgtaacagaatctggatgcaaagaatgtg
aggaactggagagaaaaatattaaagaatttgcagagttttgttacatattgtccaaatgtgtcatcaacacttcttag <u>SEQ ID NO: 59</u> amino acid sequence:
= SEQ ID NO: 5 + SEQ ID NO: 54 + SEQ ID NO: 30 + SEQ ID NO: 50 + SEQ ID NO: 48 = maprrargcrtlgiplalllllllrppatrgdykddddkiegritcpppmsvehadiwvksysly srervicns
gfkrkagtssltecvlnkatnvahwttpslkciirdpalvhqrpappsggsgggsgggsgggslqnwvnvis
dlkkiedliqsmhidatlytesdvhpsckvtamkcflelqvislesgdasihdtvenliilannsIssngnv
tesgckeceleekni kef lqsfvhivqmfints <u>SEQ ID NO: 60</u>

FIGURE 28

Fusion proteins [sushi domain of IL-15Ralpha + IL15]:

ILR fusion protein :
= signal peptide of bovine preprolactine + Flag tag and Xa binding site + human wild-type mature IL-15 + linker 26 + it + sushi + i + rd + eleven exon3-encoded amino acids nucleic acid sequence:
= Kozak sequence + SEQ ID NO: 57 + SEQ ID NO: 55 + SEQ ID NO: 47 + SEQ ID NO: 51
+ SEQ ID NO: 29 + STOP codon = gccaccatggacagcaagggttcgtcgcagaaagcaggtcccgcctgctcctgtgttgtgtcaaatctactcttgtgcca
gggtggtggtctccaccacgcgagactacaagatgacgatgacgataggacaaggcgtaactggtgaatgtaataagtgatttga
aaaaattgaagatcttattcaatctatgatgcataagtttatatacggaaagtgatgttcaccccagtgcaaagtaaca
gcaatgaagtgcttttctcttggagttacaagttcatttcacttgagtccggagatgcaagtgcaagtagtagaaaatctgat
catcctagcaaacaacagtttgtcttcttgtacatattgtccaaaatgttcatcaacactagttctgttggtggcggatct
ttaaagaattttgcagagttttggaagtggaggtggccggtgtccaaggttcactgcagactacatgcccctccccatgtcgtgaacacgcaga
catctggtcaagctacagttgtactccaggagagagcggtacatttgtaactctgttcaagcgtttcaagatcattagagacccgtcctgtt
tgacagagtgcgtgtgaacaaggcacagaatgtcgccactgacaaccccagtctcaaatgtctgacattagagacccgtcctgtt
caccaaaggccagcgccaccctga $$\text{SEQ ID NO: 61}$$

amino acid sequence:
= SEQ ID NO: 58 + SEQ ID NO: 56 + SEQ ID NO: 48 + SEQ ID NO: 52 + SEQ ID NO: 30 =
mdskgssqkagsrlllllvvsnllcggvvsttrdykdddkiegrnwvnvisdlkkiedliqsmhidatlyt
esdvhpsckvtamkcfllelqvislesgdasihdtvenliilannslssngnvtesgckeceeleeknikefl
qsfvhivqmfintssgggsgggggsggggsggggslqitopppmsvehadiwvksyslysreryicnsgf
krkagtssltecvlnkatnvahwttpslkcirdpalvhgrpapp $$\text{SEQ ID NO: 62}$$

FIGURE 29

Human interleukin 2 nucleic acid sequence =

Homo sapiens interleukin 2 (IL2), mRNA (1047 bp) =
ACCESSION NUMBER NM 000586 (VERSION NM 000586.2 GI:28178860)

```
   1 cgaattcccc tatcaccctaa gtgtgggcta atgtaacaaa gagggatttc acctacatcc
  61 attcagtcag tctttgggg tttaaagaaa ttccaaagag tcatcagaag aggaaaaatg
 121 aagtaatgt tttttcagac agtaaagtc tttgaaaata tgtgtaatat gtaaaacatt
 181 ttgacacccc cataatattt ttccagaatt aacagtataa attgcatctc ttgttcaaga
 241 gttccctatc actctcttta atcactactc acagtaacct caactcctgc cacaatgtac
 301 aggatgcaac tcctgtcttg cattgcacta agtcttgcac ttgtcacaaa cagtgcacct
 361 acttcaagtt ctacaaagaa aacacagcta caactggagc attactgct ggatttacag
 421 atgattttga atggaattaa taattacaag aatcccaaac tcaccaggat gctcacattt
 481 aagtttaca tgcccaagaa ggccacagaa ctgaaacatc ttcagtgtct agaagaagaa
 541 ctcaaacctc tggaggaagt gctaaattta gctcaaagca aaaactttca cttaagaccc
 601 agggacttaa tcagcaatat caacgtaata gttctggaac taaagggatc tgaaacaaca
 661 ttcatgtgtg aatatgctga tgagacagca accattgtag aattctgaa cagatggatt
 721 accttttgtc aaagcatcat ctcaacactg acttgataat taagtgcttc ccacttaaaa
 781 catatcaggc cttctattta tttaaatatt taaattttat attattgtt gaatgtatgg
 841 tttgctacct attgtaacta ttattcttaa tcttaaaact ataaatatgg atcttttatg
 901 attcttttg taagcctag atggtttcac atggtttcac atgttttcac caaaatattt
 961 attattatgt tgaatgttaa atatagtatc tatgtagatt ggttagtaaa actatttaat
1021 aaatttgata aatataaaaa aaaaaaa
```

SEQ ID NO: 63

FIGURE 30

Sequence coding for human wild-type mature IL-2 =
355..753 of SEQ ID NO:63 =

```
355                                                             gcacct
361 acttcaagtt ctacaaagaa aacacagcta caactggagc attactgct ggatttacag
421 atgattttga atggaattaa taattacaag aatcccaaac tcaccaggat gctcacattt
481 aagttttaca tgcccaagaa ggccacagaa ctgaaacatc ttcagtgtct agaagaagaa
541 ctcaaacctc tggaggaagt gctaaattta gctcaaagca aaaactttca cttaagaccc
601 agggacttaa tcagcaatat caacgtaata gttctggaac taaagggatc tgaaacaaca
661 ttcatgtgtg aatatgctga tgagacagca accattgtag aatttctgaa cagatggatt
721 acctttgtc aaagcatcat ctcaacactg act
```

SEQ ID NO: 64

Amino acid sequence of human wild-type mature IL-2 = aptssstkktqlqlehllldlqmilnginnynknpkltrmltfkfympkkatelkhlqclccclkplcevlnla
qsknfhlrprdlisnlninvlvlelkgsettfmccyadetatlvefInrwitfcqsiistlt

SEQ ID NO: 65

Linker IL-2:

nucleic acid sequence =
ctgcag amino acid sequence =
lq

FIGURE 31

Sushi-containing fragment of IL-15Ralpha, tagged by IL-2:
= signal peptide of IL15-Ralpha + it + sushi + i + rd + lg + IL-2 nucleic acid sequence:
= Kozak sequence + SEQ ID NO:4 + SEQ ID NO:27 + linker IL-2 + SEQ ID NO:64 + STOP codon = gccgccatggcccc gcggcgggcg cgcggctgcc ggaccctcgg
tctcccggcg ctgctactgc tgctgctgct ccggccgccg gcgacgcggg gcatcacgtg
ccctcccccc atgtccgtgg aacacgcaga catctgggtc aagagctaca gcttgtactc
cagggagcgg tacatttgta actctggttt caagcgtaaa gccggcacgt ccagcctgac
ggagtgcgtg ttgaacaagg ccacgaatgt cgcccactgg acaacccccca gtctcaaatg
cattagagac ctgcaggcacct acttcaagtt ctacaaagaa aacacagcta caactggagc
atttactgct ggatttacag
atgattttga atggaattaa taattacaag aatcccaaac tcaccaggat gctcacattt
aagttttaca tgcccaagaa ggccacagaa ctgaaacatc ttcagtgtct agaagaagaa
ctcaaacctc tggaggaagt gctaaattta gctcaaagca aaaactttca cttaagaccc
agggacttaa tcagcaatat caacgtaata gttctggaac taaagggatc tgaaacaaca
ttcatgtgtg aatatgctga tgagacagca accattgtag aatttctgaa cagatggatt
accttttgtc aaagcatcat ctcaacactg acttga

SEQ ID NO: 66 amino acid sequence:
= SEQ ID NO:5 + SEQ ID NO:28 + lq + SEQ ID NO:65 =
maprrargcrtlglpalllllllrppatrgitcpppmsvehadiwvksyslysreryicnsgfkrkagtss
ltecvlnkatnvahwttpslkcirdlqaptssstkktqlqlehllldlqmilnginnyknpkltrmltfkfym
pkkatelkhlqcleeelkpleevlnlaqsknfhlrprdlisninvivlelkgsettfmceyadetativefln
rwitfcqsiistlt
SEQ ID NO: 67

FIGURE 32

Fragment of extracellular region of IL-15Ralpha, tagged with IL-2:
= signal peptide of human IL15-Ralpha + fragment of extracellular part of IL15-Ralpha + lq + IL-2* nucleic acid sequence:
= Kozak sequence + *SEQ ID NO:4* + *SEQ ID NO:37* + linker IL-2 + SEQ ID NO:64 + STOP codon = gccgccatggcccc gcggcggcg cgcggctgcc ggaccctcgg
tctcccggcg ctgctactgc tgctgctgct ccggccgccg gcgacgcggg gcatcacgtg
ccctcccccc atgtccgtgg aacacgcaga catctgggtc aagagctaca gcttgtactc
cagggagcgg tacatttgta actctggttt caagcgtaaa gccggcacgt ccagcctgac
ggagtgcgtg ttgaacaagg ccacgaatgt cgcccactgg acaaccccca gtctcaaatg
cattagagac cctgccctgg ttcaccaaag gccagcgcca ccctccacag taacgacggc
aggggtgacc ccacagccag agagcctctc cccttctgga aaagagcccg cagcttcatc
tcccagctca aacaacacag cggccacaac agcagctatt gtcccgggct cccagctgat
gccttcaaaa tcaccttcca caggaaccac agagataagc agtcatgagt cctcccacgg
caccccctct cagacaacag ccaagaactg ggaactcaca gcatccgcct cccaccagcc
gccaggtgtg tatccacagg gccacagcga caccactctg caggcaccta cttcaagtt
ctacaaagaa aacacagcta caactggagc atttactgct ggatttacag
atgattttga atggaattaa taattacaag aatcccaaac tcaccaggat gctcacattt
aagttttaca tgcccaagaa ggccacagaa ctgaaacatc ttcagtgtct agaagaagaa
ctcaaacctc tggaggaagt gctaaattta gctcaaagca aaaactttca cttaagaccc
agggacttaa tcagcaatat caacgtaata gttctggaac taaagggatc tgaaacaaca
ttcatgtgtg aatatgctga tgagacagca accattgtag aatttctgaa cagatggatt
accttttgtc aaagcatcat ctcaacactg acttga

SEQ ID NO: 68 amino acid sequence:
= SEQ ID NO:5 + SEQ ID NO:38 + lq + SEQ ID NO:65 =
maprrargcrtlglpallllllrppatrgitcpppmsvehadiwvksyslysreryicnsgfkrkagtss
ltecvlnkatnvahwttpslkcirdpalvhqrpappstvttagvtpqpeslspsgkepaasspssnntaatt
paivpgsqlmpskspstgtteisshesshgtpsqttaknweltapashqppgvypqghsdttlqaptssstk
ktqlqlehllldlqmilnginnyknpkltrmltfkfympkkatelkhlqcleeelkpleevlnlaqsknfhl
rprdlisninvivlelkgsettfmceyadetativeflnrwitfcqsiistlt

SEQ ID NO: 69

FIGURE 33

Mouse interleukin-15 receptor alpha chain precursor (IL15Ralpha), transcript variant 1, mRNA (792 bp)
ACCESSION NUMBER NM_008358 (VERSION NM_008358.1 GI:6680408)

```
  1 atggcctcgc cgcagctccg gggctatgga gtccaggcca ttcctgtgtt gctgctgctg
 61 ctgttgctac tgttgctccc gctgagggtg gctgggggca acgccgggca ccacgtgtcc acctcccgta
121 tctattgagc atgctgacat ccgggtcaag aattacagtg tgaactccag ggagaggtat
181 gtctgtaact ctggctttaa gcggaaagct ggaacatcca ccctgattga gtgtgtgatc
241 aacaagaaca caaatgttgc ccactggaca actccagcc tcaagtgcat cagagaccc
301 tccctagctc actacagtcc agtgcaaaca gtagtgacac caaggtgac ctcacagcca
361 gagagcccct cccctctgc aaaagagcca gaagctttct ctcccaaatc agatacgca
421 atgaccacag agacagctat tatgcctggc tccaggctga ccacatccca aacaacttct
481 gcaggaacta caggacagg cagtcacagc ctccacctcc cccatctct tgcagcaaca
541 atgaccttgg agcctacagc ctctctaca tcggtcctct cagagatttc tcccacagt
601 tccaaaatga cgaaagtggc catctctaca tcggtcctct cagagatttc tggttggtgc agggttgtg
661 atggctttcc tggcctggta catcaaatca aggcagcctt ctcagcgtg ccgtgttgag
721 gtggaaacca tggaaacagt accaatgact gtgagggcca gcagcaagga ggatgaagac
781 acaggagcct aa
```

SEQ ID NO: 72

Mouse Interleukin-15 receptor alpha chain precursor (IL-15Ralpha) (263 aa)
ACCESSION Q60819 (VERSION Q60819 GI:59799764)

```
  1 maspqlrgyg vqaipvllll llllllplrv tpgttcpppv slehadirvk nysvnsrery
 61 vcnsgfkrka gtstliecvi nkntnvahwt tpslkcirdp slahyspvpt vvtpkvtsqp
121 espspsakep eafspksdta mttetalmpg srltpsqtts agttgtgshk ssrapslaat
181 mtleptasts lriteisphs skmtkvaist svllvgagvv maflawyiks rqpspqcrve
241 vetmetvpmt vrasskeded tga
```

SEQ ID NO: 73

FIGURE 34

1..205 of mouse IL-15Ralpha protein SEQ ID NO: 73 =
mouse IL-15Ralpha extracellular region =

```
  1 maspqlrgyg vqalpvllll llllllplrv tpgttcpppv siehadirvk nysvnsrery
 61 vcnsgfkrka gtstliecvi nkntnvahwt tpslkcirdp slahyspvpt vvtpkvtsqp
121 espspsakep eafspksdta mttetaimpg srltpsqtts agttgtgshk ssrapslaat
181 mtleptasts lriteisphs skmtk
```
SEQ ID NO: 74

36..96 of mouse IL-15Ralpha protein SEQ ID NO: 73 =
mouse IL-15Ralpha sushi domain =

```
 36                                  cpppv siehadirvk nysvnsrery
 61 vcnsgfkrka gtstliecvi nkntnvahwt tpslkc
```
SEQ ID NO: 75

97..109 of mouse IL-15Ralpha protein SEQ ID NO: 73 =
hinge region of mouse IL15-Ralpha =

```
 97 irdp slahyspvp
```
SEQ ID NO: 76

110..205 of mouse IL-15Ralpha SEQ ID NO: 73 =
tail region of mouse IL15-Ralpha =

```
110                                                      t vvtpkvtsqp
121 espspsakep eafspksdta mttetaimpg srltpsqtts agttgtgshk ssrapslaat
181 mtleptasts lriteisphs skmtk
```
SEQ ID NO: 77

FIGURE 35

Pan troglodytes (chimpanzee) similar to interleukin 15 receptor, alpha (LOC466284), mRNA (1035 bp)
ACCESSION XM_521684 (VERSION XM_521684.1 GI:55634956)

```
   1 atggagaaat tcacctggca cacaagaggc atcacgtgcc ctcccccat gtccgtggaa
  61 cacgcagaca tctggtcaa gagctacagc ttgtactcca gggagcggta catttgtaac
 121 tctgtttca agcgtaaagc cggcacgtcc agcctgacgg agtcgtgtt gaacaaggcc
 181 acgaatgtcg cccactggac ctcaaatgca ctcaaatgca ttagagaccc tgccctgtt
 241 ctccaaaggc cagtgccacc ctccacagta acgacgcag ggatgacccc acagcagag
 301 agcctctccc cttctggaaa agttccgtg gctgtcacaa tggaagacac atttttcatg
 361 gagagggaac agcacagtta cgccacaccc ttacagtgca ggggcagcca ccttccaggg
 421 aaggacaagg aagacaggga agacgctgaa acaaggcag cctctgttcc tgagcgcaag
 481 ctcatcagga cgctttcctc ccacacagcg cggagagttc agccagagc ccaggcttc
 541 cgtgtttcac acgcagccgc tccgagcgtc ctcggccagc ctcggcccag gcagttcac ctgctctcag
 601 ctgacctcc agcagcccgc agcttcatct cccagctcaa acacccaca ggccacaaca
 661 gcagctattg tcccgggctc ccagctgatg cctttcccaaa caccttccac aggaaccaca
 721 gagataggca gtcatgagtc ctcccacggc acccctctc agacaacagc caagacctgg
 781 gaactcacag catctgcctc ccaccagccg ccaggtgtgt ccaggtgtgt atccagcgac
 841 accactgtgg ctatctccac gtccactgtc ggctgagcgc tgtgtctctc
 901 ctggcatgct acctcaagtc aaggcaaact ccccgctgg ccagcgttga aatgaaagcc
 961 atggaggctc tgccggtgac tgggggacc agcagcagag atgaagactt ggaaaactgc
1021 tctcaccacc tatga
```
SEQ ID NO: 78

Similar to interleukin 15 receptor, alpha [Pan troglodytes], (344 aa)
ACCESSION XP_521684 (VERSION XP_521684.1 GI:55634957)

```
  1 mekftwhtrg itcpppmsve hadiwvksys lysreryicn sgfkrkagts sltecvlnka
 61 tnvahwttps lkcirdpalv lqrpvppstv ttagmtpqpe slspsgkgsv avtmedtffm
121 ereqhsyatp lqcrgshlpg kdkedredae hkaasvperk lirtlsshta rrvqaragas
181 rvshaaapsv lggrsftcsq lslgqpaass psnttaatt aaivpgsqlm pskspstgtt
241 eigshesshg tpsqttaktw eltasashqp pgvypgghsd ttvaistsv licglsavsl
301 lacylksrgt pplasvemea mealpvtggt ssrdedlenc shhl
```
SEQ ID NO: 79

FIGURE 36

```
1..286 of simian IL-15Ralpha SEQ ID NO: 79 =
extracellular region of simian IL15-Ralpha =

1 mekftwhtrg itcpppmsve hadiwvksys lysreryicn sgfkrkagts sltecvlnka
      61 tnvahwttps lkcirdpalv lqrpvppstv ttagmtpqpe slspsgkgsv avtmedtffm
     121 ereqhsyatp lqcrgshlpg kdkedredae hkaasvperk lirtlsshta rrvqaraqas
     181 rvshaaapsv lgqrsftcsq lslqqpaass pssnttaatt aaivpgsqlm pskspstgtt
     241 eigshesshg tpsqttaktw eltasashqp pgvypqghsd ttvais
                                                                  SEQ ID NO: 80

13..73 of simian IL-15Ralpha protein SEQ ID NO: 79 =
simian IL-15Ralpha sushi domain =

13 cpppmsve hadiwvksys lysreryicn sgfkrkagts sltecvlnka
      61 tnvahwttps lkc
                                                                  SEQ ID NO: 81

74..88 of simian IL-15Ralpha SEQ ID NO: 79 =
hinge region of simian IL15-Ralpha =

74 irdpalv lqrpvpps
                                                                  SEQ ID NO: 82

89..286 of simian IL-15Ralpha SEQ ID NO: 79 =
tail region of simian IL15-Ralpha =

61                               tv ttagmtpqpe slspsgkgsv avtmedtffm
     121 ereqhsyatp lqcrgshlpg kdkedredae hkaasvperk lirtlsshta rrvqaraqas
     181 rvshaaapsv lgqrsftcsq lslqqpaass pssnttaatt aaivpgsqlm pskspstgtt
     241 eigshesshg tpsqttaktw eltasashqp pgvypqghsd ttvais

SEQ ID NO: 83
```

FIGURE 37

Rattus norvegicus similar to interleukin 15 receptor precursor (LOC502145), mRNA, (765bp)ACCESSION XM_577598 (VERSION XM_577598.1 GI:62663873)

```
  1 atgagcatc acagagaatc gtggaaatta tgggaccca acagggaaga catcgagaag
 61 ggcatcacgt gcccaacgcc catatctatt gaacacgcag acatccgggt caagaattac
121 agtgtgaact ccagggagag gtatgtctgt aactctggct tcaagcggaa agcaggcaca
181 tccaccctga ccgagtgcgt gatcaataag aacacgaatg tggccactg gacaactccc
241 aacctcaagt gtatcaagcc agaagcttta tctcccaaat cagatagcac agtggccaca
301 gagacagcta ttgtgcctgg ctccaggctg acaccatcc aagcagcttc tgcaggaact
361 acaggacgg gcagacacaa gtcctccca gcccatctc ttgcaacaac aatgacattg
421 gagcctacag cctccactc cctcaggata acagagatti ctccgcacag ttccgaaatg
481 acaaaaggtg agtatttct tttgttttgat gtgttataa ccaggcact acaaagcaga
541 cccagcatgc tcatcagcct ggtccaggcc actctagcac agtcgccagc agtatgccct
601 ttgcctcgcc gaaatgtctc cgttagagag caagcttctc agccgcgtcg tgttgaggtg
661 gaaaccatgg aaacagtacc aatgactgtg agggcccgca gcaaggagga cgaagaccac
721 acgacttcag aaacttcagg agaccagccc agccgcggag tctga
```

SEQ ID NO: 84 similar to interleukin 15 receptor precursor [Rattus norvegicus], (254 aa), ACCESSION XP_577598 (VERSION XP_577598.1 GI:62663874)

```
  1 mehhreswkl wgpnrediek gitcptpisi ehadirvkny svnsreryvc nsgfkrkagt
 61 stltecvink ntnvahwttp nlkcikpeal spksdttvat etaivpgsrl tpsqaasagt
121 tgtgrhkssp apslattmtl eptastsiri teisphssem tkgeyflfd vfiitralgsr
181 psmlislvqa tlaqspavcp lprrnvsvre qasqprrvev etmetvpmtv rarskededh
241 ttsetgqdp trgv
```

SEQ ID NO: 85

FIGURE 38

1..182 of rat IL-15Ralpha protein SEQ ID NO: 85 =
rat IL-15Ralpha extracellular region =

```
  1 mehhreswkl wgpnrediek gitcptpisi ehadirvkny svnsreryvc nsgfkrkagt
 61 sltecvink ntnvahwttp nlkcikpeal spksdttvat etaivpgsrl tpsqaasagt
121 tgtgrhkssp apslattmtl eptastslri teisphssem tkgeyfllfd vfitralqsr
181 ps
                                                          SEQ ID NO: 86
```

24..84 of rat IL-15Ralpha protein SEQ ID NO: 85 =
rat IL-15Ralpha sushi domain =

```
  1 cptpisi ehadirvkny svnsreryvc nsgfkrkagt
 61 sltecvink ntnvahwttp nlkc
                                                          SEQ ID NO: 87
```

85..96 of rat IL-15Ralpha SEQ ID NO: 85 =
hinge region of rat IL15-Ralpha =

```
 85 ikpeal spksdt
                                                          SEQ ID NO: 88
```

97..182 of rat IL-15Ralpha SEQ ID NO: 85 =
tail region of rat IL15-Ralpha =

```
 97                                        tvat etaivpgsrl tpsqaasagt
121 tgtgrhkssp apslattmtl eptastslri teisphssem tkgeyfllfd vfitralqsr
181 ps
                                                          SEQ ID NO: 89
```

FIGURE 39 exon 3 of mouse IL-15Ralpha =
293..385 of mouse IL-15Ralpha protein SEQ ID NO:72 =

```
293                                                             gagaccccc
301 tccctagctc actacagtcc agtgccaaca gtagtgacac caaaggtgac ctcacagcca
361 gagagccccct cccctctgc aaaag
```

SEQ ID NO: 90 exon 3 of simian IL-15Ralpha =
224..322 of Pan troglodytes IL-15Ralpha protein SEQ ID NO:78 =

```
224                                                   gagaccc tgccctggtt
241 ctccaaaggc cagtgccacc ctccacagta acgacggcag ggatgacccc acagccagag
301 agcctctccc cttctggaaa ag
```

SEQ ID NO: 91 exon 3 of rat IL-15Ralpha =
257..454 of Rattus norvegicus IL-15Ralpha protein SEQ ID NO:84 =

```
257               agcc agaagcttta tctcccaaat cagataccac agtggccaca
301 gagacagcta ttgtgcctgg ctccaggctg acaccatccc aagcagcttc tgcaggaact
361 acaggacgg gcagacacaa gtcctcccca gcccatctc ttgcaacaac aatgaccttg
421 gagcctacag cctccacctc cctcaggata acag
```

SEQ ID NO: 92

FIGURE 40

Exon 3 encoded part of IL-15Ralpha =
Hinge + exon 3 encoded part of IL-15Ralpha tail Exon 3 encoded part of human IL-15Ralpha =
95..127 of SEQ ID NO: 40 =
95      rdpalv hqrpappstv ttagvtpqpe                           SEQ ID NO:93
121 slspsgk exon 3 encoded part of mouse IL-15Ralpha =
98..128 of SEQ ID NO:74 =
98                                    rdp slahyspvpt vvtpkvtsqp
121 espspsak                                                   SEQ ID NO: 94 exon 3 encoded part of simian IL-15Ralpha =
75..107 of SEQ ID NO:80 =
75 rdpalv lqrpvppstv ttagmtpqpe slspsgk                        SEQ ID NO: 95 exon 3 encoded part of rat IL-15Ralpha =
86..151 of SEQ ID NO:86 =
86            kpeal spksdttvat etaivpgsrl tpsqaasagt
121 tgtgrhkssp apslattmtl eptastslri t                         SEQ ID NO: 96

FIGURE 41

Exon 2 encoded part of IL-15Ralpha (contains the sushi domain):

Exon 2 encoded part of human IL-15Ralpha =
31..94 of SEQ ID NO: 40 =
31        itcpppmsve hadiwvksys lysreryicn
61 sgfkrkagts sltecvlnka tnvahwttps lkci
SEQ ID NO: 24 exon 2 encoded part of mouse IL-15Ralpha =
32..97 of SEQ ID NO:74 =
33        gttcpppv siehadirvk nysvnsrery
61 vcnsgfkrka gtstliecvi nkntnvahwt tpslkci
SEQ ID NO: 97 exon 2 encoded part of simian IL-15Ralpha =
10..74 of SEQ ID NO:86 =
10       g itcpppmsve hadiwvksys lysreryicn sgfkrkagts sltecvlnka
61 tnvahwttps lkci
SEQ ID NO: 98 exon 2 encoded part of rat IL-15Ralpha =
21..85 of SEQ ID NO:86 =
21       gitcptpisi ehadirvkny svnsreryvc nsgfkrkagt
61 sltecvink ntnvahwttp nlkci
SEQ ID NO: 99

FIGURE 42

IL-15RALPHA SUSHI DOMAIN—IL-15 FUSION PROTEINS

TECHNICAL FIELD OF THE INVENTION

The present invention relates to the field of cytokine-induced and/or cytokine-stimulated biological responses, more particularly to the field of IL-15-induced and/or IL-15-stimulated biological responses, and especially to the field of those biological responses which involve an IL15Rβ/γ signalling pathway.

BACKGROUND OF THE INVENTION

IL-15 is a cytokine which, like IL-2, has originally been described as a T cell growth factor (1). The two cytokines belong to the four α-helix bundle family, and their membrane receptors share two subunits (the IL-2R/IL-15Rβ and γ chains) responsible for signal transduction (2). The IL-2Rβ/γ complex is an intermediate affinity receptor for both cytokines. It is mainly expressed by most NK cells, and can be activated in vitro by nanomolar concentrations of IL-2 or IL-15.

High affinity IL-2 and IL-15 receptors, which are expressed for example on activated T cells, and which can be activated with picomolar concentrations of either cytokine, contain in addition their own, private, α chain (IL-2Rα and IL-15Rα) that confer cytokine specificity and enhance the affinity of cytokine binding (3).

Both cytokines play pivotal roles in innate and adaptive immunity. Whereas initial in vitro experiments have shown a large functional overlap (induction of the proliferation and cytotoxicity of activated lymphocytes and NK cells, co-stimulation of B cell proliferation and immunoglobin synthesis, chemoattraction of T cells) (1, 4-6), more recent experiments have indicated that the two cytokines exert complementary and even contrasting actions in viva. Whereas IL-2 or IL-2Rα knock out in mice was associated with autoimmune phenotypes with increased populations of activated T and B cells, IL-15 and IL-15Rα knock out resulted in specific defects in NK, NK-T, intraepithelial lymphocytes and memory CD8 T cells (7, 8). Furthermore, IL-2 promotes peripheral tolerance by inducing activation induced cell death (AICD), whereas IL-15 inhibits IL-2 mediated AICD (9), and, unlike IL-2, IL-15 is a survival factor for CD8 memory T cells (10).

In line with these observations, it has been suggested that the major role of IL-2 is to limit continuous expansion of activated T cells, whereas IL-15 is critical for the initiation of T cell division and the survival of memory T cells (11).

A novel mechanism of IL-15 transpresentation has been described, in which IL-15 and IL-15Rα are coordinately expressed by antigen-presenting cells (monocytes, dendritic cells), and IL-15 bound to IL-15Rα is presented in trans to neighboring NK or CD8 T cells expressing only the IL-15Rβ/γ receptor (12). IL-15 transpresentation as a co-stimulatory event occurring at the immunological synapse, now appears to be a dominant mechanism for IL-15 action in vivo (13, 14). It is suggested to play a major role in tumor immunosurveillance (15).

The IL-15Rα and IL-2Rα subunits form a sub-family of cytokine receptors in that they comprise at their N-terminal extracellular parts so called "sushi" structural domains (one in IL-15Rα, two in IL-2Rα) also found in complement or adhesion molecules (16). In both cases, these sushi domains have been shown to bear most of the structural elements responsible for the cytokine binding.

Whereas IL-2Rα alone is a low affinity receptor for IL-2 (Kd=10 nM), IL-15Rα binds IL-15 with high affinity (Kd=100 pM), Shedding of IL-2Rα by proteolysis is a natural mechanism that participates in the down regulation of lymphocyte activation. IL-2Rα is cleaved by Der p1, a major mite allergen, to inhibit Th1 cells and favor an allergic environment (17), and by tumor-derived metalloproteinases to suppress the proliferation of cancer-encountered T cells (18). The soluble IL-2Rα thus generated is a competitive inhibitor of IL-2 action in vitro. However, it remains a low affinity IL-2 binder, and it is not likely to efficiently participate in down regulation of IL-2 activity in vivo.

It has been recently shown that a soluble form of the human IL-15Rα can also be naturally released from IL-15Rα positive cells by a shedding process involving MMPs (19). In contrast to soluble IL-2Rα, this soluble IL-15Rα receptor was able to bind IL-15 with high affinity, and efficiently blocks proliferation driven through the high affinity IL-15Rα/β/γ signaling complex. This result was consistent with the concept of sIL-15Rα behaving, like its homolog sIL-2Rα, as an antagonist, and with inhibitory effects of mouse sIL-15Rα in vitro or in vivo (20, 21).

Here, the present inventors show that a fragment essentially consisting of the sushi domain of IL-15Ralpha (=IL-15Rα) has an opposite action. Such a fragment is able to enhance the binding, as well as the bioactivity of IL-15 through the IL-15Rbeta/gamma (=IL-15Rβ/γ) intermediate affinity receptor, without affecting those through the high affinity receptor. In addition, the present inventors describe fusion proteins which behave as potent super-agonists of the IL-15Rβ/γ complex. Such fusion proteins comprise an IL-15Rbeta/gamma binding entity, such as IL-15 (or a conservative fragment, agonist, mimetic thereof), fused by covalence e.g., by a flexible linker, to IL-15Rα or to an IL-15Ralpha fragment which has retained the sushi domain of IL-15Ralpha.

To the best of the inventors' knowledge, there is only one prior art which reports a stimulating effect for a compound comprising an IL-15Ralpha-related element, namely the commercially available form of soluble IL-15Ralpha.

It is the Giron-Michel et al. publication, which is entitled "*Membrane-bound and soluble IL-15/IL-15Ralpha complexes display differential signalling and functions on human haematopoietic progenitors*" (Blood, 1 Oct. 2005, Vol. 106, No. 7, pp. 2302-2310; pre-published online in June 2005).

The Giron-Michel et al. publication discloses that (see FIG. 7 of Giron-Michel et al.):

- recombinant IL-15 (rIL-15) induces a significant anti-apoptotic effect when it is used at a dose of 10 ng/ml, and that
- rIL-15 does not induce any significant anti-apoptotic effect at a dose of 0.1 ng/mL, but that
- rIL-15 at a dose of 0.1 ng/mL induces a significant anti-apoptotic effect when it is used with the commercially available form of soluble IL-15Ralpha.

The soluble IL-15Ralpha that is used by Giron-Michel et al. is the commercially available form of IL-15Ralpha (available from R&D Systems, under reference 147-IR). This soluble IL-15Ralpha is a modified form of soluble IL-15Ralpha, which lacks exon 3. The form of soluble IL-15Ralpha that is used by Giron-Michel et al. hence comprises the exon 2 encoded part of IL-15Ralpha, directly linked to the exon 4 encoded part of IL-15Ralpha, without comprising any exon 3 encoded part of IL-15Ralpha. The form of soluble IL-15Ralpha that is used by Giron-Michel et al. does therefore not correspond to a fragment of IL-15Ralpha, but to a modified form thereof.

The form of soluble IL-15Ralpha that is used by Giron-Michel et al. further comprises a Fc fragment (human IgG), linked thereto by covalence. A Fc fragment does not bind to IL-15Rbeta/gamma. The Giron-Michel et al. publication does therefore not disclose any compound wherein the soluble IL-15Ralpha form would be linked by covalence to an IL-15Rbeta/gamma binding entity.

The Giron-Michel et al. publication further discloses an anti-apoptotic effect, but does not disclose any effect on the proliferation and/or activation of IL-15Rbeta/gamma-positive cells. It can further be noted that the disclosed anti-apoptotic effect assay does not comprise any control samples which would contain (i) the soluble IL-15Ralpha-Fc fragment in the absence of rIL-15 or (ii) a soluble IL-15Ralpha without any Fc fragment. The disclosed anti-apoptotic effect therefore cannot be directly attributed to the IL-15Ralpha part of the compound that is used.

The Giron-Michel et al. publication does not further contain any hint to the sushi domain of IL-15Ralpha (nor to the hinge region that is absent from the soluble IL-15Ralpha form that is being used in this prior art), nor does it contain a hint to the IL-15beta/gamma signalling pathway.

The present invention describes for the first time the structural units which are necessary to, and especially advantageous for, the induction and/or stimulation of an IL-15 biological action, the specific triggering of the IL-15beta/gamma signalling pathways, and the induction and/or stimulation of the proliferation of NK and/or T cells. The present invention thereby represents a technical contribution over the prior art, which enables previously-unattained biological and medical applications.

It is therefore believed that, when analysed on an a priori basis, the Giron-Michel et al. publication does not teach the claimed invention to the person of ordinary skill in the art, and does not guide the skilled person to the claimed invention.

SUMMARY OF THE INVENTION

The present invention relates to the IL-15Rbeta/gamma signalling pathway, and to the induction and/or stimulation of the activation and/or proliferation of IL-15Rbeta/gamma-positive cells and/or prevention of apoptosis, such as NK and/or T cells.

The present invention demonstrates that the extracellular region of IL-15Ralpha can act as an agonist of IL-15 biological action, via the IL-15Rbeta/gamma signalling pathway. It notably demonstrates that it can stimulate and/or induce the proliferation and/or activation of IL-15Rbeta/gamma-positive cells and/or prevention of apoptosis, such as NK and/or T cells.

The present invention demonstrates that the minimal structural unit contained in this IL-15Ralpha extracellular region, that is required to exert such an agonist action, is the sushi domain of IL-15Ralpha extracellular region.

The present invention further demonstrates that the hinge and tail region of this IL-15Ralpha extracellular region significantly increase the efficiency of this agonist action.

The present invention further provides compounds which show a 30 to 150 fold increase in bioactivity, compared to wild-type IL-15, and which are even more potent than the simple association of IL-15 and soluble IL-15Ralpha sushi domain.

The present invention relates to the objects described in the detailed description section, and more particularly to those defined in the appended claims.

BRIEF DESCRIPTION OF THE DRAWINGS

FIG. 8 to 42 show amino acid and nucleic acid sequences, the SEQ ID of which are listed in Table 4 (table 4 is located after the bibliographic references, before the claims).

FIG. 8: human wild-type IL-15Ralpha cDNA (SEQ ID NO: 1).

FIG. 9: CDS of human wild-type IL-15Ralpha (SEQ ID NO: 2), and human wild-type IL-15Ralpha protein (SEQ ID NO: 3).

FIG. 10: CDS and amino acid sequences of the signal peptide of human wild-type IL-15Ralpha (SEQ ID NO: 4 and NO: 5), and of mature peptide (SEQ ID NO: 6, and NO: 7).

FIG. 11: nucleic acid sequences of exons 1 to 5 of human wild-type IL-15Ralpha (SEQ ID NO: 8-12).

FIG. 12: nucleic acid and amino acid sequences of the sushi domain of human wild-type IL-15Ralpha (SEQ ID NO: 13-14), and of a fragment of human wild-type IL-15Ralpha which comprises the sushi domain (SEQ ID NO: 15 and NO: 16).

FIG. 13: nucleic acid and amino acid sequences of a fragment of human wild-type IL-15Ralpha which comprises the sushi domain (SEQ ID NO: 17 and NO: 18).

FIG. 14: nucleic acid and amino acid sequences of the hinge of human wild-type IL-15Ralpha (SEQ ID NO: 19 and NO: 20), and of fragments of this hinge region.

FIG. 15: nucleic acid and amino acid sequences of fragments of human wild-type IL-15Ralpha which comprises the sushi domain and a fragment of hinge region (SEQ ID NO: 21-24).

FIG. 16: nucleic acid and amino acid sequences of fragments of human wild-type IL-15Ralpha which comprises the sushi domain and a fragment of hinge region (SEQ ID NO: 25-28).

FIG. 17: nucleic acid and amino acid sequences of a fragment of human wild-type IL-15Ralpha which comprises the sushi domain and the hinge region (SEQ ID NO: 29-30).

FIG. 18: nucleic acid and amino acid sequences of the region rich in glycosylation sites of human wild-type IL-15Ralpha (SEQ ID NO: 31-32).

FIG. 19: nucleic acid and amino acid sequences of the exon3-encoded part of the region rich in glycosylation sites of human wild-type IL-15Ralpha (SEQ ID NO: 33-34), and of a fragment of IL-15Ralpha which comprises the sushi domain, the hinge region, and the exon3-encoded part of the region rich in glycosylation sites (SEQ ID NO: 35-36).

FIG. 20: nucleic acid and amino acid sequences of a fragment of soluble extracellular region of human wild-type IL-15Ralpha (SEQ ID NO: 37-38).

FIG. 21: nucleic acid and amino acid sequences of a soluble extracellular region of human wild-type IL-15Ralpha (SEQ ID NO: 39-40).

FIG. 22: nucleic acid and amino acid sequences of a fragment of soluble, signal peptide deleted, extracellular domain of human IL-15Ralpha (SEQ ID NO: 41-42).

FIG. 23: nucleic acid and amino acid sequences of a soluble, signal peptide deleted, extracellular domain of human IL-15Ralpha (SEQ ID NO: 43-44).

FIG. 24: nucleic acid sequence of human wild-type IL-15 (SEQ ID NO: 45)

FIG. 25: amino acid sequence of human wild-type IL-15 precursor protein (SEQ ID NO: 46), nucleic acid and amino acid sequences of human wild-type mature IL-15 (SEQ ID NO: 47-48).

FIG. 26: nucleic acid and amino acid sequences of two flexible linkers (linker 20 SEQ ID NO: 49-50; linker 26 SEQ ID NO: 51-52).

FIG. 27: nucleic acid and amino acid sequences of Flag tag and Xa binding site (SEQ ID NO:53-56), of bovine preprolactine signal peptide (SEQ ID NO:57-58), and nucleic acid sequence of IL-15R and preprolactine Kozak sequences.

FIG. 28: nucleic acid and amino acid sequences of RLI (fusion protein of the invention; SEQ ID NO: 59-60). RLI fusion protein=signal peptide of IL-15Ralpha+Flag tag and Xa binding site+it+sushi+i+rd+eleven exon3-encoded aa+linker 26+human wild-type mature IL-15.

FIG. 29: nucleic acid and amino acid sequences of ILR (fusion protein of the invention; SEQ ID NO: 61-62). ILR fusion protein=signal peptide of bovine preprolactine+Flag tag and Xa binding site+human wild-type mature IL-15+linker 26+it+sushi+i+rd+eleven exon3-encoded amino acids.

FIG. 30: nucleic acid sequence of human wild-type IL-2 (SEQ ID NO: 63).

FIG. 31: nucleic acid and amino acid sequences of human wild-type mature IL-2 (SEQ ID NO: 64-65), and of a linker used to tag a sushi-containing fragment of IL-15Ralpha with IL-2.

FIG. 32: nucleic acid and amino acid sequences of a sushi-containing fragment of IL-15Ralpha, tagged with IL-2 (SEQ ID NO: 66-67).

FIG. 33: nucleic acid and amino acid sequences of a sushi-containing fragment of IL-15Ralpha (fragment of extracellular IL-15Ralpha), tagged with IL-2 (SEQ ID NO: 68-69).

FIG. 34: nucleic acid and amino acid sequences of *Mus musculus* IL-15Ralpha (SEQ ID NO: 72-73).

FIG. 35: nucleic acid and amino acid sequences of *Mus musculus* IL-15Ralpha extracellular region (SEQ ID NO: 74), sushi domain (SEQ ID NO: 75), hinge region (SEQ ID NO: 76), and tail region (SEQ ID NO: 77).

FIG. 36: nucleic acid and amino acid sequences of *Pan troglodytes* IL-15Ralpha (SEQ ID NO: 78-79).

FIG. 37: nucleic acid and amino acid sequences of *Pan troglodytes* IL-15Ralpha extracellular region (SEQ ID NO: 80), sushi domain (SEQ ID NO: 81), hinge region (SEQ ID NO: 82), and tail region (SEQ ID NO: 83).

FIG. 38: nucleic acid and amino acid sequences of *Rattus norvegicus* IL-15Ralpha (SEQ ID NO: 84-85).

FIG. 39: nucleic acid and amino acid sequences of *Rattus norvegicus* IL-15Ralpha extracellular region (SEQ ID NO: 86), sushi domain (SEQ ID NO: 87), hinge region (SEQ ID NO: 88), and tail region (SEQ ID NO: 89).

FIG. 40: nucleic acid sequence of the exon 3 of *Mus musculus* IL-15Ralpha (SEQ ID NO: 90), of *Pan troglodytes* IL-15Ralpha (SEQ ID NO: 91), and of *Rattus norvegicus* IL-15Ralpha (SEQ ID NO: 92).

FIG. 41: amino acid sequence of the exon 3 encoded part of human IL-15Ralpha (SEQ ID NO: 93), of *Mus musculus* IL-15Ralpha (SEQ ID NO: 94), of *Pan troglodytes* IL-15Ralpha (SEQ ID NO: 95), and of *Rattus norvegicus* IL-15Ralpha (SEQ ID NO: 96).

FIG. 42: amino acid sequence of the exon 2 encoded part of human IL-15Ralpha (SEQ ID NO: 24), of *Mus musculus* IL-15Ralpha (SEQ ID NO: 97), of *Pan troglodytes* IL-15Ralpha (SEQ ID NO: 98), and of *Rattus norvegicus* IL-15Ralpha (SEQ ID NO: 99).

DETAILED DESCRIPTION OF THE INVENTION

Figures 1A, 1B, 1C, 1D, 1E:
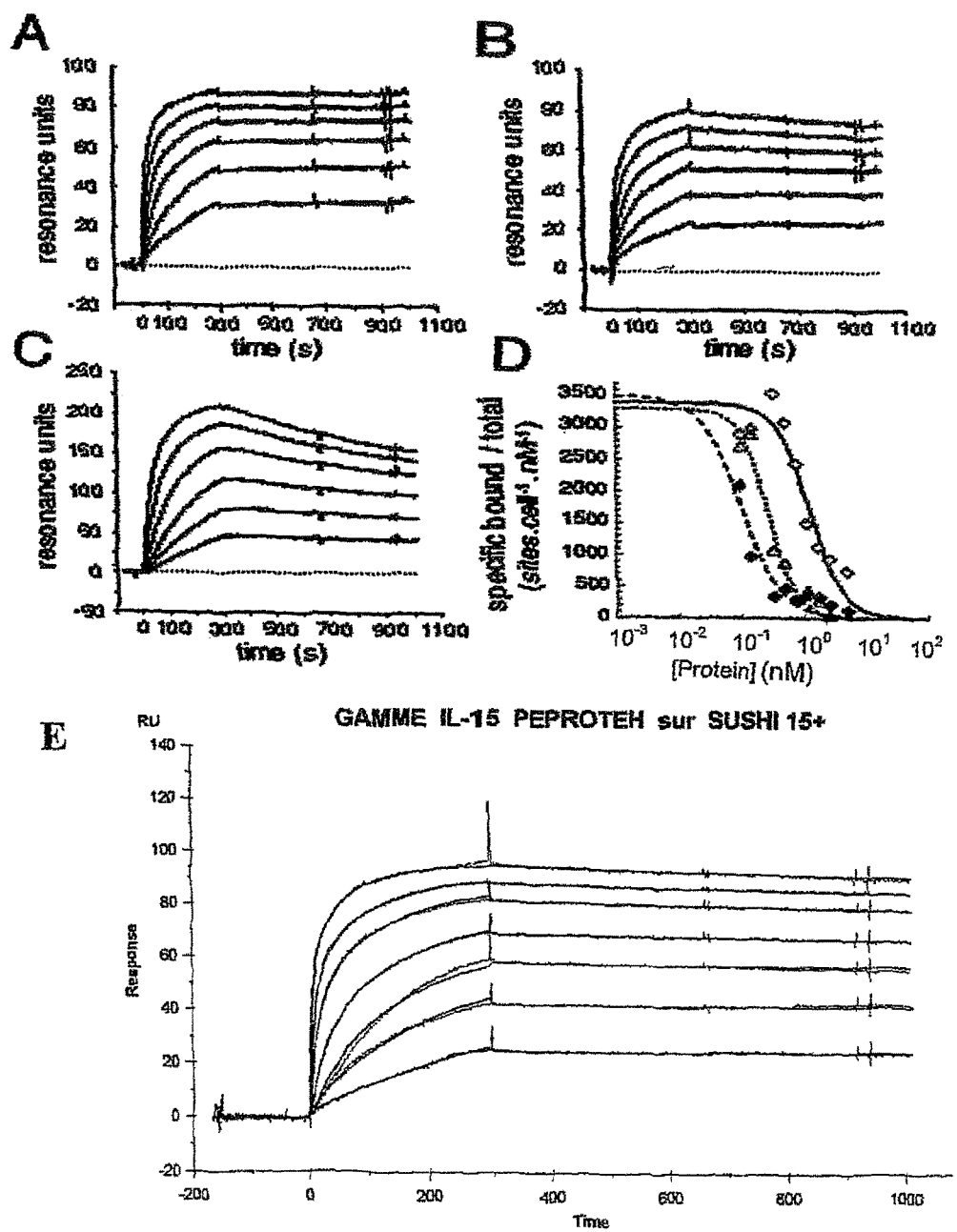
FIG. 1. Binding affinities of the various soluble IL-15Rα proteins for IL-15. SPR sensorgrams of the binding (association and dissociation phases) of increasing concentrations of rIL-15 (3.1, 6.2, 12.5, 25, 50 and 100 nM) to immobilized (A) sIL-15Rα-IL-2, (B) sIL-15Rα-sushi-IL-2 or (C) IL-15Rα-sushi. (D): Competition studies of sIL-15Rα-sushi (◇), sIL-15Rα-IL-2 (◆), or sIL-15Rα-sushi-IL-2 (△) with radioiodinated rIL-15 (200 pM) binding to TF-1 cells. SPR sensorgrams of the binding (association and dissociation phases) of increasing concentrations of rIL-15 (1, 2.5, 5, 10, 25, 50, 100 nM) to immobilized (E) sIL-15Rα-Sushi+.

The present invention relates to IL-15Ralpha, and to IL-15Ralpha fragments which comprise at least one IL-15Ralpha sushi domain.

The present invention relates to products, which can be intended for stimulating the IL-15Rbeta/gamma signalling pathway, to thereby induce and/or stimulate the activation and/or proliferation and/or prevention of apoptosis of IL-15Rbeta/gamma-positive cells, such as NK and/or T cells.

The present invention relates to isolated sushi-containing polypeptides, which contain the sushi domain that is comprised in the extracellular region of an IL-15Ralpha, i.e., it relates to the isolated fragment consisting of IL-15Ralpha extracellular region, and to sub-fragments thereof that have retained the sushi domain.

The sushi-containing polypeptides of the invention can be either linked by covalence, or not linked by covalence to at least one IL-15Rbeta/gamma binding entity.

The invention more particularly relates to a covalently-linked compound which comprises at least of such a sushi-containing polypeptide, directly or indirectly linked by covalence to at least one IL-15Rbeta/gamma binding entity.

Such a compound can have a 30 to 150 fold increase in bioactivity, compared to wild-type IL-15, and be more potent than the free association of IL-15 and soluble IL-15Ralpha sushi domain.

IL-15Rbeta/Gamma Binding Entity:

In addition to said at least one sushi-containing polypeptide, said covalently linked compound of the invention comprises at least one IL-15Rbeta/gamma binding entity.

Said IL-15Rbeta/gamma binding entity preferably is an IL-15, or an IL-15 fragment, mimetic, or agonist, wherein said IL-15 fragment, mimetic, or agonist has an affinity for binding to IL-15Rbeta/gamma that is not significantly lower than the one of native IL-15.

Said IL-15 can be any IL-15, e.g. a human IL-15, or a non-human mammalian IL-15, or a non mammalian IL-15.

Illustrative non-human mammalian IL-15 are monkey IL-15, or a murine IL-15 (e.g., mouse IL-15 of accession number NM_008357; rat IL-15 of accession number NM_013129), or a rabbit IL-15 (e.g., accession number DQ157152), a sheep IL-15 (e.g., accession number NM_001009734), or a pig IL-15 (e.g., accession number NM_211390). Illustrative non mammalian IL-15 is chicken (e.g., accession number NM_204571).

More preferably, said IL-15 is a human IL-15. Most preferably, the amino acid sequence of said human IL-15 is the sequence of SEQ ID NO: 48.

IL-15 does not bind IL-2Ralpha. In view of the biological and medical applications contemplated by the present invention, said IL-15 fragment, mimetic, or agonist preferably does not bind IL-2Ralpha.

The terms "agonist" and "mimetic" are herein given their ordinary meaning in the field.

A compound is termed IL-15 agonist when it induces a biological response that is of a similar or higher level than the one induced by native IL-15. Preferred agonists are those which induce an even higher level of biological response (super-agonist).

An IL-15 agonist typically has an affinity for binding to IL-15Ralpha and/or to IL-15Rbeta/gamma that is at least not significantly different from the one of native IL-15, and that is preferably significantly higher than the one of native IL-15.

A mimetic (or mimetope) of IL-15 refers to any compound that is able to mimic the biological actions of IL-15.

In the present invention, preferred IL-15 mimetics or agonists are those which are able to mimic the biological action of IL-15 through the IL-15Rbeta/gamma signalling pathway. Such a preferred IL-15 mimetic thus has the capacity of binding to the IL-15beta/gamma complex, and to thereby induce and/or stimulate the transduction of a biological signal through said IL-15Rbeta/gamma complex. Preferred IL-15 mimetics or agonists of the invention have an affinity for binding to IL-15Rbeta/gamma that is at least not significantly different from the one of native IL-15, and that is preferably significantly higher than the one of native IL-15. Appropriate agonists or mimetics have been described in e.g., the international PCT application PCT/EP2005/002367, filed on 10 Feb. 2005, in the name of INSERM.

Sushi-containing Polypeptide:

The amino acid sequence of said at least one sushi-containing polypeptide:
  is the amino acid sequence of the extracellular region of IL-15Ralpha (said extracellular region of IL-15Ralpha comprising an IL-15Ralpha sushi domain), or
  is the amino acid sequence of a fragment of the extracellular region of IL-15Ralpha, wherein said fragment has retained the sushi domain of said extracellular region of IL-15Ralpha, wherein said sushi domain is defined as beginning at the first exon 2 encoded cysteine residue (C1), and ending at the fourth exon 2 encoded cysteine residue (C4), residues C1 and C4 being both included in the sushi domain, or
  is a variant amino acid sequence that has retained each of the four cysteine residues (C1, C2, C3 and C4) of said sushi domain.

An alternative definition of the definition is that it begins at the first cysteine residue (C1) after the signal peptide, and ends at the fourth cysteine residue (C4) after the signal peptide.

Said variant amino acid sequence may comprise a conservative variant sequence of IL-15Ralpha sushi domain.

Such a conservative variant sequence of IL-15Ralpha sushi domain derives from the sequence of a parent sushi domain, by at least one deletion and/or at least one substitution and/or at least one addition of amino acid, but has retained the capacity of at least one of the following features:

i. increasing the affinity of IL-15 for IL-15Rbeta/gamma,
ii. inducing and/or stimulating an anti-apoptotic effect on beta/gamma-positive cells, and more particularly of beta/gamma-positive alpha-negative cells, such as naïve NK and/or T cells,
iii. enhancing the efficiency of IL-15 biological action through the IL-15Rbeta/gamma signalling pathway, i.e., inducing and/or stimulating the proliferation and/or activation of beta/gamma-positive cells, and more particularly of beta/gamma-positive alpha-negative cells, such as naïve or resting NK and/or T cells.

Preferably, said conservative variants have retained the feature described in iii. above.

Appropriate cell lines to assay the above mentioned features are IL-15Rbeta/gamma-positive IL-15Ralpha-negative cells. Illustrative of such cell lines is the cell line 32D, which can be transfected with a beta and a gamma chain (e.g., a human beta and a human gamma chain).

Alternatively, naïve or resting NK and/or T cells can be purified from a biological sample, such as a blood sample.

Preferably, said variant amino acid sequence is at least 85% identical to the amino acid sequence of such an IL-15Ralpha extracellular region, or of such a fragment of IL-15Ralpha extracellular region, over the entire length of this sequence of IL-15Ralpha extracellular region or of fragment of IL-15Ralpha extracellular region.

More preferably, this percentage of sequence identity is of at least 90%, still more preferably of at least 92%, most preferably of at least 95%, e.g., at least 96%, at least 97%, at least 98%, at least 99% or 100%.

Such variant amino acid sequences notably encompass the IL-15Ralpha polymorphisms which naturally occur within an animal species, as well as conservative variants which can be produced by the person of ordinary skill in the art.

IL-15Ralpha:

Exon 1 of IL-15Ralpha codes for the signal peptide of IL-15Ralpha.

Exon 2 of IL-15Ralpha codes for the sushi domain of IL-15Ralpha.

A 5' terminal part of exon 3 codes for region known as the hinge region of IL-15Ralpha.

The remaining part of exon 3, as well as the other extracellular exons (i.e., exon 4, exon 5, and a 5' part of exon 6 for human IL-15ralpha, as well as for most species) code for a region rich in glycosylation sites, also known as the tail region of IL-15Ralpha.

The remaining IL-15Ralpha exons (i.e., a 3' part of exon 6, as well as exon 7 for human IL-15ralpha, as well as for most species) code for the transmembranar and intracytoplasmic regions of IL-15Ralpha.

Advantageously, in view of the medical applications of the present invention, said IL-15Ralpha preferably is a human IL-15Ralpha.

The amino acid sequence of said human IL-15Ralpha most preferably is the sequence of human IL-15Ralpha sequence of SEQ ID NO: 3 (267 amino acids). The extracellular region of the human IL-15Ralpha of SEQ ID NO:3 has the amino acid sequence of SEQ ID NO:40 (1.209 of SEQ ID NO:3). The signal peptide deleted form of SEQ ID NO:40 is listed as SEQ ID NO:44 (31.209 of SEQ ID NO:3).

Some human alleles of IL-15Ralpha may have a Thr amino acid (amino acid t, coded by act, acc, aca, or acg), instead of a Asn amino acid (amino acid n, encoded by aat or aac) at position 182 of SEQ ID NO: 3. Such variants are naturally-occurring, and are functional.

In the present application, such allelic naturally-occurring variants of human IL-15Ralpha are meant as equivalent to the reference human IL-15Ralpha sequences of SEQ ID NO: 3 (amino acid sequence), and SEQ ID NO: 1 or NO: 2 (cDNA and CDS sequences), and to the reference human IL-15Ralpha sequences that directly derives therefrom, i.e., the extracellular region sequences of SEQ ID NO: 40 or NO:44 (amino acid sequences), and SEQ ID NO: 39 and NO:43 (CDS sequences).

The positions of the seven exons of the human IL-15Ralpha of SEQ ID NO:3 are as described in the following table 1.

In this respect, please note that the positions of exon 1 is 1 . . . 170, and that those of exon 2 is 171 . . . 365, as described in table 1 below, and that they are not 1 . . . 171 and 172 . . . 365, respectively, as declared in the sequence available under accession number U31628.

TABLE 1

| | Human IL-15Ralpha CDS (SEQ ID NO: 2) |
|---|---|
| Exon 1 | 1 . . . 170 |
| Exon 2 | 171 . . . 365 |
| Exon 3 | 366 . . . 464 |
| Exon 4 | 465 . . . 665 |
| Exon 5 | 666 . . . 698 |
| Exon 6 | 699 . . . 774 |
| Exon 7 | 775 . . . 883 |

The positions of the different regions and parts of the human IL-15Ralpha of SEQ ID NO: 3 is shown in table 2 below.

TABLE 2

| | | Human IL-15Ralpha | |
|---|---|---|---|
| | | CDS positions in SEQ ID NO: 1 | Amino acid positions in SEQ ID NO: 3 |
| Signal peptide | | 83 . . . 172 | 1 . . . 30 |
| IL-15Ralpha protein | | 173 . . . 883 | 31 . . . 267 |
| Parts of human IL-15Ralpha protein | Signal peptide | 83 . . . 172 | 1 . . . 30 |
| | Exon2-encoded part, which contains the sushi domain (it-sushi-i) | 173 . . . 364 | 31 . . . 94 |
| | Sushi domain (from C1 to C4) | 179 . . . 361 | 33 . . . 93 |
| | Hinge region (irdpalvhqrpapp) | 362 . . . 403 | 94 . . . 107 |
| | Region rich in glycosylation sites | 404 . . . 709 | 108 . . . 209 |
| | Transmembranar part | 710 . . . 766 | 210 . . . 228 |
| | intracytoplasmic part | 767 . . . 883 | 229 . . . 267 |

In the present application, the double-point symbol («. . .») placed between a first number and a second number describes an isolated sequence which is identical to the sequence extending from position "first number" to position "second number".

In the present application, when sequences are defined by "start" and "stop" positions, these start and stop positions are meant as included within the described sequence.

For some biological applications, such as preliminary testing, research, development, compound or cell screening, pre-clinical and clinical studies (including tests relating to pharmacological, toxicological, pharmacokinetic, or biological qualities, as well as "risk-benefit assessment" and safety related tests), non-human mammalian IL-15Ralpha can nevertheless be used.

Preferred non-human mammalian IL-15Ralpha notably comprise monkey IL-15Ralpha (e.g., a chimpanzee IL-15Ralpha), or a murine IL-15Ralpha (e.g., mouse IL-15Ralpha, rat IL-15Ralpha), or a rabbit IL-15Ralpha, or a pig IL-15Ralpha.

Illustrative IL-15Ralpha amino acid sequences of such non-human mammalian IL-15Ralpha are those encoded by the nucleic acid sequences available as accession number NM_008358 (*Mus musculus* IL-15Ralpha: nucleic acid sequence of SEQ ID NO: 72, amino sequence of SEQ ID NO:73), as accession number XM_521684 (*Pan troglodytes* IL-15Ralpha: nucleic acid sequence of SEQ ID NO: 78, amino sequence of SEQ ID NO:79), or as accession number XM_577598 (*Rattus norvegicus*: IL-15Ralpha: nucleic acid sequence of SEQ ID NO: 84, amino sequence of SEQ ID NO:85). See FIGS. 40, 41, 42 for illustrative human IL-15Ralpha exon 2 and exon 3 positions and sequences.

Extracellular Region of IL-15Ralpha:

The extracellular region of IL-15Ralpha is usually defined as the region of an IL-15Ralpha sequence that extends from its first N-terminal amino acid, to the last amino acid of the tail region (or region rich in glycosylation sites). As described in more details below, the tail region of an IL-15Ralpha sequence can be determined by the skilled person, e.g., through the help of software.

Said extracellular region of IL-15Ralpha is a human IL-15Ralpha extracellular region, or a non-human mammalian IL-15Ralpha extracellular region.

Among the amino acid sequences of human extracellular IL-15Ralpha regions, the amino acid sequence of the extracellular IL-15Ralpha region of SEQ ID NO: 40 is preferred.

The amino acid sequence of the human IL-15Ralpha extracellular region of SEQ ID NO: 40, is encoded by exons 1-5, and a small 5' part of exon 6 of human IL-15Ralpha.

Exon 1 of human IL-15Ralpha (SEQ ID NO: 8) codes for IL-15Ralpha signal peptide (nucleic acid sequence of SEQ ID NO: 4; amino acid sequence of SEQ ID NO: 5).

Exon 2 (SEQ ID NO: 9) comprises the sequence coding for the sushi domain of human IL-15Ralpha.

The last 3' codon of exon 2 codes for the first amino acid of the hinge region.

A 5' part of exon 3 (exon 3 of SEQ ID NO: 10) codes for the hinge region of human IL-15Ralpha.

The remaining 3' part of exon 3' plus exon 4 (SEQ ID NO: 11), exon 5 (SEQ ID NO: 12), and a 5' part of exon 6 (699 . . . 709 of SEQ ID NO:1) code for a region rich in glycosylation sites (also known as tail region).

The sequence of SEQ ID NO: 44 is the signal peptide deleted form of the IL-15Ralpha extracellular region of SEQ ID NO: 40. In the present invention signal peptides may be used, but are optional. Such a signal peptide can be an IL-15Ralpha signal peptide, or the signal peptide of another protein. Hence, a signal peptide deleted form of an IL-15Ralpha extracellular region (such as SEQ ID NO: 44) is directly equivalent to the complete IL15Ralpha extracellular sequence (such as SEQ ID NO: 40).

Illustrative of non-human mammalian IL-15Ralpha extracellular regions, are those which have the sequence of SEQ ID NO: 74 (1 . . . 204 of *Mus musculus* IL-15Ralpha), of SEQ ID NO: 80 (1 . . . 286 of *Pan troglodytes* IL-15Ralpha), of SEQ ID NO: 86 (1 . . . 182 of *Rattus norvegicus* IL-15Ralpha).

Sushi Domain:

The extracellular region of IL-15Ralpha or fragment thereof that defines said at least one sushi-containing polypeptide contains an IL-15Ralpha sushi domain.

The extracellular region of IL-15Ralpha contains a domain, which is known as the sushi domain (Wei et al. 2001, J. Immunol, 167:277-282).

The sushi domain of IL-15Ralpha has a beta sheet conformation.

It is coded by exon 2 of IL-15Ralpha. It begins at the first exon 2 encoded cysteine residue (C1), and ends at the fourth exon 2 encoded cysteine residue (C4).

When considering the IL-15Ralpha protein sequence in the standard N-terminal to C-terminal orientation, the sushi domain of IL-15Ralpha can be defined as beginning at the first cysteine residue (C1) after the signal peptide, and ending at the fourth cysteine residue (C4) after the signal peptide.

Residues C1 and C4 are both included in the sushi sequence.

Hence, when the identification of the sushi domain is made on a IL-15Ralpha sequence which is deleted from its signal peptide sequence (such as e.g., the sequence of SEQ ID NO: 44), the sushi domain is then defined as beginning at the first cysteine residue (starting from the N-terminal end of the protein), and ending at the fourth cysteine residue of this IL-15Ralpha sequence.

The IL-15Ralpha sushi domain can also be determined by analysis of the amino-acid sequence of IL-15Ralpha with appropriate software such as:

Prosite (http://us.expasy.org/prosite/),
InterProScan (http://www.ebi.ac.uk/InterProScan/),
SMART (http://elm.eu.org/).

The amino acid sequence of said sushi domain can be the amino acid sequence of a human IL-15Ralpha sushi domain, or of a non-human mammalian sushi domain.

Among the amino acid sequences of human IL-15Ralpha sushi domains, the amino acid sequence of the human IL-15Ralpha sushi domain of SEQ ID NO: 14 is preferred.

For example, the amino acid sequence of said fragment of extracellular region of human IL-15Ralpha can be the sequence of SEQ ID NO: 16 (it+human IL-15Ralpha sushi), or NO: 18 (t+human IL-15Ralpha sushi).

Illustrative of non-human mammalian IL-15Ralpha sushi domains, are the amino acid sequences of SEQ ID NO:75 (36 . . . -96 of *Mus musculus* IL-15Ralpha), of SEQ ID NO: 81 (13 . . . 73 of *Pan troglodytes* IL-15Ralpha), or of SEQ ID NO:87 (24 . . . 84 of *Rattus norvegicus* IL-15Ralpha).

Signal Peptide:

A signal peptide is a short (15-60 amino acids long) peptide chain that directs the post translational transport of a protein. Some signal peptides are cleaved from the protein by signal peptidase after the proteins are transported. Signal peptides may also be called targeting signals or signal sequences. The amino acid sequences of signal peptides direct proteins which are synthesized in the cytosol to certain organelles such as the nucleus, mitochondrial matrix, endoplasmic reticulum, chloroplast, and peroxisome.

The signal peptide of IL-1 Ralpha is a N-terminal sequence of about 29-33 amino acids, e.g., 30-32 amino acids. It begins at the first N-terminal amino acid residue of IL-15Ralpha. It is determined by analysis of the N-terminal amino-acid sequence of IL-15Ralpha with appropriate software such as:

SIGCLEAVE (http://bioweb.pasteur.fr/seqanal/interfaces/sigcleave.html),
InterProScan (http://www.ebi.ac.uk/InterProScan/),
SMART (http://elm.eu.org/).

The signal peptide of *Mus musculus* IL-15Ralpha is a N-terminal amino acid sequence of 32 amino acids (see accession number NP_032384; sig_peptide 1 . . . 32).

The signal peptide of human IL-15Ralpha, as shown in SEQ ID NO: 5, is a N-terminal amino acid sequence of 30 amino acids, which contains one cysteine residue.

Fragment of Exon 2 Encoded Part:

Exon 2 of IL-15Ralpha contains the sushi domain, i.e., the minimal structural unit that is required by the present invention.

Said fragment of IL-15Ralpha extracellular region can comprise (or can essentially consist of):
the part of IL-15Ralpha extracellular region, which is encoded by exon 2 of said IL-15Ralpha, or of
a fragment of such an exon 2 encoded part.

According to the present invention, said fragment of IL-15Ralpha extracellular region has to comprise at least one IL-15Ralpha domain. Hence, a fragment of an exon 2 encoded part can be any fragment thereof, provided that it still comprises the sushi domain (from residue C1 to residue C4).

For example, the exon 2 encoded part of the human extracellular region of SEQ ID NO:40 is the sequence extending from position 31 to position 94 (i.e., SEQ ID NO:24), i.e., it is:
it+sushi+i.

Fragments of this exon 2 encoded part are: t+sushi; it+sushi; t+sushi+i.

For example, said exon 2 encoded sequence can be:
the exon 2 encoded part of human extracellular IL-15Ralpha, which is the sequence of SEQ ID NO: 24,
the exon 2 encoded part of *Pan troglodytes* extracellular IL-15Ralpha, which is the sequence of SEQ ID NO: 98,
the exon 2 encoded part of *Mus musculus* extracellular IL-15Ralpha, which is the sequence of SEQ ID NO: 97,
the exon 2 encoded part of *Rattus norvegicus* extracellular IL-15Ralpha, which is the sequence of SEQ ID NO: 99.

Variants of such IL-15Ralpha extracellular region fragments are encompassed within the scope of the present invention.

Such variants notably include those which have conservative amino deletion and/or substitution and/or addition in their sequence.

A conservative variant sequence of an IL-15Ralpha extracellular region fragment derive from the sequence of a parent IL-15Ralpha extracellular region fragment, by at least one deletion and/or at least one substitution and/or at least one addition of amino acid, and has retained the capacity of at least one of the following features:
iv. increasing the affinity of IL-15 for IL-15Rbeta/gamma,
v. inducing and/or stimulating an anti-apoptotic effect on beta/gamma-positive cells, and more particularly of beta/gamma-positive alpha-negative cells, such as naive NK and/or T cells,
vi. enhancing the efficiency of IL-15 biological action through the IL-15Rbeta/gamma signalling pathway, i.e., inducing and/or stimulating the proliferation and/or activation of beta/gamma-positive cells, and more particularly of beta/gamma-positive alpha-negative cells, such as naïve or resting NK and/or T cells.

Preferably, said conservative variants have retained the feature described in iii. above.

Conservative variants notably comprise those which have an amino acid sequence that has an identity of at least 85% with the parent sequence, over the entire length of this parent sequence. Preferably, said percentage of identity is of at least 90%, still more preferably of at least 92%, most preferably of at least 95%, e.g., at least 96%, at least 97%, at least 98%, at least 99% or 100%.

For example, starting from the above-mentioned exon 2 encoded part of SEQ ID NO: 40, it will be apparent to the skilled person that i+sushi, i+sushi+t, i+sushi+i, it+sushi+t are conservative variants, which are technically equivalent to the parent fragment.

Fragment of Exon 2-3 Encoded Part:

According to a very advantageous embodiment of the present invention, said fragment of IL-15Ralpha extracellular region may further comprise at least one amino acid from the sequence that is encoded by exon 3 of said IL-15Ralpha.

Said fragment of IL-15Ralpha extracellular region may thus comprise, or consist of:
the part of IL-15Ralpha extracellular region, which is encoded by exons 2 and 3 of said IL-15Ralpha, or of
a fragment of such an exon 2-3 encoded part, which has retained said sushi domain.

Exon 3 of the human IL-15Ralpha of SEQ ID NO: 3 (i.e., of the human extracellular region of SEQ ID NO: 40) is the nucleic acid sequence of SEQ ID NO: 10. The exon 3 encoded part of SEQ ID NO: 3 is the sequence of SEQ ID NO: 93, i.e., the 95 . . . 127 sequence part of SEQ ID NO: 3 or of SEQ ID NO: 40 (i.e., the amino acid sequence which extends from position 95 to position 127 of the human IL-15Ralpha sequence of SEQ ID NO: 3 or NO: 40, positions 95 and 127 being both included).

For example, said exon 3 encoded sequence can be:
the exon 3 encoded part of human extracellular IL-15Ralpha, which is the sequence of SEQ ID NO: 93,
the exon 3 encoded part of *Pan troglodytes* extracellular IL-15Ralpha, which is the sequence of SEQ ID NO: 95,
the exon 3 encoded part of *Mus musculus* extracellular IL-15Ralpha, which is the sequence of SEQ ID NO: 94,
the exon 3 encoded part of *Rattus norvegicus* extracellular IL-15Ralpha, which is the sequence of SEQ ID NO: 96.

A fragment of an exon 3 encoded part can be a fragment of only one amino acid, preferably of at least two amino acids, more preferably of at least three amino acids, still more preferably of at least four amino acids, most preferably of at least five amino acids.

The inventors demonstrate that an exon 3 encoded part of IL-15Ralpha, or a fragment thereof, advantageously increases the affinity and the efficiency of the resulting compound, in terms of IL-15Rbeta/gamma signal transduction, and of IL-15Rbeta/gamma-positive cell proliferation and activation.

When the sushi-containing polypeptide is intended for the production of a fusion protein, the skilled person may prefer limiting the number of exon 3 amino acid to the optimum number, i.e., to the number of amino acids which represents a fair balance between the increase in affinity and efficiency on the one hand, and the increase in molecular size and conformation difficulties on the other hand.

Hence, the skilled person may find advantageous to limit the number of exon 3 encoded amino acids that are added to said IL-15Ralpha sushi domain to a number of 30, preferably of 25, more preferably of 20, still more preferably of 18, most preferably of 17, e.g., of 17, 16, 15, 14, 13, 12, 11, 10, 9, 8, 7, 6.

Most preferred numbers of exon 3 encoded amino acids therefore are those of the intervals that result from the combination of each of the above-mentioned inferior limits to each of the above-mentioned superior limits.

Illustrative of preferred fragments of exon 3 encoded part are all fragments which derive from the exon 3 encoded part of the human IL-15Ralpha of SEQ ID NO:3 (or of SEQ ID NO:40), i.e., the part extending from position 95 to position 127, positions 95 and 127 being both included (in others words: sequence 95 . . . 127 of SEQ ID NO:3 or NO:40).

A preferred compound of the invention hence comprises at least one sushi-containing polypeptide which, in addition to said sushi domain, comprise at least one amino acid from the sequence extending from position 95 to position 127 of SEQ ID NO:3 (positions 95 and 127 being both included). It most preferably comprises:

a preferred number of such amino acids (i.e., "at least two amino acids, more preferably of at least three amino acids, still more preferably of at least four amino acids, most preferably of at least five amino acids"), or a most preferred number of such amino acids (i.e., any combination resulting from "at least two amino acids, more preferably of at least three amino acids, still more preferably of at least four amino acids, most preferably of at least five amino acids", and "of at most 30, preferably of at most 25, more preferably of at most 20, still more preferably of at most 18, most preferably of at most 17, e.g. of 17, 16, 15, 14, 13, 12, 11, 10, 9, 8, 7, 6").

Hence, said fragment of IL-15Ralpha extracellular region advantageously comprises the part of IL-15Ralpha extracellular region, which is encoded by exon 2 of said IL-15Ralpha, or a conservative variant thereof as above-defined, and further comprises at least one amino acid from the sequence encoded by exon 3 of said IL-15Ralpha.

More particularly, said fragment of IL-15Ralpha extracellular region can comprise (or can essentially consist of):

the part of IL-15Ralpha extracellular region, which is encoded by exons 2 and 3 of said IL-15Ralpha, or a conservative variant thereof, or the part of IL-15Ralpha extracellular region, which is encoded by exon 2 of said IL-15Ralpha, and a fragment of the part of IL-15Ralpha extracellular region, which is encoded by exon 3 of said IL-15Ralpha.

Still more particularly, said fragment of IL-15Ralpha extracellular region can comprise (or can essentially consist of):

the part of IL-15Ralpha extracellular region, which is encoded by exons 2 and 3 of said IL-15Ralpha, or a conservative variant thereof, or a fragment of such an exon 2-3 encoded part or of such an exon 2-3 encoded variant, with the implied proviso that such a fragment has retained the sushi domain.

The above-given definition of conservative variants applies mutatis mutandis to a conservative variant of an exon 2-3 encoded part, i.e., it is a sequence which derives from a parent exon 2-3 encoded sequence, by at least one deletion and/or at least one substitution and/or at least one addition of amino acid, and has retained the capacity of at least one of the following features:

vii. increasing the affinity of IL-15 for IL-15Rbeta/gamma, viii. inducing and/or stimulating an anti-apoptotic effect on beta/gamma-positive cells, and more particularly of beta/gamma-positive alpha-negative cells, such as naïve NK and/or T cells, ix. enhancing the efficiency of IL-15 biological action through the IL-15Rbeta/gamma signalling pathway, i.e., inducing and/or stimulating the proliferation and/or activation of beta/gamma-positive cells, and more particularly of beta/gamma-positive alpha-negative cells, such as naïve or resting NK and/or T cells.

Preferably, said conservative variants have retained the feature described in iii. above.

Conservative variants notably comprise those which have an amino acid sequence that has an identity of at least 85% with the parent sequence, over the entire length of this parent sequence. Preferably, said percentage of identity is of at least 90%, still more preferably of at least 92%, most preferably of at least 95%, e.g., at least 96%, at least 97%, at least 98%, at least 99% or 100%.

Hinge Region (Located after the Sushi Domain, Encoded by a 3' Part of Exon 2 and a 5' Part of Exon 3, or by a 5' Part of Exon 3):

The inventors demonstrate that the hinge region of IL-15Ralpha is more particularly involved in this increase in signal transduction efficiency, and in this increase in IL-15Rbeta/gamma-positive cell proliferation and activation.

Hence, according to a very advantageous embodiment of the present invention, said fragment of IL-15Ralpha extracellular region can, in addition to said IL-15Ralpha sushi domain, further comprise an IL-15Ralpha hinge region, or a fragment of IL-15Ralpha hinge region.

An IL-15Ralpha hinge region is defined as the amino acid sequence that begins at the first amino residue after the sushi domain (when considering the IL-15Ralpha sequence in the standard N-terminal to C-terminal orientation), and that ends at the last amino acid residue before the first potential site of glycosylation.

The positions of potential glycosylation sites are determined using the software NetOGlyc (http://www.cbs.dtu.dk/services/NetOGlyc-3.1/) for the identification of potential O-glycosylation sites, and the software NetNGlyc (http://www.cbs.dtu.dk/services/NetNGlyc/) for the identification of potential N-glycosylation sites.

In a human IL-15Ralpha, the amino acid sequence of the hinge region consists of the fourteen amino acids which are located after the sushi domain of this IL-15Ralpha, in a C-terminal position relative to said sushi domain, i.e., said IL-15Ralpha hinge region begins at the first amino acid after said (C4) cysteine residue, and ends at the fourteenth amino acid (counting in the standard "from N-terminal to C-terminal" orientation).

In the human IL-15Ralpha of SEQ ID NO: 3 (the extracellular region of which being the sequence of SEQ ID NO:40), the amino acid sequence of said human IL-15Ralpha hinge region is the sequence of SEQ ID NO: 20. It contains one amino acid encoded by exon 2 (amino acid i), and thirteen amino acids encoded by exon 3.

In the *Mus musculus* IL-15Ralpha of SEQ ID NO:73, the hinge region has the sequence of SEQ ID NO:76.

In the *Pan troglodytes* IL-15Ralpha of SEQ ID NO:79, the hinge region has the sequence of SEQ ID NO:82.

In the *Rattus norvegicus* IL-15Ralpha of SEQ ID NO:85, the hinge region has the sequence of SEQ ID NO:88.

Said at least one sushi-containing polypeptide may thus comprise the sushi domain of SEQ ID NO: 75 and the hinge region of SEQ ID NO: 76 (*Mus musculus*), the sushi domain of SEQ ID NO: 81 and the hinge region of SEQ ID NO: 82 (*Pan troglodytes*), or the sushi domain of SEQ ID NO: 87 and the hinge region of SEQ ID NO: 88 (*Rattus norvegicus*).

Advantageously, said at least one sushi-containing polypeptide preferably comprises the human sushi domain of SEQ ID NO: 14, and the human hinge region of SEQ ID NO: 20 (for example, SEQ ID NO: 16 or NO: 18, followed by the hinge region of SEQ ID NO: 20). Preferably, said at least one sushi-containing polypeptide comprises, or is, a polypeptide of SEQ ID NO: 30 (it+sushi+hinge), optionally deleted from its N-terminal i and/or t.

Said fragment of IL-15Ralpha extracellular region can alternatively comprise, in addition to the sushi domain, a fragment of hinge region. By fragment of a hinge region, it is herein meant any fragment thereof, down to only one amino acid of said hinge region. Preferably, a fragment of hinge region comprises at least two amino acids, more preferably at least three amino acids.

A fragment of IL-15Ralpha hinge region can therefore be a fragment of 1 (e.g., amino acid i), 2 (e.g., amino acids ir), 3 (e.g., amino acids ird), 4 (e.g., amino acids irdp), 5 (e.g., amino acids irdpa), 6 (e.g., amino acids irdpa), 7 (e.g., amino acids irdpal), 8 (e.g., amino acids irdpalv), 9 (e.g., amino acids irdpalvh), 10, 11, 12, 13 or 14 amino acids.

Advantageously, said at least one sushi-containing polypeptide preferably comprises the human sushi domain of SEQ ID NO: 14, and a fragment of the hinge region of SEQ ID NO: 20.

The amino acid sequence of said fragment of IL-15Ralpha hinge region comprises, or is, i, or ir, or ird.

The sushi-containing polypeptide of SEQ ID NO: 22, 24, and 26 comprises the sushi domain of SEQ ID NO: 14, and the "i" fragment of the hinge region of SEQ ID NO: 20.

The sushi-containing polypeptide of SEQ ID NO: 28 comprises the sushi domain of SEQ ID NO: 14, and the "ird" fragment of the hinge region of SEQ ID NO: 20.

Said amino acid sequence of a fragment of human IL-15Ralpha extracellular region may more particularly comprise, in addition to said sushi domain and hinge region amino acid sequences:

the amino acid sequence of a region of extracellular IL-15Ralpha which is known as the region rich in glycosylation sites, or as the tail region, or a fragment thereof.

Region Rich in Glycosylation Sites, Also Known as Tail Region (Encoded by a 3' Part of Exon 3, by the Other Extracellular Exons):

The region rich in glycosylation sites of IL-15Ralpha is a region which comprises several potential glycosylation sites. It is sometimes referred to as the "tail" region of IL-15Ralpha. It starts at the first amino acid residue after the hinge region (when considering the sequence in the standard "N-terminal to C-terminal" orientation), and ends at the last amino acid residue before the transmembranar region of IL-15Ralpha. It comprises several potential glycosylation sites.

The transmembranar domain is determined by the analysis of the amino-acid sequence of IL-15Ralpha with appropriate software such as: TopPred (http://biowed.pasteur.fr/seganal/interfaces/topred.html), TMpred (http://www.ch.embnet.org/software/TMPRED_form.html).

The tail region of human IL-15Ralpha comprises several O-glycosylation sites, and one N-glycosylation site.

The human IL-15Ralpha tail region of SEQ ID NO: 32 is encoded by a 3' part of exon 3, and by exon 4, exon 5, and a 5' part of exon 6 of said human IL-15Ralpha.

Illustrative of the tail of non-human mammalian IL-15Ralpha extracellular region, are the amino acid sequences of SEQ ID NO: 77 (*Mus musculus*), of SEQ ID NO: 83 (*Pan troglodytes*), or of SEQ ID NO: 89 (*Rattus norvegicus*).

By fragment, or sub-fragment, of a region rich in glycosylation sites (or fragment or sub-fragment of tail region), it is herein meant any fragment, or sub-fragment, of said region, down to only one amino acid of said region. Preferably, said fragment, or sub-fragment, comprises at least two amino acids, more preferably at least three amino acids.

Said amino acid sequence of a fragment of IL-15Ralpha extracellular region may hence comprise:
the exon 3 encoded part of the region rich in glycosylation sites of IL-15Ralpha, or
a fragment of such an exon 3 encoded part.

A preferred amino acid sequence for the exon 3 encoded part of the region rich in glycosylation sites of human IL-15Ralpha is the amino acid sequence of SEQ ID NO: 34. A sushi-containing polypeptide of the invention advantageously is the polypeptide of SEQ ID NO: 36 (optionally deleted from the first C-terminal i and/or t amino acids).

As previously indicated, any fragment of exon 3 encoded part that the skilled person find appropriate can be used, e.g., any fragment of at least one amino acid, preferably of at least two amino acids, more preferably of at least three amino acids.

Extracellular Exons, Other than Exons 1, 2, 3:

The extracellular IL-15Ralpha exons, other than exons 1, 2, 3, code for a C-terminal fragment of the tail region.

Such parts, or fragments thereof, may further enhance the efficiency of the compounds of the invention.

Said amino acid sequence of a fragment of IL-15Ralpha extracellular region may hence further comprise a part of extracellular IL-15Ralpha which is encoded by exon 4, and/or exon 5 and/or exon 6, or any fragment of such a part.

Exon positions of the human IL-15Ralpha of SEQ ID NO: 3 are herein shown in the above table 1.

Illustrative of amino acid sequences of such sushi-containing polypeptides are the sequences of SEQ ID NO: 38, or the signal peptide deleted SEQ NO: 42, or the signal peptide deleted SEQ NO: 44.

Illustrative sushi-containing polypeptides are those which contain the sushi domain, the hinge region and the complete tail of IL-15Ralpha (e.g., the human IL-15Ralpha tail of SEQ ID NO: 32; the *Pan troglodytes* IL-15Ralpha tail of SEQ ID NO: 83; the *Mus musculus* IL-15Ralpha tail of SEQ ID NO: 77; the *Rattus norvegicus* IL-15Ralpha tail of SEQ ID NO: 89), and optionally a signal peptide.

IL-15 Biological Action:

At the organism or cellular level, a product of the invention is characterized in that it induces and/or stimulates IL-15 biological action. It stimulates those biological actions which are exerted by, inducible with, or stimulated by, IL-15, IL-15 mimetics, and/or IL-15 agonists.

The products of the invention (i.e., the sushi-containing polypeptides described herein, in isolated form, and more particularly the compounds of the invention) may thus be regarded as an agonist of IL-15 biological action.

One special and advantageous characterizing feature of a product of the invention is that it is capable of inducing and/or stimulating the IL-15Rbeta/gamma signaling pathway, and more particularly of stimulating IL15 biological action through the IL-15Rbeta/gamma signaling pathway.

At the molecular level, a product of the invention is thus more particularly characterized in that it increases the efficiency of the IL-15Rbeta/gamma signaling pathway. It sensitizes those cells which express the IL-15Rbeta/gamma complex to the action of IL-15. Still more particularly, it sensitizes those cells which express the IL-15Rbeta/gamma complex, but do not express IL-15Ralpha (IL-15Rβ/γ+IL-15Rα⁻ cells), to the action of IL-15.

Some of the products of the invention are IL-15Rbeta/gamma specific, in the sense that they do not enhance the efficiency of the IL-15Ralpha/beta/gamma signaling pathway. It is notably the case of the ILR fusion protein of the invention (amino acid sequence of SEQ ID NO: 62; and nucleic acid sequence of SEQ ID NO: 61).

Some other products of the invention are capable of enhancing the efficiency of both the IL-15Rbeta/gamma and the IL-15Ralpha/beta/gamma signaling pathways. It is notably the case of the RLI fusion protein of the invention (amino acid sequence of SEQ ID NO: 60; and nucleic acid sequence of SEQ ID NO: 59).

The invention also shows that the sushi domain of IL-15Rα is crucial for transpresentation. It thereby gives access to particularly useful and particularly needed medical applications in the field of cancer treatment and/or palliation and/or prevention, by vaccine administration, such as e.g. administration of a composition which comprises at least one compound containing at least one IL-15Ralpha sushi domain.

IL-15 is a cytokine which stimulates the proliferation and/or survival of lymphocytes (such as T cells, CD8+ T cells, NK cells, dendritic cells) and/or their activity against tumour cells.

IL-15 is involved in the cross-talk between accessory cells and lympoid cells.

It is essential in peripheral tissues for the development of NK cells, NKT cells, and CD8+ memory T cells.

It is the most powerful physiological factor able to induce the differentiation of CD34+ hematopoietic cells.

Said IL-15 biological action is a biological action exerted by, inducible by, or stimulated by IL-15, and/or IL-15 mimetics and/or IL-15 agonists.

The skilled person can choose any IL-15 biological response that he/she finds appropriate or convenient to assess or monitor.

Preferably, said IL-15 biological action is a biological action exerted by, inducible by, or stimulated by IL-15 and/or IL-15 mimetics and/or IL-15 agonists, on IL-15Rbeta/gamma+ IL-15Ralpha− cells.

A typical IL-15 biological response is the proliferation of, and/or the activation of, IL-15 sensitive cells.

Examples of IL-15 sensitive cells are T cells, CD8+ T cells, NK cells, dendritic cells, whose proliferation are induced and/or stimulated upon addition of IL-15 and/or IL-15 mimetics and/or IL-15 agonists, and/or whose activation is induced and/or stimulated upon addition of IL-15 and/or IL-15 mimetics and/or IL-15 agonists (e.g., induction of an anti-tumour activity).

Such cells can e.g., be collected from a mammalian organism.

Other examples of IL-15 sensitive cells comprise known cells lines, such as the CTL-L2 mouse cytotoxic T lymphoma cell line (ATCC accession number TIB-214), or TF1-beta cells.

TF1-beta cells are available by transfection of TF-1 cells with beta chains.

TF-1 cells are available from the American Type Culture Collection ATCC; P.O. Box 1549; Manassas, Va. 20108; U.S.A.; cf. http://www.lgcpromochem.com/atcc/ under ATCC accession number CRL-2003. IL-2R beta recombinant retroviruses can then be used to infect TF-1 cells to generate TF-1β after selection in medium containing G418.

Preferably, said IL-15 sensitive cells are IL-15Rbeta/gamma+ IL-15Ralpha− cells. Examples of IL-15Rbeta/gamma+ IL-15Ralpha− cells include the human Mo-7 cell line, or resting NK and/or T cells.

Resting NK and/or T cells are available to the skilled. They can, e.g., be obtained by purification of a cell sample, such as a blood sample.

Resting NK and T cells can be isolated from the blood of healthy adult donors as follow: whole blood is centrifuged at high speed to obtain a buffy coat. This buffy coat is centrifuged on a density gradient (Histopaque, Sigma) to obtain peripheral blood lymphocytes. Resting NK cells are then isolated from peripheral blood lymphocytes using a NK cell negative isolation kit (Dynal, Biotech ASA, Oslo, Norway). Alternatively, resting T cells are isolated from peripheral blood lymphocytes using a T cell negative isolation kit (Dynal, Biotech ASA, Oslo, Norway).

Other examples of IL-15Rbeta/gamma+ IL-15Ralpha− cells include IL-15Ralpha− cells, which are transformed or transfected by IL-15Rbeta/gamma, preferably by a human IL-15Rbeta/gamma.

For example, the murine 32D cell line (ATCC CRL-11346) can be transfected by beta and gamma chains, preferably with human and gamma chains.

Beta chains (i.e., IL-15Rbeta chains, also referred to as IL-2Rbeta chains) are known by, and available to, the skilled person. Among beta chains, human beta chains are preferred.

Beta chain templates are available from RNA of HuT102 (ATCC TIB-162) by RT-PCR using the proofreading polymerase Pfu (Stratagène n° 600390) and 5'GAGAGACTG-GATGGACCC 3' as sense primer (SEQ ID NO: 70), and 5' AAGAAACTAACTCTTAAAGAGGC3' as anti-sense primer (SEQ ID NO: 71) according to human IL-2R beta sequence (NCBI accession number K03122). The PCR product is efficiently cloned using the Zero Blunt PCR Cloning Kit (In Vitrogen cat n° K2700-20) or the TOPO XL PCR cloning kit (in Vitrogen cat n° K4750-10). The cDNA for IL-2R beta gene is then subcloned into the multiple cloning site of the pLXRN retrovirus expression vector of the Pantropic Retroviral Expression System (BD Biosciences Clontech n° 631512) and transfected into GP2-293 cells, as described in the kit to generate recombinant retroviruses.

Gamma chains (i.e., IL-15Rgamma chains, also referred to as IL-2Rgamma chains) are known by, and available to, the skilled person. Among gamma chains, human gamma chains are preferred.

Gamma chain templates are available from RNA of TF1 (ATCC CRL 2003) or HuT 102 (ATCC TIB 162) by RT-PCR using the proof-reading polymerase Pfu and 5' GAAGAG-CAAG CGCCATGTTG 3' (SEQ ID NO:100) as sense primer and 5' TCAGGTTTCAGGCTTTAGGG 3' as anti-sense primer (SEQ ID NO:101) according to human interleukin-2 receptor gamma sequence (NCBI Accession number D 11086). The PCR product is efficiently cloned using the Zero Blunt PCR Cloning Kit or the TOPO XL PCR cloning kit. The cDNA for IL-2Rγ gene is then subcloned into pcDNA 3.1/HYGRO (in Vitrogen) to generate a pcDNA IL-2Rγ/HYGRO plasmid.

IL-2R beta recombinant retroviruses can be used to infect 32D cells to generate 32Dβ after selection in medium containing G418. The pcDNA IL-2Rγ/HYGRO plasmid can then be transfected into 32Dβ cells by electroporation to generate 32Dβγ after selection in medium containing hygromycin.

The skilled person may alternatively choose to assess or monitor an IL-15 biological response that is more downstream in the signalling pathway, such as activation of a tyrosine kinase (e.g., Jak-1/Jak-3; Lck; Syk), activation of a MAP kinase, or a nuclear translocation event (e.g., translocation of phosphorylated Stat-3 and/or Stat-5). Said IL15 biological response may then be an acellular response.

Additional Elements (Signal Peptide, Molecular Tag, Proteolytic Site, Etc.):

A compound of the invention may comprise a signal peptide. This signal peptide can be directly or indirectly linked to said at least one sushi-containing polypeptide or to said at least one IL-15Rbeta/gamma binding entity. Said signal peptide can be linked to said compound by covalence.

Signal peptides facilitate secretion of proteins from cells. This signal peptide may, e.g., be the signal peptide of an IL-15Ralpha, such as a human IL-15Ralpha (such as the signal peptide of human IL-15Ralpha which is of sequence SEQ ID NO: 5) directly or indirectly linked to said fragment, or the signal peptide of another protein (such as the signal peptide of bovine preprolactine of SEQ ID NO: 58), directly or indirectly linked to said fragment. Exemplary signal peptides are:
- the peptide encoded by the leader sequence of human wild-type IL-15Ralpha (SEQ ID NO: 4), i.e., the first 30 N-terminal amino acids of human wild-type IL-15Ralpha (SEQ ID NO: 5), or
- the peptide encoded by the leader sequence of bovine preprolactine (SEQ ID NO: 57), i.e., the first 31 N-terminal amino acids of bovine preprolactine (SEQ ID NO: 58).

Other signal peptides which are found appropriate by the skilled person may also be employed. Furthermore, certain nucleotides in the IL-15 leader sequence can be altered without altering the amino acid sequence. Additionally, amino acid changes that do not affect the ability of the sequence to act as a signal peptide can be made.

A sushi-containing polypeptide of the invention may be directly linked to the signal peptide of the IL-15Ralpha from which it derives. Such a sushi-containing polypeptide may nevertheless be:
- indirectly linked to such a "native" signal peptide, or
- directly or indirectly linked to a signal peptide which is not from the IL-15Ralpha from which said sushi-containing polypeptide derives.

A compound of the invention may further comprise at least one molecular tag and/or at least one proteolytic site.

For example, a molecular tag and/or a proteolytic site can be located between the signal peptide and the sushi domain, or between the signal peptide and the IL-15Rbeta/gamma binding entity. Said molecular tag and/or proteolytic site may be directly or indirectly linked to said at least one sushi-containing polypeptide, or to said IL-15Rbeta/gamma binding entity.

Examples of molecular tags notably comprise FLAG® tags.

Examples of proteolytic sites notably comprise Xa binding sites.

The FLAG® (a registered trademark) octapeptide (Hopp et al., Bio/Technology 6:1204, 1988) does not alter the biological activity of fusion proteins, is highly antigenic, and provides an epitope reversibly bound by a specific monoclonal antibody, enabling rapid detection and facile purification of the expressed fusion protein. The FLAG® sequence is also specifically cleaved by bovine mucosal enterokinase at the residue immediately following the AspLys pairing. Fusion proteins capped with this peptide may also be resistant to intracellular degradation in E. coli. A murine monoclonal antibody that binds the FLAG® sequence has been deposited with the ATCC under accession number HB 9259. Methods of using the antibody in purification of fusion proteins comprising the FLAG® sequence are described in U.S. Pat. No. 5,011,912.

Examples of sequences coding for a Flag epitope and a factor Xa binding site comprise those of SEQ ID NO: 53 and NO: 55 (amino acid sequences of SEQ ID NO: 54 and NO: 56, respectively).

Amino Acids:

In the context of the present invention, 'amino acid residue' means any amino acid residue known to those skilled in the art (see e.g.: Sewald et al., 2002 (42); IUPAC nomenclature under http://www.chem.qmul.ac.uk/iupac/AminoAcid/). This encompasses naturally occurring amino acids (including for instance, using the three-letter code, Ala, bAla, Arg, Asn, Asp, Cys, Gln, Glu, Gly, His, Ile, Leu, Lys, Met, Phe, Pro, Ser, Thr, Trp, Tyr, Val), as well as rare and/or synthetic amino acids and derivatives thereof (including for instance Aad, Abu, Acp, Ahe, Aib, Apm, Dbu, Des, Dpm, Hyl, MeLys, MeVal, Nva, HAO, NCap, Abu, Aib, MeXaa and the like (see e.g.: (Müller et al., 1993; Aurora et al., 1998; Obrecht et al., 1999; Maison et al., 2001; Formaggio et al., 2003; Nowick et al., 2003; (43-48). Said amino acid residue or derivative thereof can be any isomer thereof, especially any chiral isomer, e.g., the L- or D-isoform.

By amino acid derivative, we hereby mean any amino acid derivative as known in the art (see e.g.: Sewald et al., 2002 (42); IUPAC nomenclature under http://www-.chem.qmul.ac.uk/iupac/AminoAcid/).

For instance, amino acid derivatives include residues derivable from natural amino acids bearing additional side chains, e.g. alkyl side chains, and/or heteroatom substitutions. Further examples of amino acid derivatives comprise amino acid bearing chemical modifications such the one found in mimetic peptides or peptidomimetics, which are compounds containing non-peptidic structural elements that are capable of mimicking or antagonizing the biological action(s) of a natural parent peptide. A peptidomimetic usually does no longer have classical peptide characteristics such as enzymatically scissille peptidic bonds.

Preferably, said amino acid belongs to the group of the non-essential amino acids. Preferred non-essential amino acids are glycine, alanine, proline, serine, cysteine, tyrosine, asparagine, glutamine, aspartic acid, glutamic acid, arginine, histidine. Appropriate amino acids may be accurately selected by selecting those amino acids which are in lower amounts in the patient into which the drug is to be administered. Dosage and administration regimen can be determined as a function of the patient's level in said amino acid. Preferred dosage and administration regimen are those which intend to increase the patients amino acid level up to the normal standard level.

Linking Said at Least One Sushi-Containing Polypeptide to Said at Least One IL-15Rbeta/Gamma Binding Entity:

Said at least one sushi-containing polypeptide of the invention may be linked directly to said at least one IL-15Rbeta/gamma binding entity.

Alternatively, said at least one sushi-containing polypeptide of the invention, and said at least one IL-15Rbeta/gamma binding entity the proteins may be separated by a "linker" amino acid sequence of a length sufficient to ensure that the proteins form proper secondary and tertiary structures.

Preferably, said linker is a peptidic linker which comprises at least one, but less than 30 amino acids e.g., a peptidic linker of 2-30 amino acids, preferably of 10-30 amino acids, more preferably of 15-30 amino acids, still more preferably of 19-27 amino acids, most preferably of 20-26 amino acids.

Preferred linkers are those which allow the compound to adopt a proper conformation (i.e., a conformation allowing a proper signal transducing activity through the IL-15Rbeta/gamma signalling pathway). Examples of preferred linkers include flexible linkers.

The most suitable linker sequences (1) will adopt a flexible extended conformation, (2) will not exhibit a propensity for developing ordered secondary structure which could interact with the functional domains of fusion proteins, and (3) will have minimal hydrophobic or charged character which could promote interaction with the functional protein domains. Typical surface amino acids in flexible protein regions include Gly, Asn and Ser (i.e., G, N or S). Virtually any permutation of amino acid sequences containing Gly, Asn and Ser would be expected to satisfy the above criteria for a linker sequence. Other near neutral amino acids, such as Thr, Ala, Leu, Gln (i.e., T, A, L, Q) may also be used in the linker sequence. The length of the linker sequence may vary without significantly affecting the biological activity of the fusion protein.

Exemplary linker sequences are described in U.S. Pat. Nos. 5,073,627 and 5,108,910.

Illustrative flexible linkers which are more particularly suitable for the present invention include those coded by the sequences of SEQ ID NO: 49 or NO: 51 (amino acid sequences of SEQ ID NO: 50—also referred to as linker 20—and NO: 52—also referred to as linker 26—, respectively).

In a compound of the invention, the sequence of said at least one sushi-containing polypeptide can be in a N-terminal position relative to the sequence of said at least one IL-15Rbeta/gamma binding entity.

Alternatively, the sequence of said at least one sushi-containing polypeptide can be in a C-terminal position relative to the sequence of said at least one IL-15Rbeta/gamma binding entity.

A compound of the invention can be a fusion protein.

Fusion proteins are polypeptides that comprise two or more regions derived from different or heterologous, proteins or peptides. Fusion proteins are prepared using conventional techniques of enzyme cutting and ligation of fragments from desired sequences. PCR techniques employing synthetic oligonucleotides may be used to prepare and/or amplify the desired fragments. Overlapping synthetic oligonucleotide representing the desired sequences can also be used to prepare DNA constructs encoding fusion proteins. Fusion proteins can comprise several sequences, including a leader (or signal peptide) sequence, linker sequence, a leucine zipper sequence, or other oligomer-forming sequences, and sequences encoding highly antigenic moieties that provide a means for facile purification or rapid detection of a fusion protein.

Illustrative of the compounds of the invention are the fusion protein which comprise the sushi-containing polypeptide of SEQ ID NO: 30 (it+sushi+hinge), and the human wild-type IL-15 of SEQ ID NO: 48, optionally linked together via a linker.

Further illustrative of the compounds of the invention are the fusion protein which comprise:
the signal peptide of SEQ ID NO: 5,
the Flag tag and Xa binding site sequence of SEQ ID NO: 54,
the sushi-containing polypeptide of SEQ ID NO: 30 (it+sushi+hinge),
the linker of SEQ ID NO: 50, and
the human wild-type IL-15 of SEQ ID NO: 48,
i.e., the RLI fusion protein encoded by SEQ ID NO: 60.

Further illustrative of the compounds of the invention are the fusion protein which comprise:
the signal peptide of SEQ ID NO: 58,
the Flag tag and Xa binding site sequence of SEQ ID NO: 56,
the human wild-type IL-15 of SEQ ID NO: 48,
the linker of SEQ ID NO: 52,
the sushi-containing polypeptide of SEQ ID NO: 30 (it+sushi+hinge),
i.e., the ILR fusion protein of SEQ ID NO: 62.

The compounds of the invention can be produced by any means that the skilled person may find appropriate, such as e.g., chemical polypeptide synthesis, or polypeptide biosynthesis.

Chemical polypeptide synthesis is now routine (see e.g. Andersson et al., 2000, Biopolymers (Peptide Science) 55: 227-250), and many companies are specialized in such synthesis.

Preferably, the compounds of the present invention are synthesized by solid phase peptide synthesis (SPPS) techniques using standard FMOC protocols (See, e.g., Carpino et al., 1970, J. Am. Chem. Soc. 92 (19):5748-5749; Carpino et al., 1972, J. Org. Chem. 37 (22):3404-3409).

Alternatively, the skilled person may choose to produce the compounds biologically by in vitro or in vivo translation of a nucleic acid coding for such a compound.

Nucleic Acids, Vectors, Host Cells:

The present invention hence also relates to nucleic acids (DNA or RNA) coding for a product which is intended for stimulating the IL-15Rbeta/gamma signalling pathway, to thereby induce and/or stimulate the activation and/or proliferation of IL-15Rbeta/gamma-positive cells, such as NK and/or T cells.

More particularly, the nucleic acids of the invention code for an isolated sushi-containing polypeptide of the invention, as herein defined, or for a covalently linked compound of the invention, as herein defined (i.e., comprising at least one sushi-containing polypeptide directly or indirectly linked by covalence to at least one IL-15Rbeta/gamma binding entity). Said coding is in accordance with the universal genetic code, taking due account of its degeneracy.

The nucleic acids of the invention can optionally be contained within a vector, such as transfection vector, or an expression vector.

The nucleic acids of the invention may be operably linked to a suitable transcriptional or translational regulatory sequence such as transcriptional promoters or enhancers, an optional operator sequence to control transcription, a sequence encoding suitable mRNA ribosomal binding sites, and appropriate sequences that control transcription and translation initiation and termination. Examples of such vectors include pEF1/myc-His (In Vitrogen, V921-20), pcDNA3.1 (In Vitrogen, V800-20).

The nucleic acids of the invention may also be linked to a leader sequence that enables improved extracellular secretion of the translated polypeptide. Examples of such leader sequences include leader sequences from rat pre-prolactin (SEQ ID NO: 57) or from an IL-15Ralpha, such as the human IL-15Ralpha signal peptide CDS of SEQ ID NO: 4).

The sequence of these nucleic acids may also comprise a stop codon (TAG, TGA, TAA) at their 3' terminal end.

The present invention relates to every nucleic acid encoding one of the described compounds of the invention. Table 4, which located before the claims section, indicates the respective SEQ ID NO: of these nucleic acids.

For example:
a nucleic coding for said human IL-15Ralpha can comprise the sequence of SEQ ID NO: 2;

a nucleic coding for said human extracellular IL-15Ralpha can comprise the sequence of SEQ ID NO: 39;

a nucleic coding for said human sushi domain can comprise the sequence of SEQ ID NO: 13;

a nucleic coding for said human tail region can comprise the sequence of SEQ ID NO: 31;

a nucleic coding for said exon 3 encoded part of said human tail region can comprise the sequence of SEQ ID NO: 33;

a nucleic coding for said human IL-15 can comprise the sequence of SEQ ID NO: 47;

a nucleic coding for a covalently linked compound of the invention can comprise the sequence of SEQ ID NO: 59 (RLI fusion protein) or of SEQ ID NO:61 (ILR fusion protein).

A nucleic acid of the invention can comprise a Kozak sequence at its 5' end, e.g., a Kozak sequence from human wild-type IL-15R, such as gcc gcc; or a Kozak sequence from bovine preprolactine, such as gcc acc.

A nucleic acid of the invention can comprise a stop codon (e.g., tag, tga, or taa) at its 3' end.

The present invention also relates to any vector, comprising a nucleic acid of the invention. Preferably, such a vector is a baculovirus vector.

Said vector can, e.g., be a transfection, or an expression vector.

The present invention also relates to any host cell, transformed or transfected by a nucleic acid of and/or by a vector of the invention.

As used herein, "transfected" or "transfection" means the introduction of one or more exogenous nucleic acids into a eukaryotic cell. Transfection includes introduction of naked nucleic acids such as plasmids by standard physical and chemical transfection techniques, including calcium phosphate precipitation, dextran sulfate precipitation, electroporation, liposome-mediated nucleic acid transfer, ballistic methods such as particle bombardment, etc. Transfection also includes introduction of nucleic acids into cells by biological methods, including viral transduction or infection (receptor-mediated and non-receptor-mediated).

As used herein, "transformed" or "transformation" means the introduction of one or more exogenous nucleic acids into a prokaryotic cell. Transformation includes introduction of naked nucleic acids, as well as of a nucleic acid vector, such as a phage.

Suitable host cells include prokaryotes, yeast or higher eukaryotic cells under the control of appropriate promoters.

Prokaryotes include Gram positive and Gram negative organisms, for example *Escherichia coli, Bacillus subtilis, Salmonella typhimurium*, and various other species within the *Bacillus, Pseudomonas, Streptomyces* and *Staphylococcus* genera.

Examples of suitable host cells also include yeast such as *Saccharomyces cerevisiae*, and higher eukaryotic cells, such as established cell lines of mammalian or insect origin. Examples of suitable higher eukaryotic cells comprise mammalian cell lines, such as Chinese Hamster Ovary (CHO) cells, e.g. Chinese ovary hamster cell line CHO/dhfr⁻ (CHO duk⁻) (ATCC n° CRL-9096), or such as epithelial cell lines, e.g. simian epithelial cell line COS-7 (ATCC n° CRL 1651), or human cell lines, e.g. 293 c18 human kidney cell line (ATCC n° CRL-10852) or FreeStyle 293-F human kidney cell line (In Vitrogen n° R790-07).

Said host cell may be a eukaryotic cell, a mammalian cell (human or non-human such as a CHO cell), a yeast cell, or a prokaryotic cell (such as *E. coli*).

Most preferably, said host cell is a mammalian cell, as the present invention that such cells are more efficient (independently from any problem of glycosylation).

Biological and Medical Applications:

The products of the invention notably comprise said sushi-containing polypeptides in isolated form as herein defined, and the covalently linked form thereof, which is herein referred to as the covalently linked compound of the invention (i.e., the compound which comprises at least one sushi-containing polypeptide directly or indirectly linked by covalence to at least one IL-15Rbeta/gamma binding entity).

The products of the invention also comprise the nucleic acids coding for such polypeptides and compounds, the vector comprising such nucleic acids, as well as the host cells transformed or transfected by such a nucleic acid or such a vector.

The products of the invention are useful to expand lymphocyte subsets, such as particular T/NK subsets. The present invention thus relates to the use of a product of the invention as an agent for expanding one or several lymphocyte populations, such as NK cells, NK-T cells, CD8+ memory cells, and to the adjuvants, compositions and kits intended for such a use, including the pharmaceutical compositions and drugs, which comprise at least one product of the invention. Said at least one sushi-containing polypeptide and said at least one IL-15Rbeta/gamma binding entity can be used in a combined form, such as e.g., in the form of a covalently linked compound of the invention, or in separate forms. The present invention thus relates to:

said at least one IL-15Rbeta/gamma binding entity, as herein defined, and said at least one sushi-containing polypeptide, as herein defined, or their respective nucleic acid, vector, host cells, as a combined preparation for simultaneous, separate or sequential use, i.e., in a kit-of-parts format.

The present invention thus relates to such a preparation, which is an adjuvant, a composition or a kit, including a pharmaceutical composition and a drug.

The present application thus relates to the prevention and/or alleviation and/or treatment of a condition or disease in which an increase of IL-15 activity is desired, such as notably cancer or immunodeficiency. Such a prevention and/or alleviation and/or treatment may act by stimulating the proliferation and/or survival of lymphocytes (such as T cells, CD8+ T cells, NK cells, dendritic cells) and/or their activity against tumoral cells.

A prevention and/or alleviation and/or treatment method of the invention comprises the administration of a product of the invention to a patient in need thereof.

The present invention also relates to adjuvants, compositions, pharmaceutical compositions, drugs, and vaccines, which are intended for such a prevention and/or alleviation and/or treatment.

The pharmaceutical compositions, drugs and vaccines of the invention comprise at least one product of the invention, and optionally a pharmaceutically acceptable vehicle and/or carrier and/or diluent and/or adjuvant.

The present invention more particularly relates to an adjuvant. Such an adjuvant is notably adapted to the induction and/or stimulation of an immune response, which comprises an isolated IL-15Ralpha sushi domain, or a conservative variant thereof. Such an adjuvant may be an adjuvant for an anti-microbial (anti-viral, anti-bacterial, anti-fungal) vaccine, or for an anti-tumour vaccine.

The present invention also relates to:
- a composition which can be notably intended for inducing and/or stimulating an IL-15 biological action, which comprises an isolated IL-15Ralpha sushi domain, or a conservative variant thereof,
- the use of an isolated IL-15Ralpha sushi domain, or a conservative variant thereof, for the manufacture of an adjuvant for immunotherapeutic composition,
- the use of an isolated IL-15Ralpha sushi domain, or a conservative variant thereof, for the manufacture of a composition intended for inducing and/or stimulating an IL-15 biological action The present application thus relates to a drug or vaccine comprising at least one sushi-containing polypeptide as herein defined, and optionally a pharmaceutically acceptable vehicle and/or carrier and/or diluent and/or adjuvant.

Such a drug or vaccine is intended for prevention and/or treatment and/or alleviation of a condition or disease in which an increase of IL-15 activity is desired, such as notably cancer or immunodeficiency. Such a drug or vaccine may act by stimulating the proliferation and/or survival of lymphocytes (such as T cells, $CD8^+$ T cells, NK cells, dendritic cells) and/or their activity against tumoral cells.

The present invention more particularly relates to an anti-tumoral drug or vaccine which exerts its preventive and/or alleviating and/or therapeutic action through the stimulation of the proliferation of NK and CD8+ T cells expressing IL-15Rbeta/gamma but not IL-15Ralpha.

Such an antitumoral drug or vaccine is therefore intended for those patients, whose NK and/or CD8+ T cell populations are insufficiently active to exert an efficient antitumor surveillance or clearance.

Such an antitumoral drug or vaccine is more particularly intended for those patients who have an insufficient population or an insufficiently active population of NK and/or CD8+ T cells expressing IL-15Rbeta/gamma but not IL-15Ralpha.

An antitumoral drug or vaccine of the invention may comprise an isolated IL-15Ralpha sushi domain or a conservative variant thereof.

A preferred anti-tumoral drug or vaccine of the invention comprises:
- at least one IL-15Rbeta/gamma binding entity, as herein defined, such as IL-15, and
- at least one sushi-containing polypeptide, as herein defined, such as an isolated Il-15Ralpha sushi domain, or a conservative variant thereof. Preferably, at least one IL-15Rbeta/gamma binding entity, such as IL-15, and said at least one sushi-containing polypeptide, such as an isolated Il-15Ralpha sushi domain, or a conservative variant thereof, are linked in a fusion protein, thereby forming a covalently linked compound of the invention.

The present invention also relates to the prevention and/or alleviation and/or treatment of a disease or condition involving an immunodeficiency.

The present invention more particularly relates to the prevention and/or alleviation and/or treatment of a disease or condition involving a HIV-related immunodeficiency.

This prevention and/or alleviation and/or treatment comprise the administration of a product of the invention to a patient in need thereof.

The present invention relates to a drug and/or composition for such a prevention and/or alleviation and/or treatment.

The present invention thus relates to an adjuvant for immunotherapeutic composition, characterized in that it comprises at least one element among the following elements:
- a compound of the invention,
- a nucleic acid of the invention,
- a vector of the invention,
- a host cell of the invention.

Advantageously, said adjuvant improves the CD8 memory response.

In the present application, «immunotherapy» encompasses therapy, palliation and/or prevention by induction and/or stimulation of an immune response. The term «immunotherapeutic composition» hence encompasses preventive vaccines, as well as palliative and/or therapeutic "vaccines".

The term «adjuvant» is intended to define a substance which can be added to a composition to improve an immune response (innate immune response and/or adaptive immune response). In the present invention, it further encompasses a substance which can be added to a composition to improve the efficiency of this composition over time, i.e., the duration of the immune response (memory CD8+ T cells).

The compound of the invention may be used in a composition as an adjuvant compound, but can also act by itself as an active principle.

It is indeed, on and of its own, able to induce and/or stimulate the proliferation and activation of IL-15Rbeta/gamma-positive cells, and more particularly the differentiation of NK and/or T cells from naïve NK and/or T cells.

The term «active principle» is intended to define a substance which can elicit an immune response.

As an adjuvant for immunotherapeutic composition, a compound of the invention improves the intensity of the immune response (innate immune response; an adaptive immune response) and/or improves the duration of the immune response (it improves the T CD8 memory response).

As an active agent for an immunotherapeutic composition, a compound of the invention induces an immune response, which is of higher intensity and/or longer duration that that induced by other NK/T cell stimulators.

Hence, whether used as an adjuvant in association with another immune response induced, or used as an active principle which on and of its own induces an immune response, a compound of the invention improves the intensity and/or duration of the immune response. It advantageously:
- induces an improved innate immune response,
- induces an improved adaptive immune response, and more particularly an improved CD8 memory response.

The application also relates to an adjuvant composition, which comprises at least one element among the following elements:
- a compound of the invention, as herein defined,
- a nucleic acid of the invention,
- a vector of the invention,
- a host cell of the invention.

The application also relates to a method of producing an adjuvant for an immunotherapeutic composition, characterized in that it comprises:
- providing a soluble IL-15Ralpha molecule, or a fragment thereof that has retained its sushi domain,
- linking it by covalence to an IL-15Rbeta/gamma binding element, selected from IL-15, an IL-15 fragment, agonist or mimetic which has an affinity for binding to IL-15Rbeta/gamma that is not significantly lower than the one of native IL-15 (capable of competing with native IL-15 and/or IL-2 for binding to IL-15Rbeta/gamma), and which preferably does not bind to IL-2Ralpha, whereby the compound resulting therefrom is an adjuvant for an immunotherapeutic composition.

The present invention also relates to a composition, a pharmaceutical composition or a drug comprising at least one polypeptide containing the sushi domain of IL-15Ralpha, as herein defined, i.e., wherein the amino acid sequence of said at least one sushi-containing polypeptide:

is the amino acid sequence of the extracellular region of human IL-15Ralpha, or of a fragment thereof which has retained the sushi domain of said IL-15Ralpha, wherein the sushi domain of IL-15Ralpha is defined as beginning at the first exon 2 encoded cysteine residue (C1), and ending at the fourth exon 2 encoded cysteine residue (C4), residues C1 and C4 being both included in the sushi sequence, or is at least 85% identical to such an IL-15Ralpha or IL-15Ralpha fragment sequence, provided that each of the four cysteine residues (C1, C2, C3 and C4) of said sushi domain have been retained.

Preferably, said percentage of identity is of at least 90%, still more preferably of at least 92%, most preferably of at least 95%, e.g., at least 96%, at least 97%, at least 98%, at least 99% or 100%.

The present invention more particularly relates to a composition, a pharmaceutical composition or a drug which comprises at least one polypeptide containing the sushi domain of IL-15Ralpha, as herein defined, wherein said at least one sushi-containing polypeptide comprises, or consists of, the part of extracellular IL-15Ralpha that is encoded by exons 2 and 3, or a fragment of such a part which has retained the sushi domain.

The present invention preferably relates to a composition, a pharmaceutical composition or a drug which comprises:

a human IL-15Ralpha fragment, the amino acid sequence of which is the amino acid extending from position 1 to position 127 of SEQ ID NO: 3, or a sub-fragment thereof which has retained the sushi domain of said fragment, wherein:
said sushi domain is defined as beginning at the first exon 2 encoded cysteine residue (C1), and ending at the fourth exon 2 encoded cysteine residue (C4), residues C1 and C4 being both included in the sushi domain, and
the amino acid sequence of said signal peptide being the sequence extending from position 1 to position 30 of said SEQ ID NO:3, or a variant of said fragment or sub-fragment, which has an amino acid sequence identity of at least 85% over the entire length of said fragment or sub-fragment.

Preferably, said percentage of identity is of at least 90%, still more preferably of at least 92%, most preferably of at least 95%, e.g., at least 96%, at least 97%, at least 98%, at least 99% or 100%.

Such a composition, pharmaceutical composition, or drug may further comprise at least one IL-15Rbeta/gamma binding entity, such as IL-15, or an IL-15 fragment or variant as herein defined.

Said at least one IL-15Rbeta/gamma binding entity can be not linked to said at least one sushi-containing polypeptide by covalence, i.e., be placed in a free form in said composition, and/or can be linked by covalence to said to said at least one sushi-containing polypeptide. In the latter case, the composition, pharmaceutical composition, or drug of the invention in fact comprises a compound of the invention as herein defined.

Such a pharmaceutical composition or drug can be intended for agonizing an IL-15 biological action, and more particularly for inducing and/or stimulating the proliferation and/or activation of IL-15Rbeta/gamma-positive cells.

Such a pharmaceutical composition or drug can be intended for inducing and/or stimulating the proliferation and/or activation of a NK and/or T immune response. Such a pharmaceutical composition or drug can be intended as a preventive and/or palliative and/or therapeutic vaccine composition.

Such a pharmaceutical composition or drug can be intended for the prevention and/or palliation and/or treatment of an infectious disease, and/or for the prevention and/or palliation and/or treatment of an immunodeficiency (such as a HIV-induced immunodeficiency), and/or for the prevention and/or palliation and/or treatment of a tumour development or presence (and may then further contain at least one tumour antigen), and/or for the prevention and/or palliation and/or treatment of X-SCID.

According to an advantageous embodiment of the present invention, said at least one sushi-containing polypeptide is covalently linked to a IL-15Rbeta/gamma binding entity. Most preferably, this IL-15Rbeta/gamma binding entity does not bind IL-2Ralpha.

According to a preferred embodiment of the present invention, said at least one sushi-containing polypeptide is covalently linked to a IL-15Rbeta/gamma binding entity, which is IL-15, or is an IL-15 fragment, mimetic, or agonist, which has an affinity for binding to IL-15Rbeta/gamma that is not significantly lower than the one of native IL-15 (i.e., a fragment, mimetic or agonist which is capable of competing with native IL-15 and/or IL-2 for binding to IL-15Rbeta/gamma).

The present invention thus more particularly relates to a pharmaceutical composition, intended for stimulating the IL-15Rbeta/gamma signalling pathway, to thereby induce and/or stimulate the activation and/or proliferation of IL-15Rbeta/gamma-positive cells, such as NK and/or T cells, characterized in that it comprises at least one element among the following elements:
a compound of the invention,
a nucleic acid of the invention,
a vector of the invention,
a host cell of the invention.

Such a pharmaceutical composition may further comprise a pharmaceutically appropriate vehicle (carrier, diluent, excipient, additive, pH adjuster, emulsifier or dispersing agent, preservative, surfactant, gelling agent, as well as buffering and other stabilizing and solubilizing agent, etc.).

The present invention also relates to a drug, intended for stimulating the IL-15Rbeta/gamma signalling pathway, to thereby induce and/or stimulate the activation and/or proliferation of IL-15Rbeta/gamma-positive cells, such as NK and/or T cells, characterized in that it comprises at least one element among the following elements:
a compound of the invention,
a nucleic acid of the invention,
a vector of the invention,
a host cell of the invention.

Said drug is preferably an immunotherapeutic composition.

Such a drug most preferably is a preventive and/or palliative and/or therapeutic vaccine composition.

Said drug may further comprise a physiologically appropriate vehicle (carrier, diluent, excipient, additive, pH adjuster, emulsifier or dispersing agent, preservative, surfactant, gelling agent, as well as buffering and other stabilizing and solubilizing agent, etc.).

Appropriate pharmaceutically acceptable vehicles and formulations include all known pharmaceutically acceptable vehicles and formulations, such as those described in "Remington: The Science and Practice of Pharmacy", 20$^{th}$ edition, Mack Publishing Co.; and "Pharmaceutical Dosage Forms and Drug Delivery Systems", Ansel, Popovich and Allen Jr., Lippincott Williams and Wilkins.

In general, the nature of the carrier will depend on the particular mode of administration being employed. For instance, parenteral formulations usually comprise, in addition to the one or more contrast agents, injectable fluids that include pharmaceutically and physiologically acceptable fluids, including water, physiological saline, balanced salt solutions, buffers, aqueous dextrose, glycerol, ethanol, sesame oil, combinations thereof, or the like as a vehicle. The medium also may contain conventional pharmaceutical adjunct materials such as, for example, pharmaceutically acceptable salts to adjust the osmotic pressure, buffers, preservatives and the like. The carrier and composition can be sterile, and the formulation suits the mode of administration.

For solid compositions (e.g., powder, pill, tablet, or capsule forms), conventional nontoxic solid carriers can include, for example, pharmaceutical grades of mannitol, lactose, starch, sodium saccharine, cellulose, magnesium carbonate, or magnesium stearate. In addition to biologically-neutral carriers, pharmaceutical compositions to be administered can contain minor amounts of auxiliary substances, such as wetting or emulsifying agents, preservatives, and pH buffering agents and the like, for example sodium acetate or sorbitan monolaurate.

The composition can be a liquid solution, suspension, emulsion, tablet, pill, capsule, sustained release formulation, or powder. The composition can be formulated with traditional binders and carriers, such as triglycerides.

A composition or drug of the invention is useful in inducing and/or stimulating an IL-15 biological action through the IL-15Rbeta/gamma signalling pathway. It is more particularly useful in inducing and/or stimulating an innate immune response (NK cells), and/or an adaptive immunity (T cells, and more particularly T CD8+ memory cells).

According to a very advantageous embodiment of the present invention, said drug can be intended for the prevention and/or palliation and/or treatment of a tumour development or presence.

Said tumour can, e.g., be a melanoma, a lymphoma, a carcinoma (e.g., cervical carcinoma), a breast cancer, an ovarian cancer, a pancreatic tumour.

Advantageously, said anti-tumour drug is an anti-tumour vaccine acting through transpresentation.

An anti-tumour drug of the invention can further comprise at least one tumour antigen. Said at least one tumour antigen can be in a soluble form, or be linked to a compound of the invention (by covalence or by another form of linkage).

Said at least one tumour antigen is advantageously provided in the form of dendritic cells loaded with such an antigen, e.g., genetically engineered dendritic cells which express said at least one tumour antigen.

Tumour antigens are antigens that are presented by MHC I molecules on the surface of tumour cells. Tumour antigens can also be on the surface of the tumour in the form of, for example, a mutated receptor, in which case they will be recognized by B cells.

Tumour antigens can sometimes be presented only by tumour cells and never by the normal ones. In this case, they are called tumour-specific antigens (TSA), or tumour-specific transplantation antigens (TSTA), or tumour rejection antigens (TRA), and typically result from a tumour specific mutation. TSA usually appear when an infecting virus has caused the cell to become immortal and to express virus antigen. TSA non induced by viruses are the idiotypes of BCR on B cell lymphomas or TCR on T cell lymphomas.

More common are antigens that are presented by tumour cells and normal cells, and they are called tumour-associated antigens (TAA). TAA are found on tumour cells and on ormal cells during fetal life (onco-fetal antigens), after birth in selected organs, or in many cells but at a much lower concentration than on tumour cells.

Oncogenes may be expressed in cancer-causing viruses. Most oncogenes are actually present in the host cell, where they function in regulated cell growth When transduced by the virus and expressed under the control of viral promotor, the product of the host cell gene, i.e., the product of the proto-oncogene, contributes to the unregulated growth of the tumour cell. Since proteins encoded by proto-oncogenes are usually expressed by normal cells, their over-expression on tumour cells would qualify them as tumour-associated antigens.

Cytotoxic T lymphocytes that recognized these antigens may be able to destroy the tumour cells before they proliferate or metastasize. Tumour cells may however downregulate MHC Class I expression. They often lack co-stimulatory molecules like B7 or adhesion molecules that are necessary for them to interact with T CD8+ cells. Some tumour cells actively suppress the immune response by producing a suppressive cytokine, such as TGFbeta, that inhibits cellular immunity.

Examples of tumour antigens notably comprise:
  cell cycle regulators, such as cyclin-dependent kinase 4 (melanoma),
  signal transducers, such as beta-catenin (melanoma),
  apoptosis regulators, such as caspase-8 (squamous cell carcinoma),
  testicular proteins such as the MAGE antigens (melanoma, breast, glioma tumours), e.g., MAGE-1 (accession number P43355), MAGE-2 (accession number P43356), MAGE-3 (accession number P43357), MAGE-4 (accession number P43358), MAGE-6 (accession number P43360), MAGE-8 (accession number P43361), MAGE-9 (accession number P43362), MAGE-10 (accession number P43363), MAGE-11 (accession number P43364), MAGE-12 (accession number P43365),
  compound involved in melanin synthesis (melanoma), such as tyrosinase (accession number P14679),
  BCR idiotypes, such as surface Ig idiotype (lymphoma),
  tyrosine kinase receptors, such as Her-2/neu, MUC-1 (breast and ovarian cancer),
  underglycosylated mucins, such as MUC-1 (breast and pancreatic tumours),
  viral gene products, such as HPV E6 and E7 (cervical carcinoma).

A composition or drug of the invention can be intended for the prevention and/or palliation and/or treatment of an infectious disease (infection by a microorganism, such as virus, bacteria, yeast, fungus, etc.).

A composition or drug of the invention can be intended for the prevention and/or palliation and/or treatment of an immunodeficiency (e.g., an immunodeficiency induced as a side effect by a particular treatment, such as an anti-tumour treatment, or a pre-graft treatment; or induced by a virus, such as HIV).

A composition or drug of the invention can be intended for the prevention and/or palliation and/or treatment of SCID-X (X-linked severe combined immunodeficiency, which is linked to an IL-15Rgamma dysfunction).

The formulation of a pharmaceutical composition comprising at least one of the products of the invention is well within the skill of the art. The same holds true for the details of administering said composition. The physician treating the patient will have to take into account, among other parameters, the age, general condition and disease state.

The therapeutically useful compounds identified according to the method of the invention may be administered to a patient by any appropriate method for the particular compound, e.g., orally, intravenously, parenterally, transdermally, transmucosally, or by surgery or implantation (e.g., with the compound being in the form of a solid or semi-solid biologically compatible and resorbable matrix) at or near the site where the effect of the compound is desired. Therapeutic doses are determined to be appropriate by one skilled in the art, and are a function of the body weight.

The invention also relates to a method of treating by therapy and/or palliation and/or prevention a patient or non-human animal in need thereof with a compound.

The present invention also relates to a method of treating a patient in need thereof (treatment by therapy and/or palliation and/or prevention), by administration of a product, composition or drug of the invention.

The present invention also relates to a process for inducing and/or stimulating the proliferation and/or activation of IL-15Rbeta/gamma-positive cells, characterized in that it comprises:
contacting IL-15Rbeta/gamma-positive cells with at least one of the following elements:
a compound of the invention,
a nucleic acid of the invention,
a vector of the invention,
a host cell of the invention,
whereby the proliferation and/or activation of said IL-15Rbeta/gamma-positive cells is induced and/or stimulated.

Said contacting is performed under conditions enabling the proliferation and/or activation of said IL-15Rbeta/gamma-positive cells. Such conditions notably comprise the duration of time, and the environmental conditions (temperature, atmosphere, culture medium). Adjusting these conditions pertains to the competence of the person of ordinary skilled in the art.

The present invention also relates to an vitro process for inducing and/or stimulating the proliferation and/or activation of IL-15Rbeta/gamma-positive cells, characterized in that it comprises:
providing a cell sample which comprises IL-15Rbeta/gamma-positive cells,
contacting said sample with at least one of the following elements:
a compound of the invention,
a nucleic acid of the invention,
a vector of the invention,
a host cell of the invention,
for a period of time and under environmental conditions enabling said contacting to induce and/or stimulate the proliferation and/or activation of said IL-15Rbeta/gamma-positive cells.

The present invention also relates to a process for producing activated NK and/or T cells, characterized in that it comprises:
contacting resting NK and/or T cells with at least one of the following elements:
a compound of the invention,
a nucleic acid of the invention,
a vector of the invention,
a host cell of the invention,
for a period of time and under environmental conditions enabling said contacting to induce the activation of said resting NK and/or T cells comprised in said sample.

The present invention also relates to an in vitro process for producing activated NK and/or T cells, characterized in that it comprises:
providing a cell sample which comprises resting NK and/or T cells,
contacting said sample with at least one of the following elements:
a compound of the invention,
a nucleic acid of the invention,
a vector of the invention,
a host cell of the invention,
for a period of time and under environmental conditions enabling said contacting to induce the activation of said resting NK and/or T cells comprised in said sample.

In the process for inducing and/or stimulating the proliferation and/or activation of IL-15Rbeta/gamma-positive cells, and in the process for producing activated NK and/or T cells, the contacted cells may be cell lines. They alternatively can be ex vivo cells collected from an organism (e.g., a human patient), and intended to be returned to this or another organism (e.g., the same patient) after in vitro treatment.

Hence, the present invention encompasses the ex vivo embodiment of said processes, and their implementation in the course of a treatment by therapy and/or palliation and/or prevention.

In the present application, the "stop" codon (TAG, TGA, or TAA) is usually not declared as being comprised within the CDS.

The term "comprising", which is synonymous with "including" or "containing", is open-ended, and does not exclude additional, unrecited element(s), ingredient(s) or method step(s), whereas the term "consisting of" is a closed term, which excludes any additional element, step, or ingredient which is not explicitly recited. The term "essentially consisting of" is a partially open term, which does not exclude additional, unrecited element(s), step(s), or ingredient(s), as long as these additional element(s), step(s) or ingredient(s) do not materially affect the basic and novel properties of the invention.

The term "comprising" (or "comprise(s)") hence includes the term "consisting of" ("consist(s) of"), as well as the term "essentially consisting of" ("essentially consist(s) of"). Accordingly, the term "comprising" (or "comprise(s)") is, in the present application, meant as more particularly encompassing the term "consisting of" ("consist(s) of"), and the term "essentially consisting of" ("essentially consist(s) of").

The term "significantly" is herein used in its usual meaning in the field of statistics (e.g., t test, z test, chi squared value, or F ratio, etc.), i.e., for comparing a value to another one, and determining whether these values differ from each other. The term "significantly" hence encompasses the fact that the skilled person may take into account the standard deviation (if any), which measures the amount of spread of data in a frequency distribution. The desired p value is usually set at an alpha level of 5%, or at the more stringent alpha level of 1%.

Each of the relevant disclosures of all references cited herein are specifically incorporated by reference, The following examples are offered by way of illustration, and not by way of limitation.

EXAMPLES

Experimental Procedures

Cell Culture and Cytokines—

Recombinant human IL-15 (rIL-15) was from Peprotech Inc (Rocky Hill, N.J.). The Mo-7 myeloid leukemia cell line (human cell line expressing IL-15Rβ/γ but not IL-15Rα), and the TF-1 erythroleukemia human cell line (cell line expressing IL-15Rα and IL-15Rγ, but not IL-15Rβ; ATCC CRL-2003) were cultured in RPMI 1640 medium containing 10% heat inactivated fetal calf serum (FCS), 2 mM glutamine, and 1 ng/ml GM-CSF (R&D Systems; Abington, UK). TF1-β cells (22) were cultured in the same medium supplemented with 250 µg/ml geneticin. The Kit 225 human T lymphoma cell line (IL-2-dependent cell line) was cultured in RPMI 1640 medium containing 6% FCS, 2 mM glutamine, 10 ng/ml rIL-2 (Chiron; Emeryville, Calif.).

The mouse 32Dβ cell line that expresses endogenous mouse IL-15Rγ chain and transfected human IL-15Rβ chain (32D cell line available from ATCC CRL-11346) was cultured in RPMI, 10% FCS, 0.4 ng/ml m-IL-3, 10 µg/ml b-mercaptoethanol, 250 µg/ml geneticine.

sIL-15Rα-IL2, sIL-15Rα-sushi-IL-2 and sIL-15Rα-sushi— sIL-15Rα-IL-2 was expressed in CHO cells and prepared as described (23). A similar construction was made in which the sushi domain of IL-15Rα (amino acids 1-66 of mature coding sequence) was linked to a molecule of human IL-2 (sIL-15Rα-sushi-IL-2).

The sushi-domain of IL15Rα was amplified by PCR. PCR products were purified, digested with BamHI and HindIII (Fermentas, Vilnius, Lithuania) and ligated into pQE30 expression vector. Expression was done in E. coli SG13009 cells under IPTG induction. After cell lysis, inclusions bodies were washed, solubilised in 6 mM guanidine HCl, 20 mM sodium phosphate, pH 7.4, 20 mM imidazol, 150 mM sodium chloride and 1 mM DTT. The IL-15Rα-sushi was trapped on a Ni-NTA agarose column (Qiagen) equilibrated with the solubilisation buffer plus 1 mM reduced glutathione and 0.2 mM oxidized glutathione. It was refolded via a gradient from 6 to 0 M guanidine HCl in column buffer (24) and eluted with 250 mM imidazol.

RLI and ILR Fusion Proteins—

Figures 2A, 2B, 2C, 2D, 2E, 2F:
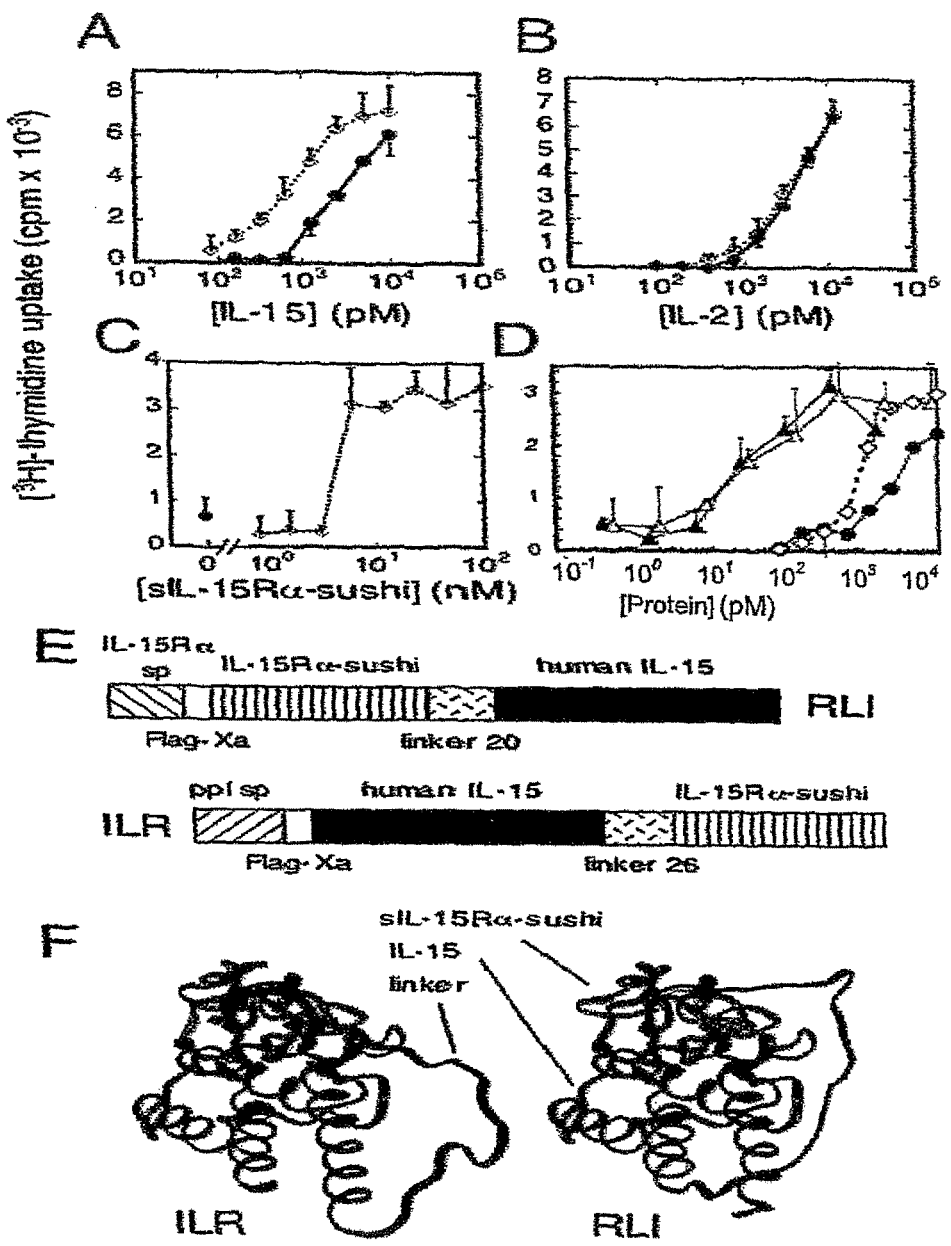
FIG. 2. Effects on IL-15 induced proliferation through IL-15Rβ/γ. The proliferation of Mo-7 cells was evaluated by the incorporation of [$^3$H]-thymidine. Cells were cultured with increasing concentrations of human rIL-15 (A) or human rIL-2 (B), in the absence (●) or presence (◇) of a fixed concentration (10 nM) of sIL-15R$^α$-sushi. (C): Cells were cultured in the presence of 1 nM rIL-1, without (●) or with increasing concentrations of sIL-15Rα-sushi (◇). (D): Cells were cultured with increasing concentrations of rIL-15 (●), equimolar mixture of IL-15 and sIL-15Rα-sushi (◇), RLI (▲) or ILR fusion protein (△). (E); Molecular constructs used to express RLI and ILR fusion proteins. IL-15$Rα$ sp: human IL-15Rα signal peptide, ppl sp: bovine preprolactin signal peptide. (F); Three-dimensional model structures of the fusion proteins.

The constructions of the fusion proteins are shown on FIG. 2E. Human IL-151Rα sushi domain (aa 1-77) and human IL-15 were separated by linker 20 (SGGSGGGGSGGGSGGGGSLQ; SEQ ID NO: 50) for RLI, or by linker 26 (SGGGSGGGGSGGGGSGGGGSGGGSLQ, of SEQ ID NO: 52) for ILR. A sequence coding for the Flag epitope and Factor Xa binding site to (DYKDDDDKIEGR, of SEQ ID NO: 54, for RLI; TTRDYKDDDDKIEGR, of SEQ ID NO: 56, for ILR) was added between the signal peptide (sp) and the coding sequences. The endogenous sp of human IL-15Rα (SEQ ID NO: 5) was used for RLI, and the sp of bovine preprolactine (SEQ ID NO: 58) for ILR.

These constructions were inserted between the BamHI and the HindIII site of pFastBac 1 (InVitrogen) expression vector to generate two expression vectors which were recombined in the baculovirus DNA using the Bac to Bac expression system (InVitrogen). The recombinant baculoviruses were used to infect SF9 cells (ATCC CRL-1711), and fusion proteins were expressed in the SF 900 II medium (Gibco™ Invitrogen Corp.) and harvested 4 days post infection. The concentrations of the fusion proteins were measured by ELISA with the anti-IL-15 mAb 247 (R & D Systems) as capture antibody, and the anti-Flag M2-peroxydase conjugate (Sigma; St Louis, Mo.) as revealing antibody.

Surface Plasmon Resonance (SPR) Studies—

These experiments were performed with a BIACore 2000 biosensor (BIACore, Uppsala, Sweden). rIL-15 was covalently linked to CM5 sensor chips, and the binding of increasing concentrations of sIL-15Rα-IL-2, sIL-15Rα-sushi-IL-2 or sIL-15Rα-sushi was monitored. Analysis of sensograms was performed using BIAlogue kinetics evaluation software.

Proliferation Assays—

The proliferative responses of Mo-7, TF-1β and Kit 225 cells to rIL-15, rIL-2, RLI or ILR were measured by [$^3$H]-thymidine incorporation as described (19) after 4 h in cytokine-deprived medium, 48 h culture and 16 h with [$^3$H]-thymidine.

Apoptosis—

The annexin V assay was performed using a FACScan flow-cytometer and the Annexin V-FITC Apoptosis detection kit (BD Biosciences Pharmingen, France). After cytokine starvation, cells were seeded in multiwell plates at $5·10^5$ cells/well in 1 ml and cultured in medium supplemented with the various reactants (rIL-15, sIL-15Rα-sushi and RLI fusion protein. Data were acquired and analyzed with the use of the CellQuest software.

Binding Assays and Internalization—

Labeling with [$^{125}$I]-iodine of human rIL-15, sIL-15Rα-sushi and RLI fusion protein, and subsequent binding experiments were performed as described previously (19). For internalization, cells were equilibrated at 4° C. with labeled sIL-15Rα-sushi or RLI, and the temperature switched to 37° C. At different time intervals, two samples were washed and centrifuged. One of the cell pellets was treated with glycine-HCl buffer 0.2 M, pH 2.5, whereas the other was treated with PBS pH 7.4 at 4° C. for 5 min. After centrifugation, total ligand binding was determined from the pellet of the cells treated with PBS, whereas the membrane bound and internalized fractions were determined respectively from the supernatant and pellet of cells treated with acid pH.

sIL-15Rα-Sushi$^+$: The Flag-Factor Xa tagged sIL-15Rα-Sushi+ was expressed in insect SF9 cells (ATCC CRL-1711) medium, SF 900 II (In Vitrogen, Cergy-Pontoise, France) as described for the fusion proteins RLI and ILR. The supernatants were concentrated by precipitation with ammonium sulfate at 90% saturation and loaded onto an anti-Flag agarose immunoaffinity column (Sigma-Aldrich, Saint-Quentin Fallavier, France). The purity of the sIL-15Rα-Sushi$^+$ was 100% with an apparent molecular mass of 12 kDa, as assessed by SDS-PAGE after iodination with chloramine-T method as described previously (Lehours et al. Eur. Cytokine Netw. 11 (2000), 207-5). Its concentration was determined by Bicinchoninic Acid (BCA) based protein assay (Pierce, Perbio Science, Brebières, France).

Results

IL-15Rα Binding to IL-15 is Mainly Due to the Sushi Domain—

A previous study (25) has shown that removal of the "sushi" domain encoded by exon 2 of IL-15R resulted in a complete abrogation of the IL-15 binding to membrane anchored IL-15Rα, suggesting that the sushi domain was indispensable for binding. In order to directly measure the contribution of the sushi domain in IL-15 binding, soluble forms of IL-15Rα containing the entire extracellular domain or only the N-terminal sushi domain were prepared and assayed for IL-15 binding in a competition assay and by using the surface plasmon resonance (SPR) technology.

As shown in FIG. 1A, a sIL-15Rα-IL-2 fusion protein produced in CHO cells, and comprising the entire IL-15Rα extracellular domain linked to a molecule of human IL-2 (used as a tag for purification), bound IL-15 with high affinity (kon=3.7 $10^5$ $M^{-1}$ $s^{-1}$ koff=1.4 $10^{-5}$ $s^{-1}$; Kd=38 pM). A similar construction linking the sushi domain of IL-15Rα to human IL-2 also bound IL-15 (FIG. 1B), but with a 10 fold lower affinity, mainly due to a more rapid off rate (kon=3.1 $10^5$ $M^{-1}$ $s^{-1}$; koff=1.3 $10^{-4}$ $s^{-1}$; Kd=420 pM). A soluble sushi domain was also produced in *E. coli*. This sIL-15Rα-sushi also bound IL-15 with a lower affinity (kon=2.5 $105$ $M^{-1}$ $s^{-1}$; koff=3.8 $10^{-4}$ $s^{-1}$; Kd=1.5 nM) (FIG. 1C).

These results indicates that the sushi domain is responsible for a major part of the binding affinity of IL-15, but that it does not fully reconstitute the high-affinity binding displayed by the full length extracellular domain.

As shown in FIG. 1E, a soluble sushi domain extended to the first 13 amino acids coded by exon 3, called hinge region, showed a four fold increase in binding affinity compared to sIL-115Rα-Sushi-IL-2, which contains unextended sushi domain, and only a three fold lower affinity than the full length soluble IL-15Rα, while all three constructs were produced in eukaryotic systems having similar folding abilities. These results indicates that the sushi domain extended to the hinge region almost fully reconstitute the high-affinity binding displayed by the full length extracellular domain.

Results of the analysis of sensorgrams giving the affinity constants for IL-15 ($K_D$), calculated for the various soluble IL-15Rα proteins, and the statistical test constant (Chi 2), are shown in table 3 below:

TABLE 3

|  | $K_D$ (pM) | Chi 2 |
| --- | --- | --- |
| sIL-15R-IL-2 | 34 | 0.183 |
| Sushi15-IL-2 | 428 | 0.159 |
| Sushi15+ | 102 | 0.443 |

Soluble IL-15Rα Proteins Inhibit IL-15 Binding to Membrane-anchored IL-15Rα—

The three soluble forms of IL-15Rα were tested for their ability to compete out the binding of radio-iodinated IL-15 to IL-15Rα expressed by the human cell line TF-1 which also expresses the IL-15Rγ chain, but not the IL-15Rβ chain (FIG. 1D). The three proteins completely inhibited IL-15 binding to TF-1 cells with respective IC50s that were similar to the Kds measured by the SPR technology: 100 pM (sIL-15R(-IL-2), 270 pM (sIL-15Rα-sushi-IL-2) and 1.3 nM (sIL-15Rα-sushi).

sIL-15Rα-sushi Increases IL-15 Driven Cell Proliferation Through the IL-15Rβ/γ Complex—

Since the soluble sushi domain was easily produced in *E. coli* in high yields, it was selected for all further studies. In a first instance, it was tested on cell lines that only express the IL-15Rβ/γ complex (human Mo-7 cell line, and mouse 32Dβ cell line that express endogenous mouse IL-15Rγ chain and transfected human IL-15Rβ chain). As expected, the Mo-7 cell line proliferated in response to nanomolar concentrations of rIL-15 or rIL-2 (FIGS. 2A and 2B). Unexpectedly, the addition in the assay of a fixed concentration of sIL-15Rα-sushi (10 nM) increased the proliferative response that was shifted by about 4 fold towards lower concentrations of rIL-15. By itself, sIL-15Rα-sushi did not induce any proliferative response. On 32Dβ, similar results were obtained with a shift of about 10 fold. The specificity was assessed by the fact that sIL-15Rα-sushi did not affect the rIL-2 driven proliferation of Mo-7 cells (FIG. 2B). FIG. 2C shows that sIL-15Rα-sushi dose-dependently, with an IC50 (3.5 nM) similar to its Kd for IL-15, potentiated the effect of a fixed concentration of rIL-15 (1 nM) that alone induces only a small proliferative effect.

RLI and ILR Fusion Proteins are Potent Inducers of Cell Proliferation Through the IL-15Rβ/γ Complex—

In order to evaluate whether the synergistic effect of sushi on IL-15 bio-activity could be transferred on a single molecule, molecular constructs encoding fusion proteins linking IL-15 and the sushi domain were elaborated. For the two constructions, a flexible linker was introduced between the C terminus of IL-15 and the N terminus of the sushi domain (ILR) or vice-versa (RLI) (FIG. 2E). Molecular models illustrating the structures of these proteins are shown in FIG. 2F. These two fusion proteins were tested on the proliferation of Mo-7 cells.

As shown in FIG. 2D, both proteins induced dose-dependent induction of the proliferation of Mo-7 cells, with EC50s that were similar (about 25 pM) and far lower than the EC50s of rIL-15 alone (3 nM), or of an equimolar mixture of rIL-15 plus sIL-15Rα-sushi (0.9 nM). These results further confirm the synergistic effect of sIL-15Rα-sushi on IL-15 action, and indicate that stabilizing the IL-15: sIL-15Rα-sushi complex with a covalent linker markedly enhances this synergistic action.

sIL-15Rα-sushi Increases IL-15 Induced Prevention of Apoptosis, and RLI Efficiently Prevents Cellular Apoptosis—

Figures 3A, 3B, 3C:
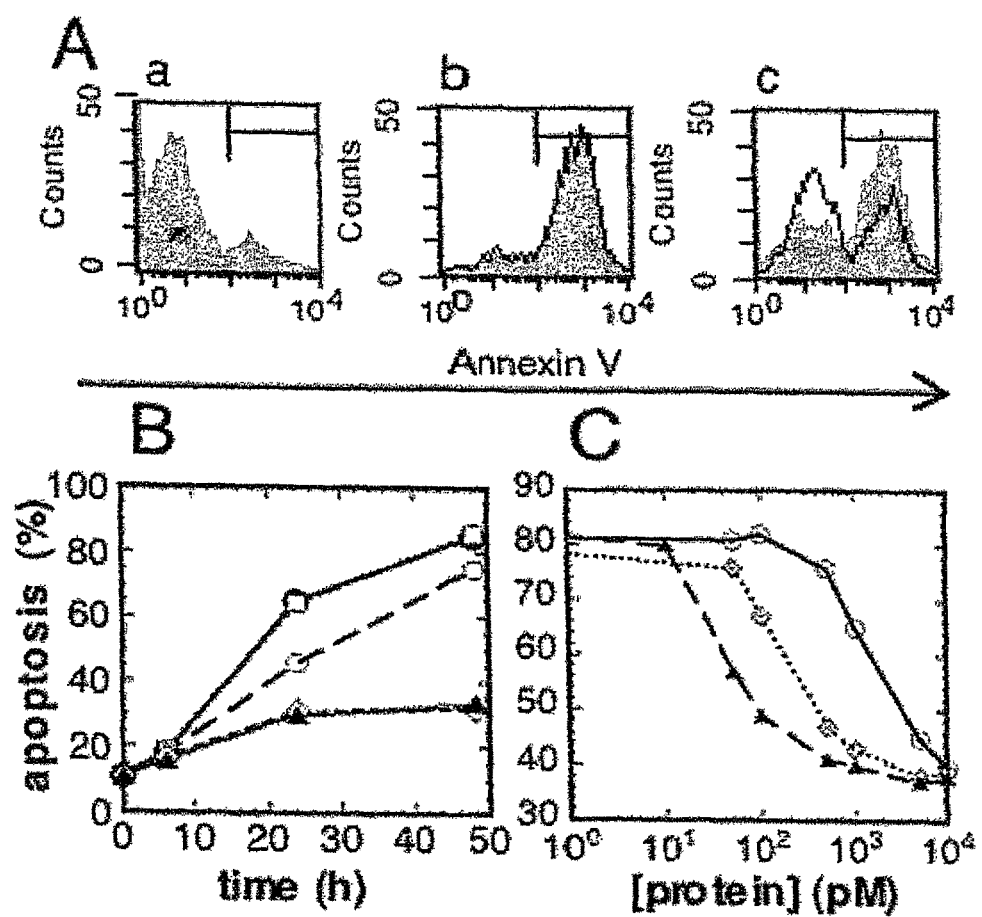
FIG. 3. Effects on IL-15 induced prevention of apoptosis through IL-15Rβ/γ. Apoptosis was evaluated by Annexin V cell surface expression using Flow Cytometry. Full histogram (Aa) represents annexin V staining on Mo-7 at the beginning of the experiment. Cells were cultured for 48 h, without (Ab) or with a fixed concentration of human rIL-15 (500 pM) (Ac), in the absence (full histogram) or presence of sIL-15Rα-sushi (10 nM) (unbroken line). (B): Kinetics of Annexin V expression on Mo-7 cells in the absence of exogenous cytokine (●) or in the presence of rIL-15 (500 pM) (○), sIL-15Rα-sushi (10 nM) (□), sIL-15Rα-sushi (10 nM) plus rIL-15 (500 pM) (◇), or RLI (500 pM) (▲). (C): Mo-7 cells were cultured with increasing concentrations of rIL-15, in the absence (○) or presence (◇) of a fixed concentration (10 nM) of sIL-15Rα-sushi, or with increasing concentrations of RLI (▲).

Following cytokine withdrawal, the fraction of apoptotic Mo-7 cells raised from 10% to 80% in 48 hours (FIG. 3A, graphs a and b). When added at time zero, rIL-15 (5 nM) reduced this apoptosis to 70% (FIG. 3A, graph c). Alone, sIL-15Rα-sushi (10 nM) had no effect (FIG. 3Ab). However, it markedly potentiated the anti-apoptotic effect of rIL-15 (35% apoptosis at 48 h) (FIG. 3A, graph c). The synergistic effect of sIL-15Rα-sushi on IL-15 prevention of apoptosis is confirmed by kinetic analysis (FIG. 3B) and by dose response curves (FIG. 3C). rIL-15 acted with an IC50 of about 1.5 nM, a value in agreement with the saturation of IL-15β/γ receptors. This IC50 was about 10 fold lower (170 pM) in the presence of 10 nM sIL-15Rα-sushi. The RLI fusion protein markedly prevented apoptosis (FIG. 3B). On a molar basis, it was even more active than the IL-15: sIL-15Rα-sushi association, with an IC50 of about 40 pM (FIG. 3C).

sIL-115Rα-sushi Increases IL-15 Binding to Mo-7 Cells and the RLI Fusion Protein Binds to and is Internalized by Mo-7 Cells—

Figures 4A, 4B, 4C:
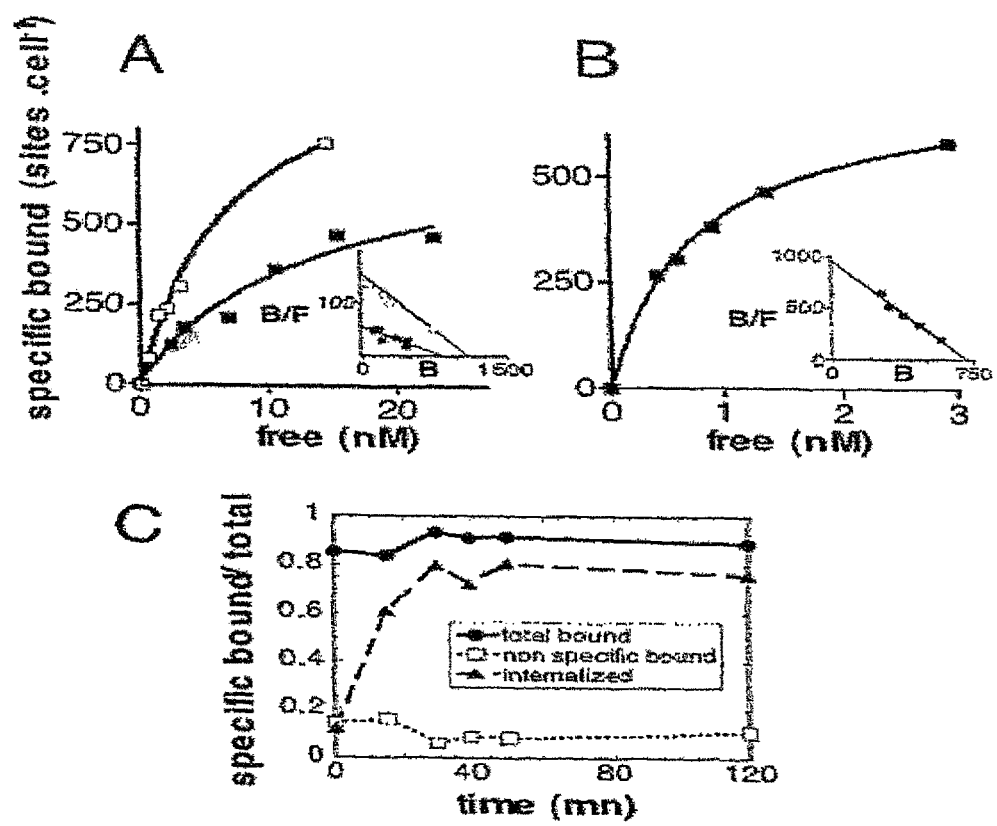
FIG. 4. Agonist effect of sIL-15Rα-sushi on IL-15 binding to IL-15Rβ/γ. Binding and internalization of RLI. (A): Binding of $^{125}$I-labeled rIL-15 to Mo7 cells in the absence (■) or presence of 10 nM sIL-15Rα-sushi (□). (B): Binding of $^{125}$I-labeled RLI fusion protein. In insets are shown Scatchard plots. (C): Internalization of $^{125}$I-labeled RLI fusion protein (500 pM).

As expected, Mo-7 cells bound IL-15 with intermediate affinity (Kd=13.5 nM), with a maximal binding capacity of 800 sites/cell (FIG. 4A). The addition of sIL-15Rα-sushi (10 nM) increased the affinity of IL-15 binding (Kd=7 nM) without significantly affecting the maximal binding capacity (1180 sites/cell). When using radio-iodinated RLI fusion protein (FIG. 4B), we found that it bound to a similar number of receptor sites (730 sites/cell), and the affinity of binding (Kd=780 pM) was markedly higher than that of IL-15. FIG. 4C shows that RLI can be efficiently and rapidly internalized. The fraction of cell-bound radioactivity fell down in about 20 min and was accompanied by a concomitant increase of intracellular radioactivity.

sIL-15Rα-sushi does not Affect IL-15 Driven Cell Proliferation Nor Inhibition of Apoptosis Through the High Affinity IL-15Rα/β/γ Complex—

Figures 5A, 5B, 5C, 5D, 5E:
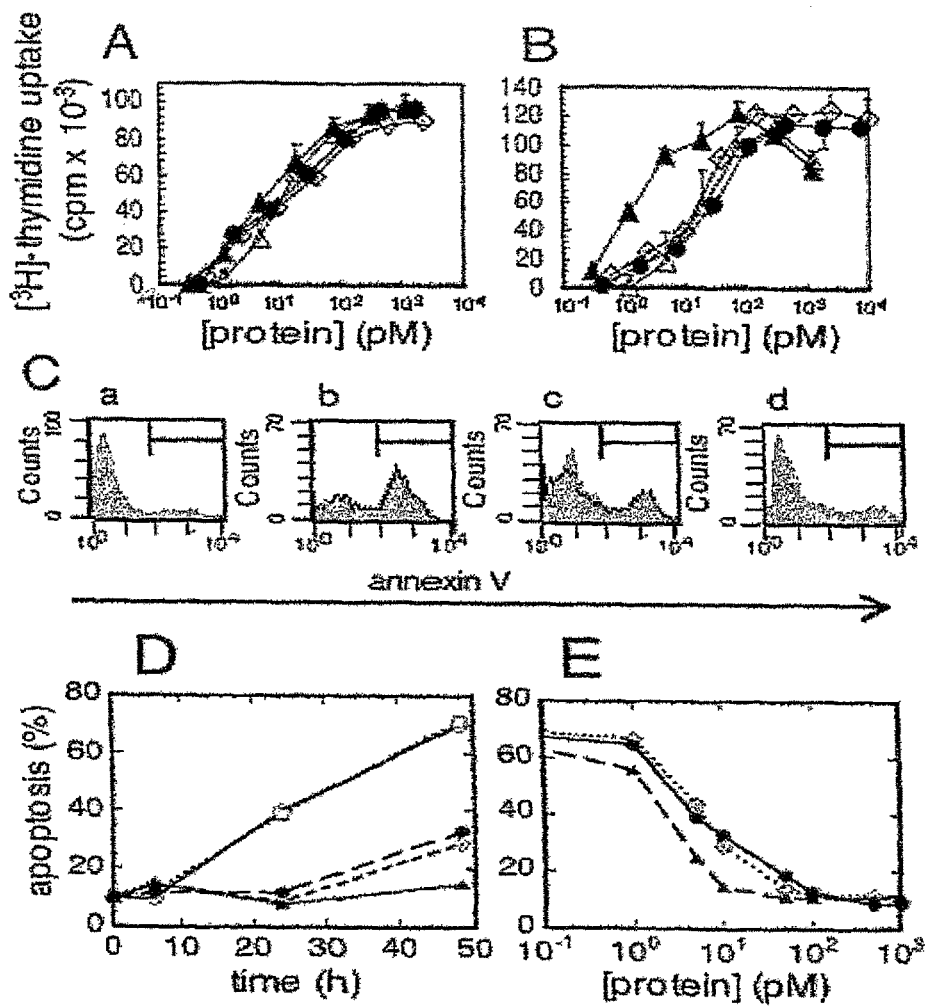
FIG. 5. Effects on IL-15 induced cell proliferation and apoptosis through IL-15Rα/β/γ receptors. [$^3$H]-thymidine incorporation by Kit 225 (△) and TF-1β (B) cells cultured with increasing concentrations of rIL-15 (●), equimolar mixture of rIL-15 and sIL-15Rα-sushi (◇), RLI (▲) or ILR fusion protein (△). (C): Annexin V staining of TF-1β at the beginning of the experiment (Ca), at 48 h after culture without (Cb) or with a fixed concentration of human rIL-15 (500 pM) (Cc), in the absence (full histogram) or presence of sIL-15Rα-sushi protein (10 nM) (unbroken line), or in the presence of 10 pM of RLI (Cd). (D); Kinetics of staining in the absence of exogenous cytokine (○) or in the presence of rIL-15 (10 pM) (●), sIL-15Rα-sushi (10 nM) (□), sIL-15Rα-sushi (10 nM) plus rIL-15 (10 pM) (◇), or RLI fusion protein (10 pM) (▲). (E): Staining at 48 h after culture with increasing concentrations of rIL-15, in the absence (●) or presence (◇) of a fixed concentration (10 nM) of sIL-15Rα-sushi, or with increasing concentrations of RLI fusion protein (▲).

The human lymphoma cell line Kit 225 expresses endogenous IL-15Rα, β and γ chains, and the human TF-1β cell line expresses endogenous IL-15Rα and γ chains plus transfected human IL-15Rβ chain. Consequently, these cell lines proliferate in response to low, picomolar concentrations of IL-15 as shown in FIGS. 5A and 5B (EC50=19 pM and 21 pM respectively). In contrast to what found on Mo-7 or 32Dβ cells, addition of equimolar concentrations of sIL-15Rα-sushi to IL-15 did not significantly affected the IL-15 dose-response curve on either cell type. The ILR fusion protein was as active as rIL-15 on the two cell lines. The RLI was also as active as rIL-15 on Kit 225 cells, but was about 16 fold more efficient (EC50=1.2 pM) than rIL-15 on TF-1β cells.

The effects of sIL-15Rα-sushi and RLI were further analyzed on TF-1β cell apoptosis induced by cytokine deprivation. Histograms are shown in FIG. 5C (graphs a, b, c and d), whereas kinetics and dose responses curves are shown in FIGS. 5D and 5E respectively. rIL-15 dose and time dependently inhibited TF-1β apoptosis. sIL-15Rα-sushi alone had no effect and did not change the effect of IL-15. The ILR fusion protein was as active as rIL-15, whereas RLI had a protecting effect that was about three fold higher than that of rIL-15 (IC50=2.5 pM for RLI instead of 6.5 pM for rIL-15 or sIL-15Rα-sushi plus rIL-15).

IL-15, sIL-15Rα-sushi and RLI Binding to TF1β Cells—

Figures 6A, 6B, 6C, 6D, 6E, 6F:
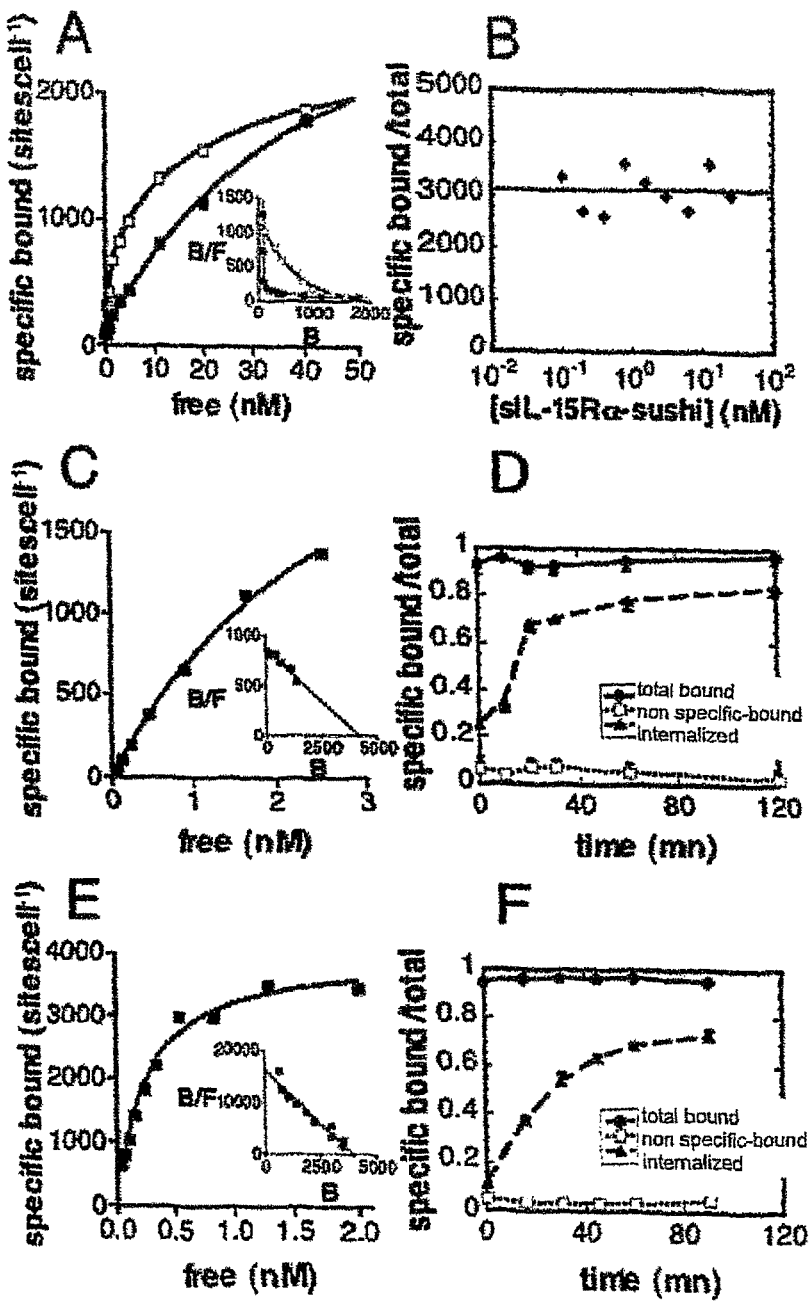
FIG. 6. Binding and internalization of sIL-15Rα-sushi and RLI on TF-1β cells. Effects of sIL-15Rα-sushi on IL-15 binding. (A): Saturation binding curve of $^{125}$I-labeled rIL-15 in the absence (■) or presence of 10 nM sIL-15Rα-sushi (□). (B): Effect of increasing concentrations of sIL-15Rα-sushi on the binding of a fixed concentration of radioiodinated rIL-15 (200 pM). (C): Saturation binding curve of $^{125}$I-labeled sIL-15Rα-sushi in the presence of 1 nM rIL-15 and (D) subsequent internalization. (E): Saturation binding curve of $^{125}$I-labeled RLI and (F) subsequent internalization.

As far as IL-15Rα-sushi did not affect IL-15 proliferation of TF-10, we examined its effect on IL-15 binding that was analyzed on a wide concentration range (FIG. 6A). Scatchard analysis of the saturation binding curve indicated the presence of two classes of IL-15 binding sites, compatible with the presence of a small number of high-affinity binding sites (IL-15Rα/β/γ complexes, Kd=22 pM, Bmax=100 sites/cell) plus higher amounts of intermediate affinity binding sites (IL-15Rβ/γ complexes, Kd=30 nM, 2800 sites/cell). sIL-15Rα-sushi induced an increase of IL-15 binding that, under Scatchard analysis, was mainly due to an increase of the affinity of IL-15 binding for the intermediate-affinity component (Kd=3.5 nM). In order to more specifically test the effect of sIL-15Rα on the high affinity component, its effect was analyzed at low concentrations of radiolabeled IL-15. As shown in FIG. 6B, sIL-15Rα-sushi, at concentrations up to 25 nM, did not affect the IL-15 binding of low concentrations of IL-15 (200 pM) that mainly target the high-affinity receptor (FIG. 6B).

The binding of radiolabeled sIL-15Rα-sushi to TF-1β cells (FIG. 6C) revealed a specific binding component that was strictly dependent on the presence of rIL-15. In the presence of 1 nM rIL-15, the Kd reflecting sIL-15Rα-sushi binding was 3.5 nM, a value compatible with its affinity for IL-15, with a maximal binding capacity (3300 sites/cell) compatible with the number of IL-15 intermediate binding sites. As further shown in FIG. 6D, the radiolabeled sIL-15Rα-sushi was efficiently internalized. Radiolabeled RLI fusion protein also bound to TF1β cells (FIG. 6E). A single specific binding component was observed with a Kd of 250 pM and a maximal capacity (4000 sites/cell) again comparable to the number of IL-15 intermediate affinity binding sites. Once bound, the RLI was also efficiently internalized (FIG. 6F).

Discussion

Deletion of exon 2 of human IL-15Rα was formerly shown to completely abrogate IL-15 binding, indicating the dispensable role of the sushi domain in cytokine recognition (25). The present invention shows that removal of the C-terminal tail (exons 3 to 5) of the extracellular part of IL-15Rα (in the context of the sIL-15Rα-IL-2 fusion protein) results in a 10 fold decrease of its binding affinity for IL-15, as seen by SPR, and a 3.5 fold decrease of its affinity as seen in a competition assay.

In terms of thermodynamics, the 10 fold decrease in affinity was calculated to correspond to a 10% loss of the free energy of interaction of IL-15 with IL-15Rα. Thus the N-terminal structural domain encoded by exon 2 (sushi domain) bears most (90%) but not all of the IL-15 binding capacity. Recent data from our laboratory indicate that domain encoded by exon 3 also contributes to IL-15 binding.

The sIL-15Rα-sushi produced in E. coli had an affinity that was 3 to 4 fold lower than that of sIL-15Rα-sushi-IL-2 produced in CHO cells. This difference cannot be explained by differences in the glycosylation status of the two proteins, as far as the sushi domain does not contain any potential sites for N- or O-linked glycosylations (2). It is therefore likely due to differences in the structural foldings of the two proteins.

While competing with IL-15 binding to membrane IL-15Rα, sIL-15Rα-sushi was found to exert agonist effects by enhancing IL-15 action through the IL-15β/γ complex. Studies on cells expressing either only intermediate affinity IL-15 receptors (Mo-7, 32Dβ) or both high and intermediate affinity IL-15 receptors (TF-1β, Kit 225) showed that the agonist action of sIL-15Rα-sushi was specifically directed to the IL-15Rβ/γ complex: (i) it had no effect in the absence of IL-15, (ii) it bound to TF-1β cells in the presence of IL-15 with a single affinity class of binding sites, the density of which was comparable to that of intermediate IL-15 binding sites, (iii) on Mo-7 cells and TF-1β cells, it increased the affinity of IL-15 for the IL-15Rβ/γ complex whereas it did not affect the binding of IL-15 to the high affinity complex on TF-1β cells, (iv) it enhanced the efficiency of IL-15 biological action (proliferation, prevention from apoptosis) through IL-15Rβ/γ on Mo-7 cells, but had no effect on the same biological effects mediated through the high affinity receptor on TF-1β cells.

The functionality of this agonist action was further supported by the fact that sIL-15Rα-sushi, once bound in conjunction with IL-15 to IL-15Rβ/γ on Mo-7 cells, was efficiently cell internalized. Its potency was strengthened in the context of the ILR and RLI fusion proteins: (i) RLI bound to IL-15Rβ/γ with an affinity almost 20 fold better than IL-15 itself. (ii) binding of RLI was followed by a rapid internalization of the fusion protein. (iii) the RLI or ILR fusion proteins were much more potent than IL-15 in the functional assays. The dose response curves of the two fusion proteins on Mo-7 cells were comparable to those of IL-15 through the high affinity receptor on Kit 225 or TF-1β cells, indicating that these fusion proteins almost fully reconstituted the high affinity response on cells that only express the intermediate affinity receptor.

The results therefore indicate that sIL-15Rα-sushi and IL-15 make a complex that cooperatively increases their binding affinities to the IL-15Rβ/γ receptor. In contrast, sIL-15Rα-sushi is not able to affect IL-15 binding and bioactivity once this latter is already associated with the membrane high affinity receptor complex. Whether sIL-15Rα-sushi can still bind to IL-15 already engaged in this high affinity complex cannot however be excluded and could be tested with the availability of cells expressing mainly high affinity receptor i.e., cells expressing similar levels of the three receptor subunits.

Our laboratory has formerly shown that sIL-15Rα expressed in COS cells or naturally produced by IL-15Rα positive cells, behave as powerful antagonists by binding IL-15 with high affinity (Kd=166 pM) and inhibiting IL-15 induced proliferation of Kit 225 cells at low (IC50 between 3 and 10 pM) concentrations (19). These results are in contrast with the present invention showing that sIL-15Rα-sushi has no effect on the proliferation of Kit 225 cells or of TF-1β cells, and is agonist on Mo-7 cells.

Another contrasting result is a recent report showing that a mixture of rIL-15 with a recombinant human sIL-15Rα (lacking exon 3)-Fc homodimeric chimera could induce an anti-apoptotic effect on Mo-7 cells, whereas rIL-15 alone at the same dose was without effect (26).

Figures 7A, 7B, 7C:
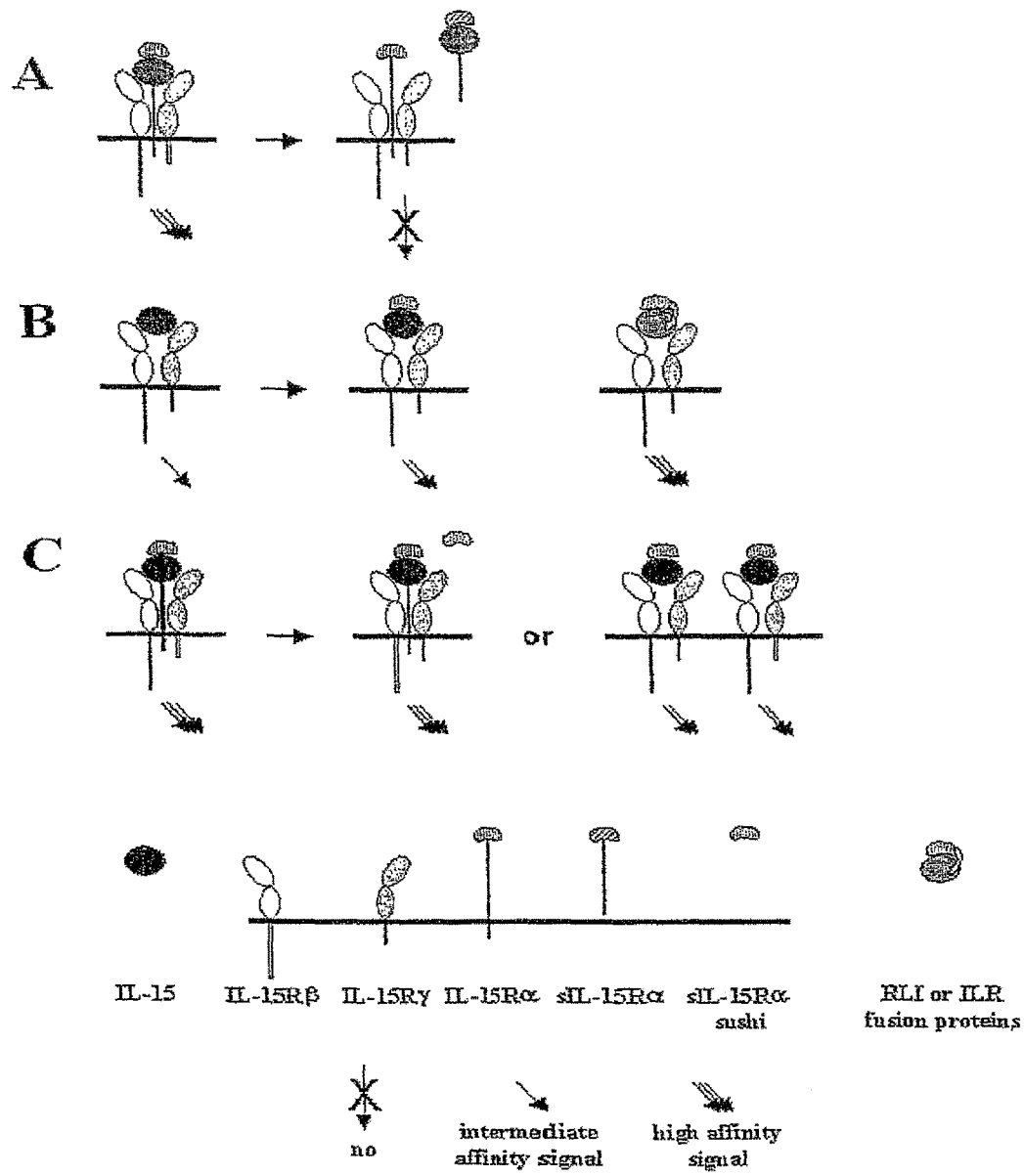
FIG. 7: Proposed models for the differential effects of sIL-15Rα and sIL-15Rα-sushi. (A) In the context of IL-15Rα/β/γ receptors, sIL-15Rα competes with membrane IL-15Rα for binding IL-15. (B) In the context of IL-15Rβ/γ receptors, sIL-15Rα-sushi makes a complex with IL-15 that activates the IL-15Rβ/γ complex more efficiently than IL-15 alone. The RLI or ILR fusion proteins amplify this agonist effect. (C) In the context of IL-15Rα/β/γ receptors, sIL-15Rα-sushi is not efficient in competing with membrane IL-15Rα, or it competes with membrane IL-15Rα and the complex of sIL-15Rα-sushi with IL-15 activates excess IL-15Rβ/γ complexes like in (B).

In an attempt to explain these differences of action, a model is proposed in FIG. 7 of the present patent application. In the context of the high affinity IL-15 response, sIL-15Rα acts as a competitor of membrane IL-15Rα for the recruitment of IL-15 (FIG. 7A). The complex of sIL-15Rα-sushi with IL-15, on the contrary, is able to associate with membrane IL-15Rβ/γ and enhance the biological effect of IL-15 (FIG. 7B). To explain the absence of inhibitory effect of sIL-15Rα-sushi in the context of the high affinity receptor, there are two alternatives (FIG. 7C). According to the first alternative, sIL-15Rα-sushi has a lower affinity for IL-15 (Kd=1.5 nM, this paper) than has sIL-15Rα (Kd=160 pM) (19), and therefore is not be able to efficiently compete with membrane IL-15Rα on Kit 225 or TF-1β cells. According to the second alternative, sIL-15Rα-sushi can compete with membrane IL-15Rα to bind IL-15 and form complexes with IL-15Rβ/γ similar to that formed on Mo-7 cells. Such complexes are less efficient as they need higher concentrations of IL-15 to be activated (IC50=750 pM instead of 20 pM for high affinity receptors, FIGS. 2 and 5). However, given the fact that IL-15Rβ/γ are in excess to IL-15Rα in Kit 225 or TF-1β cells, the lower efficiency of such complexes could be compensated by their higher density (about 3,000 intermediate affinity receptors instead of 100 high affinity receptors on TF-1β cells, cf. FIG. 6). This would result in no observable changes in terms of biological effects. Our observation that sIL-15Rα-sushi does not affect IL-15 high affinity binding on TF-1β cells (FIG. 6B) is however in favor of the first alternative.

The functional differences between sIL-15Rα and sIL-15Rα-sushi indicate that the C terminal tail of sIL-15Rα, plays a crucial role for competing with membrane IL-15Rα and hence for the antagonist action of sIL-15Rα. This tail would either impede soluble IL-15Rα association with IL-15Rβ/γ or allow such an association, but result in an inappropriate conformation of IL-15Rβ/γ for functioning. A similar mechanism has been proposed in the case of a soluble common γ chain (27). The inhibitory activity of this soluble γ chain (corresponding to the entire extracellular part of the γ chain) was abolished by removal of its C-terminal part or by mutations of the WSXVVS motif, two regions not involved in cytokine binding.

The agonist effects of sushi are reminiscent of the agonist effects described for soluble receptors within the extended IL-6 family of cytokines (namely sIL-6R, sIL-11R, sCNTFR and the IL-12p40 subunit) (28). However, such an agonist action in the case of IL-15R could not be anticipated as far as all soluble receptors so far described within the γc family, (sIL-2Rα, sIL-2Rβ, sIL-4R), and sIL-15Rα itself, behave as cytokine antagonists (19, 29), The present results therefore identify the soluble sushi domain of IL-15Rα as an unexpected and efficient agonist within this family.

The concept of cytokine transsignaling has first been used in the case of IL-6, where soluble IL-6R was shown to enhance the sensitivity of IL-6 responsive cells to the action of IL-6 and to render cells that express gp130 but not membrane IL-6R responsive to IL-6 (30). This concept has been extended to other members of the gp130 cytokine family (IL-11R, CNTFR, CLC) (31-34). In the case of IL-15, a mechanism of cytokine transpresentation has been shown (12), in which IL-15 produced by monocytes/dendritic cells is associated to membrane IL-15Rα expressed by the same cells and can stimulate the proliferation of IL-15Rβ/γ$^+$IL-15Rα$^-$ bystander cells. Recent reports have suggested that transpresentation is a dominant mechanism in vivo, that necessitates expression of IL-15 and IL-15Rα by the same cells (13, 14, 35, 36). It has some similarity with the transsignaling concept, in that transpresented IL-15/IL-15Rα. complex can sensitize IL-15Rβ/γ$^+$ IL-15Rα$^-$ cells to physiological concentrations of IL-15. In this respect, membrane IL-15Rα acts as an agonist of IL-15 action by increasing its avidity for the IL-15Rβ/γ complex and the efficiency of signaling (12). Our data show that sIL-15Rα-sushi behaves similarly and sensitizes IL-15Rβ/γ$^+$ IL-15Rα$^-$ cells to the action of IL-15. This suggests that the sushi domain of membrane IL-15Rα is crucial for transpresentation. We have shown that sIL-15Rα produced by IL-15Rα expressing cells and that encompasses the entire extracellular part of IL-15Rα, is inhibitory of IL-15 action (19). It likely constitutes a negative feed-back mechanism that limits the biological effects of IL-15. In contrast, the sIL-15Rα-sushi described in this study displays an agonist effect. If such soluble sushi is generated by IL-15Rα expressing cells, it could participate in the IL-15 transpresentation mechanism. The existence of such naturally produced soluble sushi domains has not yet been described, but is supported by the facts that (i) different isoforms of the membrane IL-15Rα have been described, including some that lack the tail (encoded by exons 3 to 5) linking the sushi domain to the transmembrane domain (3, 25, 37), and (ii) generation of soluble counterparts for some of them by shedding has been demonstrated (19). Thus, sIL-15Rα and sIL-15Rα-sushi could have opposing regulatory effects, and as such both participate in the tuning of the magnitude and duration of IL-15 biological action.

The present invention also shows that using a flexible linker to produce a fusion protein such as ILR or RLI is a valid approach in the case of IL-15. A molecular model of IL-15 with the sushi domain was generated (FIG. 2) that helped to design a flexible linker enabling to link the C-terminus of IL-15 to the N-terminus of sushi (ILR fusion protein) or vice-versa (RLI fusion protein). The model also predicted that the linker was not masking the areas of IL-15 that have been shown to be involved in binding to the IL-15Rβ and γ chains. As discussed above, the two fusion proteins turned out to be much more active than IL-15 and the combination of IL-15 plus sIL-15Rα-sushi in activating the IL-15Rβ/γ complex on Mo-7 cells. On TF-1β cells, and in the context of activation of the high affinity receptor, the ILR fusion protein was as active as IL-15 and the RLI fusion protein was even 10 fold more active, with an EC50 as low as 1.2 pM in inducing cell proliferation. Due to their high activity, these hyper-IL-15 fusion proteins appear to constitute valuable tools for the expansion of lymphocyte subsets, and especially those (NK, CD8 memory T cells) for which transpresentation of IL-15 has been suggested to be the physiological activating process (13). They therefore are very efficient adjuvant molecules in therapeutic strategies aiming at curing patients with cancer, immunodeficiencies, or infectious diseases.

BIBLIOGRAPHIC REFERENCES

1. Grabstein, K. H., Eisenman, J., Shanebeck, K., Rauch, C., Srinivasan, S., Fung, V., Beers, C., Richardson, J., Schoenborn, M. A., Ahdieh, M., and et al. (1994) *Science* 264, 965-968
2. Giri, J. G., Ahdieh, M., Eisenman, J., Shanebeck, K., Grabstein, K., Kumaki, S., Namen, A., Park, L. S., Cosman, D., and Anderson, D. (1994) *Embo J* 13, 2822-2830
3. Anderson, D. M., Kumaki, S., Ahdieh, M., Bertles, J., Tometsko, M., Loomis, A., Giri, J., Copeland, N. G., Gilbert, D. J., Jenkins, N. A., and et al. (1995) *J Biol Chem* 270, 29862-29869
4. Burton, J. D., Bamford, R. N., Peters, C., Grant, A. J., Kurys, G., Goldman, C. K., Brennan, J., Roessler, E., and Waldmann, T. A. (1994) *Proc Natl Acad Sci USA* 91, 4935-4939
5. Carson, W. E., Giri, J. G., Lindemann, M. J., Linett, M. L., Ahdieh, M., Paxton, R., Anderson, D., Eisenmann, J., Grabstein, K., and Caligiuri, M. A. (1994) *J Exp Med* 180, 1395-1403
6. Wilkinson, P. C., and Liew, F. Y. (1995) *J Exp Med* 181, 1255-1259
7. Kennedy, M. K., Glaccum, M., Brown, S. N., Butz, E. A., Viney, J. L., Embers, M., Matsuki, N., Charrier, K., Sedger, L., Willis, C. R., Brasel, K., Morrissey, P. J., Stocking, K., Schuh, J. C., Joyce, S., and Peschon, J. J. (2000) *J Exp Med* 191, 771-780
8. Lodolce, J. P., Burkett, P. R., Boone, D. L., Chien, M., and Ma, A. (2001) *J Exp Med* 194, 1187-1194
9. Marks-Konczalik, J., Dubois, S., Losi, J. M., Sabzevari, H., Yamada, N., Feigenbaum, L., Waldmann, T. A., and Tagaya, Y. (2000) *Proc Natl Acad Sci USA* 97, 11445-11450
10. Ku, C. C., Murakami, M., Sakamoto, A., Kappler, J., and Marrack, P. (2000) *Science* 288, 675-678
11. Li, X. C., Demirci, G., Ferrari-Lacraz, S., Groves, C., Coyle, A., Malek, T. R., and Strom, T. B. (2001) *Nat Med* 7, 114-118
12. Dubois, S., Mariner, J., Waldmann, T. A., and Tagaya, Y. (2002) *Immunity* 17, 537-547
13. Burkett, P. R., Koka, R., Chien, M., Chai, S., Chan, F., Ma, A., and Boone, D. L. (2003) *Proc Natl Acad Sci USA* 100, 4724-4729
14. Schluns, K. S., Nowak, E. C., Cabrera-Hernandez, A., Puddington, L., Lefrancois, L., and Aguila, H. L. (2004) *Proc Natl Acad Sci USA* 101, 5616-5621
15. Kobayashi, H., Dubois, S., Sato, N., Sabzevari, H., Sakai, Y., Waldmann, T. A., and Tagaya, Y. (2005) *Blood* 105, 721-727
16. Norman, D. G., Barlow, P. N., Baron, M., Day, A. J., Sim, R. B., and Campbell, I. D. (1991) *J Mol Biol* 219, 717-725
17. Schulz, O., Sewell, H. F., and Shakib, F. (1998) *J Exp Med* 187, 271-275
18. Sheu, B. C., Hsu, S. M., Ho, H. N., Lien, H. C., Huang, S. C., and Lin, R. H. (2001) *Cancer Res* 61, 237-242
19. Mortier, E., Bernard, J., Plet, A., and Jacques, Y. (2004) *J Immunol* 173, 1681-1688
20. Ruchatz, H., Leung, B. P., Wei, X. Q., McInnes, I. B., and Liew, F. Y. (1998) *J Immunol* 160, 5654-5660
21. Smith, X. G., Bolton, E. M., Ruchatz, H., Wei, X., Liew, F. Y., and Bradley, J. A. (2000) *J Immunol* 165, 3444-3450
22. Farner, N. L., Gan, J., de Jong, J. L., Leary, T. P., Fenske, T. S., Buckley, P., Dunlap, S., and Sondel, P. M. (1997) *Cytokine* 9, 316-327
23. Bernard, J., Harb, C., Mortier, E., Quemener, A., Meloen, R. H., Vermot-Desroches, C., Wijdeness, J., van Dijken, P., Grotzinger, J., Slootstra, J. W., Plet, A., and Jacques, Y. (2004) *J Biol Chem* 279, 24313-24322
24. Matsumoto, M., Misawa, S., Tsumoto, K., Kumagai, I., Hayashi, H., and Kobayashi, Y. (2003) *Protein Expr Purif* 31, 64-71
25. Dubois, S., Magrangeas, F., Lehours, P., Raher, S., Bernard, J., Boisteau, O., Leroy, S., Minvielle, S., Godard, A., and Jacques, Y. (1999) *J Biol Chem* 274, 26978-26984
26. Giron-Michel, J., Giuliani, M., Fogli, M., Brouty-Boye, D., Ferrini, S., Baychelier, F., Eid, P., Lebousse Kerdiles, C., Durali, D., Biassoni, R., Charpentier, B., Vasquez, A., Chouaib, S., Caignard, A., Moretta, L., and Azzarone, B. (2005) *Blood*
27. Meissner, U., Blum, H., Schnare, M., Rollinghoff, M., and Gessner, A. (2001) *Blood* 97, 183-191
28. Jones, S. A., and Rose-John, S. (2002) *Biochim Biophys Acta* 1592, 251-263
29. Heaney, M. L., and Golde, D. W. (1998) *J Leukoc Biol* 64, 135-146
30. Rose-John, S., and Heinrich, P. C. (1994) *Biochem J* 300 (Pt 2), 281-290
31. Pflanz, S., Tacken, I., Grotzinger, J., Jacques, Y., Minvielle, S., Dahmen, H., Heinrich, P. C., and Muller-Newen, G. (1999) *FEBS Lett* 450, 117-122
32. Davis, S., Aldrich, T. H., Ip, N. Y., Stahl, N., Scherer, S., Farruggella, T., DiStefano, P. S., Curtis, R., Panayotatos, N., Gascan, H., and et al. (1993) *Science* 259, 1736-1739
33. Karow, J., Hudson, K. R., Hall, M. A., Vernallis, A. B., Taylor, J. A., Gossler, A., and Heath, J. K. (1996) *Biochem J* 318 (Pt 2), 489-495
34. Elson, G. C., Lelievre, E., Guillet, C., Chevalier, S., Plun-Favreau, H., Froger, J., Suard, I., de Coignac, A. B., Delneste, Y., Bonnefoy, J. Y., Gauchat, J. F., and Gascan, H. (2000) *Nat Neurosci* 3, 867-872
35. Sandau, M. M., Schluns, K. S., Lefrancois, L., and Jameson, S. C. (2004) *J Immunol* 173, 6537-6541
36. Koka, R., Burkett, P. R., Chien, M., Chai, S., Chan, F., Lodolce, J. P., Boone, D. L., and Ma, A. (2003) *J Exp Med* 197, 977-984
37. Bulanova, E., Budagian, V., Orinska, Z., Krause, H., Paus, R., and Bulfone-Paus, S. (2003) *J Immunol* 170, 5045-5055
38. Fischer, M., Goldschmitt, J., Peschel, C., Brakenhoff, J. P., Kallen, K. J., Wollmer, A., Grotzinger, J., and Rose-John, S. (1997) *Nat Biotechnol* 15, 142-145

TABLE 4 list of SEQ ID NO:

| SEQ ID NO: | |
|---|---|
| 1 | hIL-15Ralpha cDNA (1610 bp) |
| 2 | hIL-15Ralpha CDS (83 . . . 883 of SEQ ID NO: 1) |
| 3 | hIL-15Ralpha protein (267 aa) |
| 4 | CDS of hIL-15Ralpha signal peptide (83 . . . 172 of SEQ ID NO :1) |
| 5 | hIL-15Ralpha signal peptide (1 . . . 30 of SEQ ID NO :3) |
| 6 | CDS of mat_peptide of hIL-15Ralpha (173 . . . 883 of SEQ ID NO :1) |
| 7 | mat_peptide of hIL-15Ralpha (31 . . . 267 of SEQ ID NO: 3) |
| 8 | Exon 1 of hIL-15Ralpha (1 . . . 170 of SEQ ID NO: 1) |
| 9 | Exon 2 of hIL-15Ralpha (171 . . . 365 of SEQ ID NO: 1) |
| 10 | Exon 3 of hIL-15Ralpha (366 . . . 464 of SEQ ID NO: 1) |
| 11 | Exon 4 of hIL-15Ralpha (465 . . . 665 of SEQ ID NO: 1) |
| 12 | Exon 5 of hIL-15Ralpha (666 . . . 698 of SEQ ID NO: 1) |
| 13 | CDS of hIL-15Ralpha sushi domain; from C1 to C4 (179 . . . 361 of SEQ ID NO: 1) |
| 14 | hIL-15Ralpha sushi domain; from C1 to C4 (33 . . . 93 of SEQ ID NO: 3) |
| 15 | CDS of [it + hIL-15Ralpha sushi domain] (173 . . . 361 of SEQ ID NO: 1) |
| 16 | [it + hIL-15Ralpha sushi domain] (31 . . . 93 of SEQ ID NO: 3) |
| 17 | CDS of [t + hIL-15Ralpha sushi domain] (176 . . . 361 of SEQ ID NO: 1) |
| 18 | [t + hIL-15Ralpha sushi domain] (32 . . . 93 of SEQ ID NO: 3) |
| 19 | CDS of hIL15-Ralpha hinge region (362. . . 403 of SEQ ID NO: 1) |
| 20 | hIL15-Ralpha hinge region (94 . . . 107 of SEQ ID NO: 3; irdpalvhqrpapp) |
| 21 | CDS of [hIL-15Ralpha sushi domain + i] (179 . . . 364 of SEQ ID NO: 1) |
| 22 | [hIL-15Ralpha sushi domain + i] (33 . . . 94 of SEQ ID NO: 3) |
| 23 | CDS of [it + hIL-15Ralpha sushi domain + 30 i] (173 . . . 364 of SEQ ID NO: 1) |
| 24 | [it + hIL-15Ralpha sushi domain + i] (31 . . . 94 of SEQ ID NO: 3) |
| 25 | CDS of [t + hIL-15Ralpha sushi domain + i] (176 . . . 364 of SEQ ID NO: 1) |
| 26 | [t + hIL-15Ralpha sushi domain + i] (32 . . . 94 of SEQ ID NO: 3) |
| 27 | CDS of [it + hIL-15Ralpha sushi domain + i + rd] (173 . . . 370 of SEQ ID NO: 1) |
| 28 | [it + hIL-15Ralpha sushi domain + i + rd] (31 . . . 96 of SEQ ID NO: 3) |
| 29 | CDS of [it + hIL-15Ralpha sushi domain + i + rd + 11 exon3-encoded aa] (173 . . . 403 of SEQ ID NQ: 1) |
| 30 | [it + hIL-15Ralpha sushi domain + i + rd + 11 exon3-encoded aa] (31 . . . 107 of SEQ ID NO: 3) |
| 31 | CDS of region rich in glycosylation sites of hIL-15Ralpha (404 . . . 709 of SEQ ID NO: 1) |
| 32 | Region rich in glycosylation sites of hIL-15Ralpha (108 . . . 209 of SEQ ID NO: 3) |
| 33 | sequence coding for the exon3-encoded part of the region rich in glycosylation sites of human IL-15Ralpha (404 . . . 464 of SEQ ID NO: 1) |
| 34 | Exon3-encoded part of the region rich in glycosylation sites of human IL-15Ralpha (108 . . . 127 of SEQ ID NO: 3) |

TABLE 4-continued list of SEQ ID NO:

| SEQ ID NO: | |
|---|---|
| 35 | CDS of [it + hIL-15Ralpha sushi domain + i + all exon3-encoded aa] (173 . . . 464 of SEQ ID NO: 1) |
| 36 | [it + hIL-15Ralpha sushi domain + i + all exon3-encoded aa] (31 . . . 127 of SEQ ID NO: 3) |
| 37 | CDS of a fragment of a soluble extracellular hIL-15Ralpha (83 . . . 697 of SEQ ID NO: 1) |
| 38 | fragment of a soluble extracellular hIL-15Ralpha (1 . . . 205 of SEQ ID NO: 3) |
| 39 | CDS of a soluble extracellular hIL-15Ralpha (83 . . . 709 of SEQ ID NO: 1) |
| 40 | a soluble extracellular hIL-15Ralpha (1 . . . 209 of SEQ ID NO: 3) |
| 41 | CDS of a fragment of a soluble, signal peptide deleted, extracellular hIL-15Ralpha (173 . . . 697 of SEQ ID NO: 1) |
| 42 | fragment of a soluble, signal peptide deleted, extracellular hIL-15Ralpha (31 . . . 205 of SEQ ID NO: 3) |
| 43 | CDS of a soluble, signal peptide deleted, extracellular hIL-15Ralpha (173 . . . 709 of SEQ ID NO: 1) |
| 44 | A soluble, signal peptide deleted, extracellular hIL-15Ralpha (31 . . . 209 of SEQ ID NO: 3) |
| 45 | hIL-15 cDNA (1496 bp) |
| 46 | hIL-15 precursor protein (162 aa) |
| 47 | CDS of mature wild-type hIL-15 (517 . . . 858 of SEQ ID NO: 45) |
| 48 | mature wild-type hIL-15 (49 . . . 162 of SEQ ID NO: 46) |
| 49 | Nucleic acid sequence of linker 20 |
| 50 | Amino acid sequence of linker 20 |
| 51 | Nucleic acid sequence of linker 26 |
| 52 | Amino acid sequence of linker 26 |
| 53 | Nucleic acid sequence of Flag tag and Xa binding site |
| 54 | Amino acid sequence of Flag tag and Xa binding site |
| 55 | Nucleic acid sequence of Flag tag and Xa binding site |
| 56 | Amino acid sequence of Flag tag and Xa binding site |
| 57 | CDS of bovine preprolactine signal peptide |
| 58 | bovine preprolactine signal peptide |
| 59 | Nucleic acid sequence of RLI fusion protein |
| 60 | RLI fusion protein |
| 61 | Nucleic acid sequence of ILR fusion protein |
| 62 | ILR fusion protein |
| 63 | hIL-2 cDNA (1047 bp) |
| 64 | CDS of mature hIL-2 (355 . . . 753 of SEQ ID NO: 63) |
| 65 | mature hIL-2 (133 aa) |
| 66 | Nucleic acid sequence of a sushi-containing hIL-15Ralpha fragment, tagged with IL-2 [signal peptide of hIL-15Ralpha + it + hIL-15Ralpha sushi domain + i + rd + linker lq + hIL-2] |

TABLE 4-continued list of SEQ ID NO:

| SEQ ID NO: | |
|---|---|
| 67 | sushi-containing hIL-15Ralpha fragment, tagged with IL-2 [signal peptide of hIL-15Ralpha + it + hIL-15Ralpha sushi domain + i + rd + linker lq + hIL-2] |
| 68 | Nucleic acid sequence of a fragment of extracellular hIL-15Ralpha, tagged with IL-2 [signal peptide of hIL-15Ralpha + fragment of extracellular region of hIL-15Ralpha + linker lq + hIL-2] |
| 69 | Fragment of extracellular hIL-15Ralpha, tagged with IL-2 [signal peptide of hIL-15Ralpha + fragment of extracellular region of hIL-15Ralpha + linker lq + hIL-2] |
| 70 | Beta chain sense primer (GAGAGACTGGATGGACCC) |
| 71 | Beta chain reverse primer (AAGAAACTAACTCTTAAAGAGGC) |
| 72 | Mouse (*Mus musculus*) IL-15Ralpha cDNA (792 bp) |
| 73 | Mouse IL-15Ralpha protein (263 aa) |
| 74 | Mouse IL-15Ralpha extracellular region (1 . . . 205 of SEQ ID NO: 73) |
| 75 | Mouse IL-15Ralpha sushi domain (36 . . . 96 of SEQ ID NO: 73) |
| 76 | Mouse IL-15Ralpha hinge region (97 . . . 109 of SEQ ID NO: 73) |
| 77 | Mouse IL-15Ralpha tail region (110 . . . 205 of SEQ ID NO: 73) |
| 78 | Chimpanzee (*Pan troglodytes*) IL-15Ralpha cDNA (1035 bp) |
| 79 | Chimpanzee IL-15Ralpha protein (344 aa) |
| 80 | Chimpanzee IL-15Ralpha extracellular region (1 . . . 286 of SEQ ID NO: 79) |
| 81 | Chimpanzee IL-15Ralpha sushi domain (13 . . . 73 of SEQ ID NO: 79) |
| 82 | Chimpanzee IL-15Ralpha hinge region (74 . . . 88 of SEQ ID NO: 79) |
| 83 | Chimpanzee IL-15Ralpha tail region (89 . . . 286 of SEQ ID NO: 79) |
| 84 | *Rattus norvegicus* IL-15Ralpha cDNA (765 bp) |
| 85 | *Rattus norvegicus* IL-15Ralpha protein (254 aa) |
| 86 | *Rattus norvegicus* IL-15Ralpha extracellular region (1 . . . 182 of SEQ ID NO: 85) |
| 87 | *Rattus norvegicus* IL-15Ralpha sushi domain (24 . . . 84 of SEQ ID NO: 85) |
| 88 | *Rattus norvegicus* IL-15Ralpha hinge region (85 . . . 96 of SEQ ID NO: 85) |
| 89 | *Rattus norvegicus* IL-15Ralpha tail region (97 . . . 182 of SEQ ID NO: 85) |
| 90 | Exon 3 of *Mus musculus* IL-15Ralpha |
| 91 | Exon 3 of *pan troglodytes* IL-15Ralpha |
| 92 | Exon 3 of *Rattus norvegicus* IL-15Ralpha |
| 93 | Exon 3 encoded part of human IL-15Ralpha |
| 94 | Exon 3 encoded part of *Mus musculus* IL-15Ralpha |
| 95 | Exon 3 encoded part of *Pan troglodytes* IL-15Ralpha |
| 96 | Exon 3 encoded part of *Rattus norvegicus* IL-15Ralpha |
| 97 | Exon 2 encoded part of *Mus musculus* IL-15Ralpha |
| 98 | Exon 2 encoded part of *Pan troglodytes* IL-15Ralpha |
| 99 | Exon 2 encoded part of *Rattus norvegicus* IL-15Ralpha |

TABLE 4-continued list of SEQ ID NO:

| SEQ ID NO: | |
|---|---|
| 100 | Sense primer for gamma chain (5' GAAGAGCAAG CGCCATGTTG 3') |
| 101 | Antisense primer for gamma chain (5' TCAGGTTTCAGGCTTTAGGG 3') | hIL-15Ralpha = human IL-15Ralpha
hIL-2 = human IL-2

The invention claimed is:

1. A fusion protein comprising an IL-15Rα sushi domain and an IL-15, which are joined by a flexible linker consisting of the amino acid sequence of SEQ ID NO:50, wherein the fusion protein is an IL-15 agonist.

2. The fusion protein of claim 1, wherein the IL-15 receptor alpha IL-15Rα sushi domain polypeptide consists of the amino acid sequence of SEQ ID NO: 14.

3. The fusion protein of claim 1, wherein the IL-15 is a human IL-15.

4. A pharmaceutical composition comprising the fusion protein of claim 1 and a pharmaceutically acceptable carrier.

5. A fusion protein comprising an IL-15Rα sushi domain and an IL-15, which are joined by a flexible linker consisting of the amino acid sequence of SEQ ID NO: 52, wherein the fusion protein is an IL-15 agonist.

6. The fusion protein of claim 5, wherein the IL-15 receptor alpha IL-15Rα sushi domain polypeptide consists of the amino acid sequence of SEQ ID NO: 14.

7. The fusion protein of claim 5, wherein the IL-15 is a human IL-15.

8. A pharmaceutical composition comprising the fusion protein of claim 5 and a pharmaceutically acceptable carrier.

9. A fusion protein comprising a human IL-15Rα sushi domain and a human IL-15, wherein the fusion protein comprises the amino acid sequence of SEQ ID NO:60.

10. A pharmaceutical composition comprising the fusion protein of claim 9 and a pharmaceutically acceptable carrier.

* * * * *

SEQUENCE LISTING

<160> NUMBER OF SEQ ID NOS: 101

<210> SEQ ID NO 1
<211> LENGTH: 1610
<212> TYPE: DNA
<213> ORGANISM: Homo sapiens

<400> SEQUENCE: 1

```
cccagagcag cgctcgccac ctccccccgg cctgggcagc gctcgcccgg ggagtccagc      60
ggtgtcctgt ggagctgccg ccatggcccc gcggcgggcg cgcggctgcc ggaccctcgg     120
tctcccggcg ctgctactgc tgctgctgct ccggccgccg gcgacgcggg gcatcacgtg     180
ccctccccccc atgtccgtgg aacacgcaga catctgggtc aagagctaca gcttgtactc     240
cagggagcgg tacatttgta actctggttt caagcgtaaa gccggcacgt ccagcctgac     300
ggagtgcgtg ttgaacaagg ccacgaatgt cgcccactgg acaacccccca gtctcaaatg     360
cattagagac cctgccctgg ttcaccaaag gccagcgcca ccctccacag taacgacggc     420
aggggtgacc ccacagccag agagcctctc cccttctgga aaagagcccg cagcttcatc     480
tcccagctca aacaacacag cggccacaac agcagctatt gtcccgggct cccagctgat     540
gccttcaaaa tcaccttcca caggaaccac agagataagc agtcatgagt cctcccacgg     600
cacccccctct cagacaacag ccaagaactg ggaactcaca gcatccgcct ccaccagcc     660
gccaggtgtg tatccacagg gccacagcga caccactgtg gctatctcca cgtccactgt     720
cctgctgtgt gggctgagcg ctgtgtctct cctggcatgc tacctcaagt caaggcaaac     780
tcccccgctg gccagcgttg aaatggaagc catggaggct ctgccggtga cttggggggac     840
cagcagcaga gatgaagact ggaaaactg ctctcaccac ctatgaaact cggggaaacc     900
agcccagcta agtccggagt gaaggagcct ctctgcttta gctaaagacg actgagaaga     960
ggtgcaagga agcgggctcc aggagcaagc tcaccaggcc tctcagaagt cccagcagga    1020
tctcacggac tgccgggtcg gcgcctcctg cgcgagggag caggttctcc gcattcccat    1080
gggcaccacc tgcctgcctg tcgtgccttg gacccagggc ccagcttccc aggagagacc    1140
aaaggcttct gagcaggatt tttatttcat tacagtgtga gctgcctgga atacatgtgg    1200
taatgaaata aaaaccctgc cccgaatctt ccgtccctca tcctaacttg cagttcacag    1260
agaaaagtga catacccaaa gctctctgtc aattacaagg cttctcctgg cgtgggagac    1320
gtctacaggg aagacaccag cgtttgggct tctaaccacc ctgtctccag ctgctctgca    1380
cacatggaca gggacctggg aaaggtggga gagatgctga gccagcgaa tcctctccat    1440
tgaaggattc aggaagaaga aaactcaact cagtgccatt ttacgaatat atgcgtttat    1500
atttatactt ccttgtctat tatatctata cattatatat tatttgtatt ttgacattgt    1560
```

-continued

```
accttgtata aacaaaataa aacatctatt ttcaatattt ttaaaatgca          1610
```

<210> SEQ ID NO 2
<211> LENGTH: 801
<212> TYPE: DNA
<213> ORGANISM: Homo sapiens

<400> SEQUENCE: 2

```
atggccccgc ggcgggcgcg cggctgccgg accctcggtc tcccggcgct gctactgctg     60
ctgctgctcc ggccgccggc gacgcggggc atcacgtgcc ctcccccat  gtccgtggaa    120
cacgcagaca tctgggtcaa gagctacagc ttgtactcca gggagcggta catttgtaac    180
tctggtttca gcgtaaagc  cggcacgtcc agcctgacgg agtgcgtgtt gaacaaggcc    240
acgaatgtcg cccactggac aaccccccagt ctcaaatgca ttagagaccc tgccctggtt   300
caccaaaggc cagcgccacc ctccacagta acgacggcag gggtgacccc acagccagag    360
agcctctccc cttctggaaa agagcccgca gcttcatctc ccagctcaaa caacacagcg    420
gccacaacag cagctattgt cccgggctcc cagctgatgc cttcaaaatc accttccaca    480
ggaaccacag agataagcag tcatgagtcc tcccacggca ccccctctca gacaacagcc    540
aagaactggg aactcacagc atccgcctcc caccagccgc caggtgtgta tccacagggc    600
cacagcgaca ccactgtggc tatctccacg tccactgtcc tgctgtgtgg gctgagcgct    660
gtgtctctcc tggcatgcta cctcaagtca aggcaaactc ccccgctggc cagcgttgaa    720
atggaagcca tggaggctct gccggtgact tgggggacca gcagcagaga tgaagacttg    780
gaaaactgct ctcaccacct a                                              801
```

<210> SEQ ID NO 3
<211> LENGTH: 267
<212> TYPE: PRT
<213> ORGANISM: Homo sapiens

<400> SEQUENCE: 3

```
Met Ala Pro Arg Arg Ala Arg Gly Cys Arg Thr Leu Gly Leu Pro Ala
1               5                   10                  15

Leu Leu Leu Leu Leu Leu Leu Arg Pro Ala Thr Arg Gly Ile Thr
                20                  25                  30

Cys Pro Pro Pro Met Ser Val Glu His Ala Asp Ile Trp Val Lys Ser
                35                  40                  45

Tyr Ser Leu Tyr Ser Arg Glu Arg Tyr Ile Cys Asn Ser Gly Phe Lys
            50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
                100                 105                 110

Ala Gly Val Thr Pro Gln Pro Glu Ser Leu Ser Pro Ser Gly Lys Glu
            115                 120                 125

Pro Ala Ala Ser Ser Pro Ser Ser Asn Asn Thr Ala Ala Thr Thr Ala
130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175
```

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265

<210> SEQ ID NO 4
<211> LENGTH: 90
<212> TYPE: DNA
<213> ORGANISM: Homo sapiens

<400> SEQUENCE: 4
atggccccgc ggcgggcgcg cggctgccgg accctcggtc tcccggcgct gctactgctg    60
ctgctgctcc ggccgccggc gacgcggggc                                     90

<210> SEQ ID NO 5
<211> LENGTH: 30
<212> TYPE: PRT
<213> ORGANISM: Homo sapiens

<400> SEQUENCE: 5

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly
            20                  25                  30

<210> SEQ ID NO 6
<211> LENGTH: 711
<212> TYPE: DNA
<213> ORGANISM: Homo sapiens

<400> SEQUENCE: 6
atcacgtgcc ctcccccat gtccgtggaa cacgcagaca tctgggtcaa gagctacagc    60
ttgtactcca gggagcggta catttgtaac tctggtttca agcgtaaagc cggcacgtcc    120
agcctgacgg agtgcgtgtt gaacaaggcc acgaatgtcg cccactggac aaccccagt    180 ctcaaatgca ttagagaccc tgccctggtt caccaaaggc cagcgccacc ctccacagta    240
acgacggcag gggtgacccc acagccagag agcctctccc cttctggaaa agagcccgca    300
gcttcatctc ccagctcaaa caacacagcg gccacaacag cagctattgt cccgggctcc    360
cagctgatgc cttcaaaatc accttccaca ggaaccacag agataagcag tcatgagtcc    420
tcccacggca ccccctctca gacaacagcc aagaactggg aactcacagc atccgcctcc    480
caccagccgc aggtgtgta tccacagggc acagcgaca ccactgtggc tatctccacg    540
tccactgtcc tgctgtgtgg gctgagcgct gtgtctctcc tggcatgcta cctcaagtca    600
aggcaaactc ccccgctggc cagcgttgaa atggaagcca tggaggctct gccggtgact    660
tgggggacca gcagcagaga tgaagacttg gaaaactgct ctcaccacct a              711

<210> SEQ ID NO 7
<211> LENGTH: 237

<212> TYPE: PRT
<213> ORGANISM: Homo sapiens

<400> SEQUENCE: 7

```
Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr Val
                165                 170                 175

Ala Ile Ser Thr Ser Thr Val Leu Leu Cys Gly Leu Ser Ala Val Ser
            180                 185                 190

Leu Leu Ala Cys Tyr Leu Lys Ser Arg Gln Thr Pro Pro Leu Ala Ser
        195                 200                 205

Val Glu Met Glu Ala Met Glu Ala Leu Pro Val Thr Trp Gly Thr Ser
    210                 215                 220

Ser Arg Asp Glu Asp Leu Glu Asn Cys Ser His His Leu
225                 230                 235
```

<210> SEQ ID NO 8
<211> LENGTH: 170
<212> TYPE: DNA
<213> ORGANISM: Homo sapiens

<400> SEQUENCE: 8

```
cccagagcag cgctcgccac ctcccccgg cctgggcagc gctcgcccgg ggagtccagc     60
ggtgtcctgt ggagctgccg ccatggcccc gcggcgggcg cgcggctgcc ggaccctcgg    120
tctcccggcg ctgctactgc tgctgctgct ccggccgccg gcgacgcggg                170
```

<210> SEQ ID NO 9
<211> LENGTH: 195
<212> TYPE: DNA
<213> ORGANISM: Homo sapiens

<400> SEQUENCE: 9

```
gcatcacgtg ccctcccccc atgtccgtgg aacacgcaga catctgggtc aagagctaca     60
gcttgtactc cagggagcgg tacatttgta actctggttt caagcgtaaa gccggcacgt    120
ccagcctgac ggagtgcgtg ttgaacaagg ccacgaatgt cgcccactgg acaaccccca    180
gtctcaaatg catta                                                     195
```

<210> SEQ ID NO 10
<211> LENGTH: 99
<212> TYPE: DNA
<213> ORGANISM: Homo sapiens

<400> SEQUENCE: 10
gagaccctgc cctggttcac caaaggccag cgccaccctc acagtaacg acggcagggg        60 tgacccaca gccagagagc ctctcccctt ctggaaaag                               99

<210> SEQ ID NO 11
<211> LENGTH: 201
<212> TYPE: DNA
<213> ORGANISM: Homo sapiens

<400> SEQUENCE: 11
agcccgcagc ttcatctccc agctcaaaca acacagcggc cacaacagca gctattgtcc        60
cgggctccca gctgatgcct tcaaaatcac cttccacagg aaccacagag ataagcagtc       120
atgagtcctc ccacggcacc ccctctcaga caacagccaa gaactgggaa ctcacagcat       180
ccgcctccca ccagccgcca g                                                 201

<210> SEQ ID NO 12
<211> LENGTH: 33
<212> TYPE: DNA
<213> ORGANISM: Homo sapiens

<400> SEQUENCE: 12
gtgtgtatcc acagggccac agcgacacca ctg                                    33

<210> SEQ ID NO 13
<211> LENGTH: 183
<212> TYPE: DNA
<213> ORGANISM: Homo sapiens

<400> SEQUENCE: 13
tgccctcccc ccatgtccgt ggaacacgca gacatctggg tcaagagcta cagcttgtac        60
tccagggagc ggtacatttg taactctggt ttcaagcgta aagccggcac gtccagcctg       120
acggagtgcg tgttgaacaa ggccacgaat gtcgcccact ggacaacccc cagtctcaaa       180
tgc                                                                    183

<210> SEQ ID NO 14
<211> LENGTH: 61
<212> TYPE: PRT
<213> ORGANISM: Homo sapiens

<400> SEQUENCE: 14

Cys Pro Pro Pro Met Ser Val Glu His Ala Asp Ile Trp Val Lys Ser
1               5                   10                  15

Tyr Ser Leu Tyr Ser Arg Glu Arg Tyr Ile Cys Asn Ser Gly Phe Lys
            20                  25                  30

Arg Lys Ala Gly Thr Ser Ser Leu Thr Glu Cys Val Leu Asn Lys Ala
        35                  40                  45

Thr Asn Val Ala His Trp Thr Thr Pro Ser Leu Lys Cys
    50                  55                  60

<210> SEQ ID NO 15
<211> LENGTH: 189
<212> TYPE: DNA

<213> ORGANISM: Homo sapiens

<400> SEQUENCE: 15

```
atcacgtgcc ctcccccat gtccgtggaa cacgcagaca tctgggtcaa gagctacagc      60
ttgtactcca gggagcggta catttgtaac tctggtttca agcgtaaagc cggcacgtcc     120
agcctgacgg agtgcgtgtt gaacaaggcc acgaatgtcg cccactggac aaccccagt     180
ctcaaatgc                                                            189
```

<210> SEQ ID NO 16
<211> LENGTH: 63
<212> TYPE: PRT
<213> ORGANISM: Homo sapiens

<400> SEQUENCE: 16

Ile Thr Cys Pro Pro Pro Met Ser Val Glu His Ala Asp Ile Trp Val
1               5                   10                  15
Lys Ser Tyr Ser Leu Tyr Ser Arg Glu Arg Tyr Ile Cys Asn Ser Gly
            20                  25                  30
Phe Lys Arg Lys Ala Gly Thr Ser Ser Leu Thr Glu Cys Val Leu Asn
        35                  40                  45
Lys Ala Thr Asn Val Ala His Trp Thr Thr Pro Ser Leu Lys Cys
    50                  55                  60

<210> SEQ ID NO 17
<211> LENGTH: 186
<212> TYPE: DNA
<213> ORGANISM: Homo sapiens

<400> SEQUENCE: 17

```
acgtgccctc cccccatgtc cgtggaacac gcagacatct gggtcaagag ctacagcttg      60
tactccaggg agcggtacat ttgtaactct ggtttcaagc gtaaagccgg cacgtccagc     120
ctgacggagt gcgtgttgaa caaggccacg aatgtcgccc actggacaac ccccagtctc     180
aaatgc                                                                186
```

<210> SEQ ID NO 18
<211> LENGTH: 62
<212> TYPE: PRT
<213> ORGANISM: Homo sapiens

<400> SEQUENCE: 18

Thr Cys Pro Pro Pro Met Ser Val Glu His Ala Asp Ile Trp Val Lys
1               5                   10                  15
Ser Tyr Ser Leu Tyr Ser Arg Glu Arg Tyr Ile Cys Asn Ser Gly Phe
            20                  25                  30
Lys Arg Lys Ala Gly Thr Ser Ser Leu Thr Glu Cys Val Leu Asn Lys
        35                  40                  45
Ala Thr Asn Val Ala His Trp Thr Thr Pro Ser Leu Lys Cys
    50                  55                  60

<210> SEQ ID NO 19
<211> LENGTH: 42
<212> TYPE: DNA
<213> ORGANISM: Homo sapiens

<400> SEQUENCE: 19

```
attagagacc ctgccctggt tcaccaaagg ccagcgccac cc                         42
```

```
<210> SEQ ID NO 20
<211> LENGTH: 14
<212> TYPE: PRT
<213> ORGANISM: Homo sapiens

<400> SEQUENCE: 20

Ile Arg Asp Pro Ala Leu Val His Gln Arg Pro Ala Pro Pro
1               5                   10

<210> SEQ ID NO 21
<211> LENGTH: 186
<212> TYPE: DNA
<213> ORGANISM: Homo sapiens

<400> SEQUENCE: 21
tgccctcccc ccatgtccgt ggaacacgca gacatctggg tcaagagcta cagcttgtac      60
tccagggagc ggtacatttg taactctggt ttcaagcgta aagccggcac gtccagcctg     120
acggagtgcg tgttgaacaa ggccacgaat gtcgcccact ggacaacccc cagtctcaaa     180
tgcatt                                                                186

<210> SEQ ID NO 22
<211> LENGTH: 62
<212> TYPE: PRT
<213> ORGANISM: Homo sapiens

<400> SEQUENCE: 22

Cys Pro Pro Pro Met Ser Val Glu His Ala Asp Ile Trp Val Lys Ser
1               5                   10                  15

Tyr Ser Leu Tyr Ser Arg Glu Arg Tyr Ile Cys Asn Ser Gly Phe Lys
                20                  25                  30

Arg Lys Ala Gly Thr Ser Ser Leu Thr Glu Cys Val Leu Asn Lys Ala
            35                  40                  45

Thr Asn Val Ala His Trp Thr Thr Pro Ser Leu Lys Cys Ile
        50                  55                  60

<210> SEQ ID NO 23
<211> LENGTH: 192
<212> TYPE: DNA
<213> ORGANISM: Homo sapiens

<400> SEQUENCE: 23
atcacgtgcc ctcccccat gtccgtggaa cacgcagaca tctgggtcaa gagctacagc       60
ttgtactcca gggagcggta catttgtaac tctggtttca agcgtaaagc cggcacgtcc     120
agcctgacgg agtgcgtgtt gaacaaggcc acgaatgtcg cccactggac aaccccagt     180 ctcaaatgca tt                                                         192

<210> SEQ ID NO 24
<211> LENGTH: 64
<212> TYPE: PRT
<213> ORGANISM: Homo sapiens

<400> SEQUENCE: 24

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45
```

Lys Ala Thr Asn Val Ala His Trp Thr Thr Pro Ser Leu Lys Cys Ile
    50                  55                  60

<210> SEQ ID NO 25
<211> LENGTH: 189
<212> TYPE: DNA
<213> ORGANISM: Homo sapiens

<400> SEQUENCE: 25
acgtgccctc cccccatgtc cgtggaacac gcagacatct gggtcaagag ctacagcttg      60
tactccaggg agcggtacat ttgtaactct ggtttcaagc gtaaagccgg cacgtccagc     120
ctgacggagt gcgtgttgaa caaggccacg aatgtcgccc actggacaac ccccagtctc     180
aaatgcatt                                                             189

<210> SEQ ID NO 26
<211> LENGTH: 63
<212> TYPE: PRT
<213> ORGANISM: Homo sapiens

<400> SEQUENCE: 26

Thr Cys Pro Pro Pro Met Ser Val Glu His Ala Asp Ile Trp Val Lys
1               5                   10                  15

Ser Tyr Ser Leu Tyr Ser Arg Glu Arg Tyr Ile Cys Asn Ser Gly Phe
            20                  25                  30

Lys Arg Lys Ala Gly Thr Ser Ser Leu Thr Glu Cys Val Leu Asn Lys
        35                  40                  45

Ala Thr Asn Val Ala His Trp Thr Thr Pro Ser Leu Lys Cys Ile
    50                  55                  60

<210> SEQ ID NO 27
<211> LENGTH: 198
<212> TYPE: DNA
<213> ORGANISM: Homo sapiens

<400> SEQUENCE: 27
atcacgtgcc ctcccccat gtccgtggaa cacgcagaca tctgggtcaa gagctacagc       60
ttgtactcca gggagcggta catttgtaac tctggtttca agcgtaaagc cggcacgtcc     120
agcctgacgg agtgcgtgtt gaacaaggcc acgaatgtcg cccactggac aaccccagt     180 ctcaaatgca ttagagac                                                   198

<210> SEQ ID NO 28
<211> LENGTH: 66
<212> TYPE: PRT
<213> ORGANISM: Homo sapiens

<400> SEQUENCE: 28

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp
65

<210> SEQ ID NO 29
<211> LENGTH: 231
<212> TYPE: DNA
<213> ORGANISM: Homo sapiens

<400> SEQUENCE: 29

```
atcacgtgcc ctcccccat gtccgtggaa cacgcagaca tctgggtcaa gagctacagc      60
ttgtactcca gggagcggta catttgtaac tctggtttca gcgtaaagc cggcacgtcc     120
agcctgacgg agtgcgtgtt gaacaaggcc acgaatgtcg cccactggac aaccccagt    180
ctcaaatgca ttgagacccc tgccctggtt caccaaaggc cagcgccacc c             231
```

<210> SEQ ID NO 30
<211> LENGTH: 77
<212> TYPE: PRT
<213> ORGANISM: Homo sapiens

<400> SEQUENCE: 30

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro
65                  70                  75

<210> SEQ ID NO 31
<211> LENGTH: 306
<212> TYPE: DNA
<213> ORGANISM: Homo sapiens

<400> SEQUENCE: 31

```
tccacagtaa cgacggcagg ggtgacccca cagccagaga gcctctcccc ttctggaaaa      60
gagcccgcag cttcatctcc cagctcaaac aacacagcgg ccacaacagc agctattgtc     120
ccgggctccc agctgatgcc ttcaaaatca ccttccacag gaaccacaga gataagcagt    180
catgagtcct cccacggcac ccctctcag acaacagcca gaactggga actcacagca     240
tccgcctccc accagccgcc aggtgtgtat ccacagggcc acagcgacac cactgtggct    300
atctcc                                                                306
```

<210> SEQ ID NO 32
<211> LENGTH: 102
<212> TYPE: PRT
<213> ORGANISM: Homo sapiens

<400> SEQUENCE: 32

Ser Thr Val Thr Thr Ala Gly Val Thr Pro Gln Pro Glu Ser Leu Ser
1               5                   10                  15

Pro Ser Gly Lys Glu Pro Ala Ala Ser Ser Pro Ser Ser Asn Asn Thr
            20                  25                  30

Ala Ala Thr Thr Ala Ala Ile Val Pro Gly Ser Gln Leu Met Pro Ser
        35                  40                  45

Lys Ser Pro Ser Thr Gly Thr Thr Glu Ile Ser Ser His Glu Ser Ser
    50                  55                  60

His Gly Thr Pro Ser Gln Thr Thr Ala Lys Asn Trp Glu Leu Thr Ala

```
                65                  70                  75                  80
Ser Ala Ser His Gln Pro Pro Gly Val Tyr Pro Gln Gly His Ser Asp
                    85                  90                  95

Thr Thr Val Ala Ile Ser
            100

<210> SEQ ID NO 33
<211> LENGTH: 61
<212> TYPE: DNA
<213> ORGANISM: Homo sapiens

<400> SEQUENCE: 33
tccacagtaa cgacggcagg ggtgacccca cagccagaga gcctctcccc ttctggaaaa    60
g                                                                   61

<210> SEQ ID NO 34
<211> LENGTH: 20
<212> TYPE: PRT
<213> ORGANISM: Homo sapiens

<400> SEQUENCE: 34

Ser Thr Val Thr Thr Ala Gly Val Thr Pro Gln Pro Glu Ser Leu Ser
1               5                   10                  15

Pro Ser Gly Lys
            20

<210> SEQ ID NO 35
<211> LENGTH: 292
<212> TYPE: DNA
<213> ORGANISM: Homo sapiens

<400> SEQUENCE: 35
atcacgtgcc ctcccccat gtccgtggaa cacgcagaca tctgggtcaa gagctacagc    60
ttgtactcca gggagcggta catttgtaac tctggtttca gcgtaaagc cggcacgtcc   120 agcctgacgg agtgcgtgtt gaacaaggcc acgaatgtcg cccactggac aacccccagt   180
ctcaaatgca ttgagacccc tgccctggtt caccaaaggc cagcgccacc ctccacagta   240
acgacggcag gggtgacccc acagccagag agcctctccc cttctggaaa ag          292

<210> SEQ ID NO 36
<211> LENGTH: 97
<212> TYPE: PRT
<213> ORGANISM: Homo sapiens

<400> SEQUENCE: 36

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys
```

<210> SEQ ID NO 37
<211> LENGTH: 615
<212> TYPE: DNA
<213> ORGANISM: Homo sapiens

<400> SEQUENCE: 37

```
atggccccgc ggcgggcgcg cggctgccgg accctcggtc tcccggcgct gctactgctg        60
ctgctgctcc ggccgccggc gacgcggggc atcacgtgcc ctccccccat gtccgtggaa       120
cacgcagaca tctgggtcaa gagctacagc ttgtactcca gggagcggta catttgtaac       180
tctggtttca gcgtaaagc cggcacgtcc agcctgacgg agtgcgtgtt gaacaaggcc        240
acgaatgtcg cccactggac aaccccagt ctcaaatgca ttagagaccc tgccctggtt        300
caccaaaggc cagcgccacc ctccacagta cgacggcag gggtgacccc acagccagag        360
agcctctccc cttctggaaa agagcccgca gcttcatctc ccagctcaaa caacacagcg       420
gccacaacag cagctattgt cccgggctcc cagctgatgc cttcaaaatc accttccaca       480
ggaaccacag agataagcag tcatgagtcc tcccacggca cccctctca gacaacagcc        540
aagaactggg aactcacagc atccgcctcc accagccgc caggtgtgta tccacagggc        600
cacagcgaca ccact                                                         615
```

<210> SEQ ID NO 38
<211> LENGTH: 205
<212> TYPE: PRT
<213> ORGANISM: Homo sapiens

<400> SEQUENCE: 38

```
Met Ala Pro Arg Arg Ala Arg Gly Cys Arg Thr Leu Gly Leu Pro Ala
1               5                  10                  15

Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr
        195                 200                 205
```

<210> SEQ ID NO 39
<211> LENGTH: 627
<212> TYPE: DNA
<213> ORGANISM: Homo sapiens

<400> SEQUENCE: 39

```
atggccccgc ggcgggcgcg cggctgccgg accctcggtc tcccggcgct gctactgctg      60
ctgctgctcc ggccgccggc gacgcggggc atcacgtgcc ctcccccat gtccgtggaa      120
cacgcagaca tctgggtcaa gagctacagc ttgtactcca gggagcggta catttgtaac     180
tctggtttca gcgtaaagc cggcacgtcc agcctgacgg agtgcgtgtt gaacaaggcc      240
acgaatgtcg cccactggac aaccccagt ctcaaatgca ttagagaccc tgccctggtt     300
caccaaaggc cagcgccacc ctccacagta acgacggcag gggtgacccc acagccagag    360
agcctctccc cttctggaaa agagcccgca gcttcatctc ccagctcaaa caacacagcg    420
gccacaacag cagctattgt cccgggctcc cagctgatgc cttcaaaatc accttccaca    480
ggaaccacag agataagcag tcatgagtcc tcccacggca cccctctca gacaacagcc     540
aagaactggg aactcacagc atccgcctcc caccagccgc aggtgtgta tccacagggc      600
cacagcgaca ccactgtggc tatctcc                                         627
```

<210> SEQ ID NO 40
<211> LENGTH: 209
<212> TYPE: PRT
<213> ORGANISM: Homo sapiens

<400> SEQUENCE: 40

```
Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser
```

<210> SEQ ID NO 41
<211> LENGTH: 525
<212> TYPE: DNA
<213> ORGANISM: Homo sapiens

<400> SEQUENCE: 41

```
atcacgtgcc ctccccccat gtccgtggaa cacgcagaca tctgggtcaa gagctacagc      60
ttgtactcca gggagcggta catttgtaac tctggtttca gcgtaaagc cggcacgtcc      120
agcctgacgg agtgcgtgtt gaacaaggcc acgaatgtcg cccactggac aaccccagt     180
ctcaaatgca ttagagaccc tgccctggtt caccaaaggc cagcgccacc ctccacagta    240
acgacggcag gggtgacccc acagccagag agcctctccc cttctggaaa agagcccgca    300
gcttcatctc ccagctcaaa caacacagcg ccacaacag cagctattgt cccgggctcc      360
cagctgatgc cttcaaaatc accttccaca ggaaccacag agataagcag tcatgagtcc    420
tcccacggca cccctctca gacaacagcc aagaactggg aactcacagc atccgcctcc     480
caccagccgc caggtgtgta tccacagggc cacagcgaca ccact                     525
```

<210> SEQ ID NO 42
<211> LENGTH: 175
<212> TYPE: PRT
<213> ORGANISM: Homo sapiens

<400> SEQUENCE: 42

```
Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr
                165                 170                 175
```

<210> SEQ ID NO 43
<211> LENGTH: 537
<212> TYPE: DNA
<213> ORGANISM: Homo sapiens

<400> SEQUENCE: 43

```
atcacgtgcc ctccccccat gtccgtggaa cacgcagaca tctgggtcaa gagctacagc      60
ttgtactcca gggagcggta catttgtaac tctggtttca gcgtaaagc cggcacgtcc      120
agcctgacgg agtgcgtgtt gaacaaggcc acgaatgtcg cccactggac aaccccagt     180
```

```
ctcaaatgca ttagagaccc tgccctggtt caccaaaggc cagcgccacc ctccacagta    240
acgacggcag gggtgacccc acagccagag agcctctccc cttctggaaa agagcccgca    300
gcttcatctc ccagctcaaa caacacagcg ccacaacag cagctattgt cccgggctcc     360
cagctgatgc cttcaaaatc accttccaca ggaaccacag agataagcag tcatgagtcc    420
tcccacggca ccccctctca gacaacagcc aagaactggg aactcacagc atccgcctcc    480
caccagccgc caggtgtgta tccacagggc cacagcgaca ccactgtggc tatctcc      537
```

<210> SEQ ID NO 44
<211> LENGTH: 179
<212> TYPE: PRT
<213> ORGANISM: Homo sapiens

<400> SEQUENCE: 44

```
Ile Thr Cys Pro Pro Pro Met Ser Val Glu His Ala Asp Ile Trp Val
  1               5                  10                  15
Lys Ser Tyr Ser Leu Tyr Ser Arg Glu Arg Tyr Ile Cys Asn Ser Gly
             20                  25                  30
Phe Lys Arg Lys Ala Gly Thr Ser Ser Leu Thr Glu Cys Val Leu Asn
         35                  40                  45
Lys Ala Thr Asn Val Ala His Trp Thr Thr Pro Ser Leu Lys Cys Ile
     50                  55                  60
Arg Asp Pro Ala Leu Val His Gln Arg Pro Ala Pro Ser Thr Val
 65                  70                  75                  80
Thr Thr Ala Gly Val Thr Pro Gln Pro Glu Ser Leu Ser Pro Ser Gly
                 85                  90                  95
Lys Glu Pro Ala Ala Ser Ser Pro Ser Ser Asn Asn Thr Ala Ala Thr
            100                 105                 110
Thr Ala Ala Ile Val Pro Gly Ser Gln Leu Met Pro Ser Lys Ser Pro
        115                 120                 125
Ser Thr Gly Thr Thr Glu Ile Ser Ser His Glu Ser Ser His Gly Thr
    130                 135                 140
Pro Ser Gln Thr Thr Ala Lys Asn Trp Glu Leu Thr Ala Ser Ala Ser
145                 150                 155                 160
His Gln Pro Pro Gly Val Tyr Pro Gln Gly His Ser Asp Thr Thr Val
                165                 170                 175
Ala Ile Ser
```

<210> SEQ ID NO 45
<211> LENGTH: 1496
<212> TYPE: DNA
<213> ORGANISM: Homo sapiens

<400> SEQUENCE: 45

```
gactccgggt ggcaggcgcc cgggggaatc ccagctgact cgctcactgc cttcgaagtc    60
cggcgccccc cgggagggaa ctgggtggcc gcaccctccc ggctgcggtg gctgtcgccc   120
cccaccctgc agccaggact cgatggagaa tccattccaa tatatggcca tgtggctctt   180
tggagcaatg ttccatcatg ttccatgctg ctgctgacgt cacatggagc acagaaatca   240
atgttagcag atagccagcc catacaagat cgtattgtat tgtaggaggc atcgtggatg   300
gatggctgct ggaaacccct tgccatagcc agctcttctt caatacttaa ggatttaccg   360
tggctttgag taatgagaat ttcgaaacca catttgagaa gtatttccat ccagtgctac   420
ttgtgtttac ttctaaacag tcatttccta actgaagctg gcattcatgt cttcatttg    480
```

```
ggctgtttca gtgcagggct tcctaaaaca gaagccaact gggtgaatgt aataagtgat      540
ttgaaaaaaa ttgaagatct tattcaatct atgcatattg atgctacttt atatacggaa      600
agtgatgttc accccagttg caaagtaaca gcaatgaagt gctttctctt ggagttacaa      660
gttatttcac ttgagtccgg agatgcaagt attcatgata cagtagaaaa tctgatcatc      720
ctagcaaaca acagtttgtc ttctaatggg aatgtaacag aatctggatg caagaatgt       780 gaggaactgg aggaaaaaaa tattaaagaa ttttttgcaga gttttgtaca tattgtccaa     840
atgttcatca acacttcttg attgcaattg attcttttta aagtgtttct gttattaaca      900
aacatcactc tgctgcttag acataacaaa acactcggca tttcaaatgt gctgtcaaaa      960 caagttttc tgtcaagaag atgatcagac cttggatcag atgaactctt agaaatgaag      1020
gcagaaaaat gtcattgagt aatatagtga ctatgaactt ctctcagact tactttactc     1080
atttttttaa tttattattg aaattgtaca tatttgtgga ataatgtaaa atgttgaata      1140
aaaatatgta caagtgttgt tttttaagtt gcactgatat tttacctctt attgcaaaat     1200
agcatttgtt taagggtgat agtcaaatta tgtattggtg gggctgggta ccaatgctgc     1260
aggtcaacag ctatgctggt aggctcctgc cagtgtggaa ccactgacta ctggctctca     1320
ttgacttcct tactaagcat agcaaacaga ggaagaattt gttatcagta agaaaaagaa     1380
gaactatatg tgaatcctct tctttatact gtaatttagt tattgatgta taaagcaact     1440
gttatgaaat aaagaaattg caataactgg caaaaaaaaa aaaaaaaaaa aaaaaa         1496
```

<210> SEQ ID NO 46
<211> LENGTH: 162
<212> TYPE: PRT
<213> ORGANISM: Homo sapiens

<400> SEQUENCE: 46

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser
```

<210> SEQ ID NO 47
<211> LENGTH: 342
<212> TYPE: DNA

-continued

<213> ORGANISM: Homo sapiens

<400> SEQUENCE: 47

```
aactgggtga atgtaataag tgatttgaaa aaaattgaag atcttattca atctatgcat      60
attgatgcta ctttatatac ggaaagtgat gttcacccca gttgcaaagt aacagcaatg    120
aagtgctttc tcttggagtt acaagttatt tcacttgagt ccggagatgc aagtattcat    180
gatacagtag aaaatctgat catcctagca aacaacagtt tgtcttctaa tgggaatgta    240
acagaatctg gatgcaaaga atgtgaggaa ctggaggaaa aaatattaa agaattttg      300
cagagttttg tacatattgt ccaaatgttc atcaacactt ct                       342
```

<210> SEQ ID NO 48
<211> LENGTH: 114
<212> TYPE: PRT
<213> ORGANISM: Homo sapiens

<400> SEQUENCE: 48

```
Asn Trp Val Asn Val Ile Ser Asp Leu Lys Lys Ile Glu Asp Leu Ile
1               5                   10                  15
Gln Ser Met His Ile Asp Ala Thr Leu Tyr Thr Glu Ser Asp Val His
            20                  25                  30
Pro Ser Cys Lys Val Thr Ala Met Lys Cys Phe Leu Leu Glu Leu Gln
        35                  40                  45
Val Ile Ser Leu Glu Ser Gly Asp Ala Ser Ile His Asp Thr Val Glu
    50                  55                  60
Asn Leu Ile Ile Leu Ala Asn Asn Ser Leu Ser Ser Asn Gly Asn Val
65                  70                  75                  80
Thr Glu Ser Gly Cys Lys Glu Cys Glu Glu Leu Glu Glu Lys Asn Ile
                85                  90                  95
Lys Glu Phe Leu Gln Ser Phe Val His Ile Val Gln Met Phe Ile Asn
            100                 105                 110
Thr Ser
```

<210> SEQ ID NO 49
<211> LENGTH: 60
<212> TYPE: DNA
<213> ORGANISM: Artificial
<220> FEATURE:
<223> OTHER INFORMATION: linker 20

<400> SEQUENCE: 49

```
agcggcggct caggggggtgg aggatctggt ggtggaagtg gaggtggcgg gtctctgcag    60
```

<210> SEQ ID NO 50
<211> LENGTH: 20
<212> TYPE: PRT
<213> ORGANISM: Artificial
<220> FEATURE:
<223> OTHER INFORMATION: linker 20

<400> SEQUENCE: 50

```
Ser Gly Gly Ser Gly Gly Gly Ser Gly Gly Gly Ser Gly Gly Gly
1               5                   10                  15
Gly Ser Leu Gln
            20
```

<210> SEQ ID NO 51
<211> LENGTH: 78
<212> TYPE: DNA

```
<213> ORGANISM: Artificial
<220> FEATURE:
<223> OTHER INFORMATION: linker 26

<400> SEQUENCE: 51
tctggtggcg gatcagggg tggcggatct ggcggggtg gaagtggagg tggcgggtct    60
ggcggaggtt cactgcag                                                 78

<210> SEQ ID NO 52
<211> LENGTH: 26
<212> TYPE: PRT
<213> ORGANISM: Artificial
<220> FEATURE:
<223> OTHER INFORMATION: linker 26

<400> SEQUENCE: 52

Ser Gly Gly Gly Ser Gly Gly Gly Ser Gly Gly Gly Gly Ser Gly
1               5                   10                  15

Gly Gly Gly Ser Gly Gly Gly Ser Leu Gln
            20                  25

<210> SEQ ID NO 53
<211> LENGTH: 36
<212> TYPE: DNA
<213> ORGANISM: Artificial
<220> FEATURE:
<223> OTHER INFORMATION: Nucleic acid sequence of Flag tag and Xa
      binding site

<400> SEQUENCE: 53
gactacaagg atgacgatga caagatagaa ggtagg                             36

<210> SEQ ID NO 54
<211> LENGTH: 12
<212> TYPE: PRT
<213> ORGANISM: Artificial
<220> FEATURE:
<223> OTHER INFORMATION: Flag tag and Xa binding site

<400> SEQUENCE: 54

Asp Tyr Lys Asp Asp Asp Asp Lys Ile Glu Gly Arg
1               5                   10

<210> SEQ ID NO 55
<211> LENGTH: 45
<212> TYPE: DNA
<213> ORGANISM: Artificial
<220> FEATURE:
<223> OTHER INFORMATION: Nucleic acid sequence of Flag tag and Xa
      binding site

<400> SEQUENCE: 55
accacgcgtg actacaagga tgacgatgac aagatagaag gtagg                   45

<210> SEQ ID NO 56
<211> LENGTH: 15
<212> TYPE: PRT
<213> ORGANISM: Artificial
<220> FEATURE:
<223> OTHER INFORMATION: Flag tag and Xa binding site

<400> SEQUENCE: 56

Thr Thr Arg Asp Tyr Lys Asp Asp Asp Asp Lys Ile Glu Gly Arg
1               5                   10                  15
```

-continued

<210> SEQ ID NO 57
<211> LENGTH: 93
<212> TYPE: DNA
<213> ORGANISM: Bos sp.

<400> SEQUENCE: 57

```
atggacagca aaggttcgtc gcagaaagca gggtcccgcc tgctcctgct gctggtggtg      60
tcaaatctac tcttgtgcca gggtgtggtc tcc                                  93
```

<210> SEQ ID NO 58
<211> LENGTH: 31
<212> TYPE: PRT
<213> ORGANISM: Bos sp.

<400> SEQUENCE: 58

```
Met Asp Ser Lys Gly Ser Ser Gln Lys Ala Gly Ser Arg Leu Leu Leu
1               5                   10                  15
Leu Leu Val Val Ser Asn Leu Leu Leu Cys Gln Gly Val Val Ser
            20                  25                  30
```

<210> SEQ ID NO 59
<211> LENGTH: 768
<212> TYPE: DNA
<213> ORGANISM: Artificial
<220> FEATURE:
<223> OTHER INFORMATION: Nucleic acid sequence of RLI fusion protein

<400> SEQUENCE: 59

```
gccgccatgg cccgcggcg ggcgcgcggc tgccggaccc tcggtctccc ggcgctgcta      60
ctgctgctgc tgctccggcc gccggcgacg cggggcgact acaaggatga cgatgacaag    120
atagaaggta ggatcacatg ccctccccc atgtccgtgg aacacgcaga catctgggtc     180
aagagctaca gcttgtactc cagggagcgg tacatttgta actctggttt caagcgtaaa    240
gccggcacgt ccagcctgac agagtgcgtg ttgaacaagg ccacgaatgt cgcccactgg    300
acaaccccca gtctcaaatg cattagagac cctgccctgg ttcaccaaag gccagcgcca    360
cccagcggcg gctcaggggg tggaggatct ggtggtggaa gtggaggtgg cgggtctctg    420
cagaactggg tgaatgtaat aagtgatttg aaaaaaattg aagatcttat tcaatctatg    480
catattgatg ctactttata tacggaaagt gatgttcacc ccagttgcaa agtaacagca    540
atgaagtgct ttctcttgga gttacaagtt atttcacttg agtccggaga tgcaagtatt    600
catgatacag tagaaaatct gatcatccta gcaaacaaca gtttgtcttc taatgggaat    660
gtaacagaat ctggatgcaa agaatgtgag gaactggagg aaaaaaatat taagaatttt    720
ttgcagagtt ttgtacatat tgtccaaatg ttcatcaaca cttcttag                 768
```

<210> SEQ ID NO 60
<211> LENGTH: 253
<212> TYPE: PRT
<213> ORGANISM: Artificial
<220> FEATURE:
<223> OTHER INFORMATION: RLI fusion protein

<400> SEQUENCE: 60

```
Met Ala Pro Arg Arg Ala Arg Gly Cys Arg Thr Leu Gly Leu Pro Ala
1               5                   10                  15
Leu Leu Leu Leu Leu Leu Arg Pro Pro Ala Thr Arg Gly Asp Tyr
            20                  25                  30
Lys Asp Asp Asp Asp Lys Ile Glu Gly Arg Ile Thr Cys Pro Pro Pro
        35                  40                  45
```

Met Ser Val Glu His Ala Asp Ile Trp Val Lys Ser Tyr Ser Leu Tyr
 50                  55                  60

Ser Arg Glu Arg Tyr Ile Cys Asn Ser Gly Phe Lys Arg Lys Ala Gly
 65                  70                  75                  80

Thr Ser Ser Leu Thr Glu Cys Val Leu Asn Lys Ala Thr Asn Val Ala
                 85                  90                  95

His Trp Thr Thr Pro Ser Leu Lys Cys Ile Arg Asp Pro Ala Leu Val
                100                 105                 110

His Gln Arg Pro Ala Pro Pro Ser Gly Gly Ser Gly Gly Gly Gly Ser
            115                 120                 125

Gly Gly Gly Ser Gly Gly Gly Ser Leu Gln Asn Trp Val Asn Val
        130                 135                 140

Ile Ser Asp Leu Lys Lys Ile Glu Asp Leu Ile Gln Ser Met His Ile
145                 150                 155                 160

Asp Ala Thr Leu Tyr Thr Glu Ser Asp Val His Pro Ser Cys Lys Val
                165                 170                 175

Thr Ala Met Lys Cys Phe Leu Leu Glu Leu Gln Val Ile Ser Leu Glu
                180                 185                 190

Ser Gly Asp Ala Ser Ile His Asp Thr Val Glu Asn Leu Ile Ile Leu
            195                 200                 205

Ala Asn Asn Ser Leu Ser Ser Asn Gly Asn Val Thr Glu Ser Gly Cys
210                 215                 220

Lys Glu Cys Glu Glu Leu Glu Glu Lys Asn Ile Lys Glu Phe Leu Gln
225                 230                 235                 240

Ser Phe Val His Ile Val Gln Met Phe Ile Asn Thr Ser
                245                 250

<210> SEQ ID NO 61
<211> LENGTH: 798
<212> TYPE: DNA
<213> ORGANISM: Artificial
<220> FEATURE:
<223> OTHER INFORMATION: Nucleic acid sequence of ILR fusion protein

<400> SEQUENCE: 61
gccaccatgg acagcaaagg ttcgtcgcag aaagcagggt cccgcctgct cctgctgctg      60
gtggtgtcaa atctactctt gtgccagggt gtggtctcca ccacgcgaga ctacaaggat     120
gacgatgaca agatagaagg cgtaactggg gtgaatgtaa taagtgattt gaaaaaaatt     180
gaagatctta ttcaatctat gcatattgat gctactttat atacggaaag tgatgttcac     240
cccagttgca agtaacagc aatgaagtgc tttctcttgg agttacaagt tatttcactt     300
gagtccggag atgcaagtat tcatgataca gtagaaaatc tgatcatcct agcaaacaac     360
agtttgtctt ctaatgggaa tgtaacagaa tctggatgca agaatgtga ggaactggag     420 gaaaaaata ttaagaatt tttgcagagt tttgtacata ttgtccaaat gttcatcaac     480
actagttctg gtggcggatc aggggggtggc ggatctggcg ggggtggaag tggaggtggc     540
gggtctggcg gaggttcact gcagatcaca tgccctcccc ccatgtccgt ggaacacgca     600
gacatctggg tcaagagcta cagcttgtac tccagggagc ggtacatttg taactctggt     660
ttcaagcgta aagccggcac gtccagcctg acagagtgcg tgttgaacaa ggccacgaat     720
gtcgcccact ggacaacccc cagtctcaaa tgcattagag accctgccct ggttcaccaa     780
aggccagcgc caccctga                                                   798

-continued

<210> SEQ ID NO 62
<211> LENGTH: 263
<212> TYPE: PRT
<213> ORGANISM: Artificial
<220> FEATURE:
<223> OTHER INFORMATION: ILR fusion protein

<400> SEQUENCE: 62

```
Met Asp Ser Lys Gly Ser Ser Gln Lys Ala Gly Ser Arg Leu Leu Leu
1               5                   10                  15
Leu Leu Val Val Ser Asn Leu Leu Leu Cys Gln Gly Val Val Ser Thr
            20                  25                  30
Thr Arg Asp Tyr Lys Asp Asp Asp Lys Ile Glu Gly Arg Asn Trp Val
        35                  40                  45
Asn Val Ile Ser Asp Leu Lys Lys Ile Glu Asp Leu Ile Gln Ser Met
    50                  55                  60
His Ile Asp Ala Thr Leu Tyr Thr Glu Ser Asp Val His Pro Ser Cys
65                  70                  75                  80
Lys Val Thr Ala Met Lys Cys Phe Leu Leu Glu Leu Gln Val Ile Ser
                85                  90                  95
Leu Glu Ser Gly Asp Ala Ser Ile His Asp Thr Val Glu Asn Leu Ile
            100                 105                 110
Ile Leu Ala Asn Asn Ser Leu Ser Ser Asn Gly Asn Val Thr Glu Ser
        115                 120                 125
Gly Cys Lys Glu Cys Glu Glu Leu Glu Glu Lys Asn Ile Lys Glu Phe
    130                 135                 140
Leu Gln Ser Phe Val His Ile Val Gln Met Phe Ile Asn Thr Ser Ser
145                 150                 155                 160
Gly Gly Gly Ser Gly Gly Gly Ser Gly Gly Gly Ser Gly Gly Gly Ser
                165                 170                 175
Gly Gly Gly Ser Leu Gln Ile Thr Cys Pro Pro Pro Met Ser Val Glu
            180                 185                 190
His Ala Asp Ile Trp Val Lys Ser Tyr Ser Leu Tyr Ser Arg Glu Arg
        195                 200                 205
Tyr Ile Cys Asn Ser Gly Phe Lys Arg Lys Ala Gly Thr Ser Ser Leu
    210                 215                 220
Thr Glu Cys Val Leu Asn Lys Ala Thr Asn Val Ala His Trp Thr Thr
225                 230                 235                 240
Pro Ser Leu Lys Cys Ile Arg Asp Pro Ala Leu Val His Gln Arg Pro
                245                 250                 255
Ala Pro Pro
        260
```

<210> SEQ ID NO 63
<211> LENGTH: 1047
<212> TYPE: DNA
<213> ORGANISM: Homo sapiens

<400> SEQUENCE: 63

```
cgaattcccc tatcacctaa gtgtgggcta atgtaacaaa gagggatttc acctacatcc    60
attcagtcag tctttggggg tttaaagaaa ttccaaagag tcatcagaag aggaaaaatg   120
aaggtaatgt ttttcagac aggtaaagtc tttgaaaata tgtgtaatat gtaaaacatt    180
ttgacacccc cataatattt ttccagaatt aacagtataa attgcatctc ttgttcaaga   240
gttccctatc actctcttta atcactactc acagtaacct caactcctgc acaatgtac    300
aggatgcaac tcctgtcttg cattgcacta agtcttgcac ttgtcacaaa cagtgcacct   360
```

```
acttcaagtt ctacaaagaa aacacagcta caactggagc atttactgct ggatttacag    420
atgattttga atggaattaa taattacaag aatcccaaac tcaccaggat gctcacattt    480
aagttttaca tgcccaagaa ggccacagaa ctgaaacatc ttcagtgtct agaagaagaa    540
ctcaaacctc tggaggaagt gctaaattta gctcaaagca aaactttca cttaagaccc    600 agggacttaa tcagcaatat caacgtaata gttctggaac taagggatc tgaaacaaca    660 ttcatgtgtg aatatgctga tgagacagca accattgtag aatttctgaa cagatggat   720 acctttgtc aaagcatcat ctcaacactg acttgataat taagtgcttc ccacttaaaa    780
catatcaggc cttctattta tttaaatatt taaattttat attattgtt gaatgtatgg    840 tttgctacct attgtaacta ttattcttaa tcttaaaact ataaatatgg atcttttatg    900 attcttttg taagccctag gggctctaaa atggtttcac ttatttatcc caaaatattt    960
attattatgt tgaatgttaa atatagtatc tatgtagatt ggttagtaaa actatttaat   1020
aaatttgata aatataaaaa aaaaaaa                                       1047
```

<210> SEQ ID NO 64
<211> LENGTH: 399
<212> TYPE: DNA
<213> ORGANISM: Homo sapiens

<400> SEQUENCE: 64

```
gcacctactt caagttctac aaagaaaaca cagctacaac tggagcattt actgctggat     60
ttacagatga ttttgaatgg aattaataat tacaagaatc ccaaactcac caggatgctc    120
acatttaagt tttacatgcc caagaaggcc acagaactga acatcttca gtgtctagaa    180 gaagaactca aacctctgga ggaagtgcta aatttagctc aaagcaaaaa ctttcactta    240
agacccaggg acttaatcag caatatcaac gtaatagttc tggaactaaa gggatctgaa    300
acaacattca tgtgtgaata tgctgatgag acagcaacca ttgtagaatt tctgaacaga    360
tggattacct tttgtcaaag catcatctca acactgact                            399
```

<210> SEQ ID NO 65
<211> LENGTH: 133
<212> TYPE: PRT
<213> ORGANISM: Homo sapiens

<400> SEQUENCE: 65

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125
```

Ile Ser Thr Leu Thr
            130

<210> SEQ ID NO 66
<211> LENGTH: 702
<212> TYPE: DNA
<213> ORGANISM: Artificial
<220> FEATURE:
<223> OTHER INFORMATION: Nucleic acid sequence of a sushi-containing
      hIL-15Ralpha fragment, tagged with IL-2

<400> SEQUENCE: 66

```
gccgccatgg ccccgcggcg ggcgcgcggc tgccggaccc tcggtctccc ggcgctgcta    60
ctgctgctgc tgctccggcc gccggcgacg cggggcatca cgtgccctcc ccccatgtcc   120
gtggaacacg cagacatctg ggtcaagagc tacagcttgt actccaggga gcggtacatt   180
tgtaactctg gtttcaagcg taaagccggc acgtccagcc tgacggagtg cgtgttgaac   240
aaggccacga atgtcgccca ctggacaacc cccagtctca aatgcattag agacctgcag   300
gcacctactt caagttctac aaagaaaaca cagctacaac tggagcattt actgctggat   360
ttacagatga ttttgaatgg aattaataat tacaagaatc ccaaactcac caggatgctc   420
acatttaagt tttacatgcc caagaaggcc acagaactga aacatcttca gtgtctagaa   480
gaagaactca aacctctgga ggaagtgcta aatttagctc aaagcaaaaa ctttcactta   540
agacccaggg acttaatcag caatatcaac gtaatagttc tggaactaaa gggatctgaa   600
acaacattca gtgtgaata tgctgatgag acagcaacca ttgtagaatt tctgaacaga   660
tggattacct tttgtcaaag catcatctca acactgactt ga                      702
```

<210> SEQ ID NO 67
<211> LENGTH: 231
<212> TYPE: PRT
<213> ORGANISM: Artificial
<220> FEATURE:
<223> OTHER INFORMATION: Sushi containing hIL-15 Ralpha fragment, tagged
      with IL2

<400> SEQUENCE: 67

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Leu Gln Ala Pro Thr Ser Ser Ser Thr Lys Lys Thr Gln Leu Gln Leu
            100                 105                 110

Glu His Leu Leu Leu Asp Leu Gln Met Ile Leu Asn Gly Ile Asn Asn
        115                 120                 125

Tyr Lys Asn Pro Lys Leu Thr Arg Met Leu Thr Phe Lys Phe Tyr Met
    130                 135                 140

Pro Lys Lys Ala Thr Glu Leu Lys His Leu Gln Cys Leu Glu Glu Glu
145                 150                 155                 160

Leu Lys Pro Leu Glu Glu Val Leu Asn Leu Ala Gln Ser Lys Asn Phe
            165                 170                 175

His Leu Arg Pro Arg Asp Leu Ile Ser Asn Ile Asn Val Ile Val Leu
        180                 185                 190

Glu Leu Lys Gly Ser Glu Thr Thr Phe Met Cys Glu Tyr Ala Asp Glu
    195                 200                 205

Thr Ala Thr Ile Val Glu Phe Leu Asn Arg Trp Ile Thr Phe Cys Gln
    210                 215                 220

Ser Ile Ile Ser Thr Leu Thr
225             230

<210> SEQ ID NO 68
<211> LENGTH: 1029
<212> TYPE: DNA
<213> ORGANISM: Artificial
<220> FEATURE:
<223> OTHER INFORMATION: Nucleic acid seqeunce of a fragment of
      extracellular hIL-15Ralpha, tagged with IL-2

<400> SEQUENCE: 68

```
gccgccatgg ccccgcggcg ggcgcgcggc tgccggaccc tcggtctccc ggcgctgcta    60
ctgctgctgc tgctccggcc gccggcgacg cggggcatca cgtgccctcc ccccatgtcc   120
gtggaacacg cagacatctg ggtcaagagc tacagcttgt actccaggga gcggtacatt   180
tgtaactctg gtttcaagcg taaagccggc acgtccagcc tgacggagtg cgtgttgaac   240
aaggccacga atgtcgccca ctggacaacc cccagtctca atgcattag agaccctgcc    300
ctggttcacc aaaggccagc gccacccctcc acagtaacga cggcaggggt gaccccacag   360
ccagagagcc tctcccttc tggaaaagag cccgcagctt catctcccag ctcaaacaac    420
acagcggcca acagcagc tattgtcccg ggctcccagc tgatgccttc aaaatcacct    480
tccacaggaa ccacagagat aagcagtcat gagtcctccc acggcacccc ctctcagaca   540
acagccaaga actgggaact cacagcatcc gcctcccacc agccgccagg tgtgtatcca   600
cagggccaca gcgacaccac tctgcaggca cctacttcaa gttctacaaa gaaaacacag   660
ctacaactgg agcatttact gctggattta cagatgattt tgaatggaat taataattac   720
aagaatccca aactcaccag gatgctcaca tttaagtttt acatgcccaa gaaggccaca   780
gaactgaaac atcttcagtg tctagaagaa gaactcaaac ctctggagga agtgctaaat   840
ttagctcaaa gcaaaaactt tcacttaaga cccagggact aatcagcaa tatcaacgta    900
atagttctgg aactaaaggg atctgaaaca acattcatgt gtgaatatgc tgatgagaca   960
gcaaccattg tagaatttct gaacagatgg attacctttt gtcaaagcat catctcaaca  1020
ctgacttga                                                           1029
```

<210> SEQ ID NO 69
<211> LENGTH: 340
<212> TYPE: PRT
<213> ORGANISM: Artificial
<220> FEATURE:
<223> OTHER INFORMATION: Fragment of extracellular hIL-15Ralpha, tagged
      with IL-2

<400> SEQUENCE: 69

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

```
Cys Pro Pro Met Ser Val Glu His Ala Asp Ile Trp Val Lys Ser
         35                  40                  45
Tyr Ser Leu Tyr Ser Arg Glu Arg Tyr Ile Cys Asn Ser Gly Phe Lys
 50                  55                  60
Arg Lys Ala Gly Thr Ser Ser Leu Thr Glu Cys Val Leu Asn Lys Ala
 65                  70                  75                  80
Thr Asn Val Ala His Trp Thr Thr Pro Ser Leu Lys Cys Ile Arg Asp
                 85                  90                  95
Pro Ala Leu Val His Gln Arg Pro Ala Pro Pro Ser Thr Val Thr Thr
                100                 105                 110
Ala Gly Val Thr Pro Gln Pro Glu Ser Leu Ser Pro Ser Gly Lys Glu
            115                 120                 125
Pro Ala Ala Ser Ser Pro Ser Ser Asn Asn Thr Ala Ala Thr Thr Pro
130                 135                 140
Ala Ile Val Pro Gly Ser Gln Leu Met Pro Ser Lys Ser Pro Ser Thr
145                 150                 155                 160
Gly Thr Thr Glu Ile Ser Ser His Glu Ser Ser His Gly Thr Pro Ser
                165                 170                 175
Gln Thr Thr Ala Lys Asn Trp Glu Leu Thr Ala Pro Ala Ser His Gln
            180                 185                 190
Pro Pro Gly Val Tyr Pro Gln Gly His Ser Asp Thr Thr Leu Gln Ala
        195                 200                 205
Pro Thr Ser Ser Ser Thr Lys Lys Thr Gln Leu Gln Leu Glu His Leu
    210                 215                 220
Leu Leu Asp Leu Gln Met Ile Leu Asn Gly Ile Asn Asn Tyr Lys Asn
225                 230                 235                 240
Pro Lys Leu Thr Arg Met Leu Thr Phe Lys Phe Tyr Met Pro Lys Lys
                245                 250                 255
Ala Thr Glu Leu Lys His Leu Gln Cys Leu Glu Glu Glu Leu Lys Pro
            260                 265                 270
Leu Glu Glu Val Leu Asn Leu Ala Gln Ser Lys Asn Phe His Leu Arg
        275                 280                 285
Pro Arg Asp Leu Ile Ser Asn Ile Asn Val Ile Val Leu Glu Leu Lys
    290                 295                 300
Gly Ser Glu Thr Thr Phe Met Cys Glu Tyr Ala Asp Glu Thr Ala Thr
305                 310                 315                 320
Ile Val Glu Phe Leu Asn Arg Trp Ile Thr Phe Cys Gln Ser Ile Ile
                325                 330                 335
Ser Thr Leu Thr
            340

<210> SEQ ID NO 70
<211> LENGTH: 18
<212> TYPE: DNA
<213> ORGANISM: Artificial
<220> FEATURE:
<223> OTHER INFORMATION: Beta chain sense primer

<400> SEQUENCE: 70
gagagactgg atggaccc                                               18

<210> SEQ ID NO 71
<211> LENGTH: 23
<212> TYPE: DNA
<213> ORGANISM: Artificial
<220> FEATURE:
<223> OTHER INFORMATION: Beta chain reverse primer
```

<400> SEQUENCE: 71
aagaaactaa ctcttaaaga ggc                                              23

<210> SEQ ID NO 72
<211> LENGTH: 792
<212> TYPE: DNA
<213> ORGANISM: Mus musculus

<400> SEQUENCE: 72

| atggcctcgc cgcagctccg gggctatgga gtccaggcca ttcctgtgtt gctgctgctg | 60 |
| ctgttgctac tgttgctccc gctgagggtg acgccgggca ccacgtgtcc acctcccgta | 120 |
| tctattgagc atgctgacat ccgggtcaag aattacagtg tgaactccag ggagaggtat | 180 |
| gtctgtaact ctggctttaa gcggaaagct ggaacatcca ccctgattga gtgtgtgatc | 240 |
| aacaagaaca caaatgttgc ccactggaca actcccagcc tcaagtgcat cagagacccc | 300 |
| tccctagctc actacagtcc agtgccaaca gtagtgacac aaaggtgac ctcacagcca | 360 |
| gagagcccct cccctctgc aaaagagcca gaagctttct ctcccaaatc agataccgca | 420 |
| atgaccacag agacagctat tatgcctggc tccaggctga ccatcccaa acaacttct | 480 |
| gcaggaacta cagggacagg cagtcacaag tcctcccgag ccccatctct tgcagcaaca | 540 |
| atgaccttgg agcctacagc ctccacctcc ctcaggataa cagagatttc tccccacagt | 600 |
| tccaaaatga cgaaagtggc catctctaca tcggtcctct tggttggtgc aggggttgtg | 660 |
| atggcttcc tggcctggta catcaaatca aggcagcctt ctcagccgtg ccgtgttgag | 720 |
| gtggaaacca tggaaacagt accaatgact gtgagggcca gcagcaagga ggatgaagac | 780 |
| acaggagcct aa | 792 |

<210> SEQ ID NO 73
<211> LENGTH: 263
<212> TYPE: PRT
<213> ORGANISM: Mus musculus

<400> SEQUENCE: 73

Met Ala Ser Pro Gln Leu Arg Gly Tyr Gly Val Gln Ala Ile Pro Val
1               5                   10                  15

Leu Leu Leu Leu Leu Leu Leu Leu Leu Pro Leu Arg Val Thr Pro
            20                  25                  30

Gly Thr Thr Cys Pro Pro Pro Val Ser Ile Glu His Ala Asp Ile Arg
        35                  40                  45

Val Lys Asn Tyr Ser Val Asn Ser Arg Glu Arg Tyr Val Cys Asn Ser
    50                  55                  60

Gly Phe Lys Arg Lys Ala Gly Thr Ser Thr Leu Ile Glu Cys Val Ile
65                  70                  75                  80

Asn Lys Asn Thr Asn Val Ala His Trp Thr Thr Pro Ser Leu Lys Cys
                85                  90                  95

Ile Arg Asp Pro Ser Leu Ala His Tyr Ser Pro Val Pro Thr Val Val
            100                 105                 110

Thr Pro Lys Val Thr Ser Gln Pro Glu Ser Pro Ser Pro Ser Ala Lys
        115                 120                 125

Glu Pro Glu Ala Phe Ser Pro Lys Ser Asp Thr Ala Met Thr Thr Glu
    130                 135                 140

Thr Ala Ile Met Pro Gly Ser Arg Leu Thr Pro Ser Gln Thr Thr Ser
145                 150                 155                 160

```
Ala Gly Thr Thr Gly Thr Gly Ser His Lys Ser Ser Arg Ala Pro Ser
            165                 170                 175

Leu Ala Ala Thr Met Thr Leu Glu Pro Thr Ala Ser Thr Ser Leu Arg
            180                 185                 190

Ile Thr Glu Ile Ser Pro His Ser Ser Lys Met Thr Lys Val Ala Ile
            195                 200                 205

Ser Thr Ser Val Leu Leu Val Gly Ala Gly Val Val Met Ala Phe Leu
            210                 215                 220

Ala Trp Tyr Ile Lys Ser Arg Gln Pro Ser Gln Pro Cys Arg Val Glu
225                 230                 235                 240

Val Glu Thr Met Glu Thr Val Pro Met Thr Val Arg Ala Ser Ser Lys
            245                 250                 255

Glu Asp Glu Asp Thr Gly Ala
            260

<210> SEQ ID NO 74
<211> LENGTH: 205
<212> TYPE: PRT
<213> ORGANISM: Mus musculus

<400> SEQUENCE: 74

Met Ala Ser Pro Gln Leu Arg Gly Tyr Gly Val Gln Ala Ile Pro Val
1               5                   10                  15

Leu Leu Leu Leu Leu Leu Leu Leu Leu Pro Leu Arg Val Thr Pro
            20                  25                  30

Gly Thr Thr Cys Pro Pro Val Ser Ile Glu His Ala Asp Ile Arg
            35                  40                  45

Val Lys Asn Tyr Ser Val Asn Ser Arg Glu Arg Tyr Val Cys Asn Ser
50                  55                  60

Gly Phe Lys Arg Lys Ala Gly Thr Ser Thr Leu Ile Glu Cys Val Ile
65                  70                  75                  80

Asn Lys Asn Thr Asn Val Ala His Trp Thr Thr Pro Ser Leu Lys Cys
            85                  90                  95

Ile Arg Asp Pro Ser Leu Ala His Tyr Ser Pro Val Pro Thr Val Val
            100                 105                 110

Thr Pro Lys Val Thr Ser Gln Pro Glu Ser Pro Ser Pro Ser Ala Lys
            115                 120                 125

Glu Pro Glu Ala Phe Ser Pro Lys Ser Asp Thr Ala Met Thr Thr Glu
            130                 135                 140

Thr Ala Ile Met Pro Gly Ser Arg Leu Thr Pro Ser Gln Thr Thr Ser
145                 150                 155                 160

Ala Gly Thr Thr Gly Thr Gly Ser His Lys Ser Ser Arg Ala Pro Ser
            165                 170                 175

Leu Ala Ala Thr Met Thr Leu Glu Pro Thr Ala Ser Thr Ser Leu Arg
            180                 185                 190

Ile Thr Glu Ile Ser Pro His Ser Ser Lys Met Thr Lys
            195                 200                 205

<210> SEQ ID NO 75
<211> LENGTH: 61
<212> TYPE: PRT
<213> ORGANISM: Mus musculus

<400> SEQUENCE: 75

Cys Pro Pro Val Ser Ile Glu His Ala Asp Ile Arg Val Lys Asn
1               5                   10                  15
```

```
Tyr Ser Val Asn Ser Arg Glu Arg Tyr Val Cys Asn Ser Gly Phe Lys
            20                  25                  30

Arg Lys Ala Gly Thr Ser Thr Leu Ile Glu Cys Val Ile Asn Lys Asn
        35                  40                  45

Thr Asn Val Ala His Trp Thr Thr Pro Ser Leu Lys Cys
    50                  55                  60

<210> SEQ ID NO 76
<211> LENGTH: 13
<212> TYPE: PRT
<213> ORGANISM: Mus musculus

<400> SEQUENCE: 76

Ile Arg Asp Pro Ser Leu Ala His Tyr Ser Pro Val Pro
1               5                   10

<210> SEQ ID NO 77
<211> LENGTH: 96
<212> TYPE: PRT
<213> ORGANISM: Mus musculus

<400> SEQUENCE: 77

Thr Val Val Thr Pro Lys Val Thr Ser Gln Pro Glu Ser Pro Ser Pro
1               5                   10                  15

Ser Ala Lys Glu Pro Glu Ala Phe Ser Pro Lys Ser Asp Thr Ala Met
            20                  25                  30

Thr Thr Glu Thr Ala Ile Met Pro Gly Ser Arg Leu Thr Pro Ser Gln
        35                  40                  45

Thr Thr Ser Ala Gly Thr Gly Thr Gly Ser His Lys Ser Ser Arg
    50                  55                  60

Ala Pro Ser Leu Ala Ala Thr Met Thr Leu Glu Pro Thr Ala Ser Thr
65                  70                  75                  80

Ser Leu Arg Ile Thr Glu Ile Ser Pro His Ser Ser Lys Met Thr Lys
                85                  90                  95

<210> SEQ ID NO 78
<211> LENGTH: 1035
<212> TYPE: DNA
<213> ORGANISM: Pan troglodytes

<400> SEQUENCE: 78
atggagaaat tcacctggca cacaagaggc atcacgtgcc ctcccccat gtccgtggaa       60 cacgcagaca tctgggtcaa gagctacagc ttgtactcca gggagcggta catttgtaac    120
tctggtttca gcgtaaagc cggcacgtcc agcctgacgg agtgcgtgtt gaacaaggcc    180
acgaatgtcg cccactggac aacccccagt ctcaaatgca ttagagaccc tgccctggtt    240
ctccaaaggc cagtgccacc ctccacagta acgacggcag ggatgacccc acagccagag    300
agcctctccc cttctggaaa aggttccgtg gctgtcacaa tggaagacac attttttcatg    360 gagagggaac agcacagtta cgccacaccc ttacagtgca gggcagcca ccttccaggg    420 aaggacaagg aagacaggga agacgctgaa cacaaggcag cctctgttcc tgagcgcaag    480
ctcatcagga cgctttcctc ccacacgcg cggagagttc aggccagagc ccaggcttcc    540 cgtgttttcac acgcagccgc tccgagcgtc ctcggccagc gcagcttcac ctgctctcag    600
ctgagcctcc agcagcccgc agcttcatct cccagctcaa acaccacagc ggccacaaca    660
gcagctattg tccgggctc ccagctgatg ccttcaaaat caccttccac aggaaccaca    720
gagataggca gtcatgagtc ctcccacggc accccctctc agacaacagc caagacctgg    780
```

```
gaactcacag catctgcctc ccaccagccg ccaggtgtgt atccacaggg ccacagcgac    840
accactgtgg ctatctccac gtccactgtc ctgctgtgtg ggctgagcgc tgtgtctctc    900
ctggcatgct acctcaagtc aaggcaaact ccccgctgg ccagcgttga aatggaagcc    960
atggaggctc tgccggtgac tgggggggacc agcagcagag atgaagactt ggaaaactgc   1020
tctcaccacc tatga                                                    1035
```

<210> SEQ ID NO 79
<211> LENGTH: 344
<212> TYPE: PRT
<213> ORGANISM: Pan troglodytes

<400> SEQUENCE: 79

```
Met Glu Lys Phe Thr Trp His Thr Arg Gly Ile Thr Cys Pro Pro Pro
1               5                   10                  15

Met Ser Val Glu His Ala Asp Ile Trp Val Lys Ser Tyr Ser Leu Tyr
            20                  25                  30

Ser Arg Glu Arg Tyr Ile Cys Asn Ser Gly Phe Lys Arg Lys Ala Gly
        35                  40                  45

Thr Ser Ser Leu Thr Glu Cys Val Leu Asn Lys Ala Thr Asn Val Ala
    50                  55                  60

His Trp Thr Thr Pro Ser Leu Lys Cys Ile Arg Asp Pro Ala Leu Val
65                  70                  75                  80

Leu Gln Arg Pro Val Pro Ser Thr Val Thr Thr Ala Gly Met Thr
                85                  90                  95

Pro Gln Pro Glu Ser Leu Ser Pro Ser Gly Lys Gly Ser Val Ala Val
            100                 105                 110

Thr Met Glu Asp Thr Phe Phe Met Glu Arg Glu Gln His Ser Tyr Ala
        115                 120                 125

Thr Pro Leu Gln Cys Arg Gly Ser His Leu Pro Gly Lys Asp Lys Glu
    130                 135                 140

Asp Arg Glu Asp Ala Glu His Lys Ala Ala Ser Val Pro Glu Arg Lys
145                 150                 155                 160

Leu Ile Arg Thr Leu Ser Ser His Thr Ala Arg Arg Val Gln Ala Arg
                165                 170                 175

Ala Gln Ala Ser Arg Val Ser His Ala Ala Pro Ser Val Leu Gly
            180                 185                 190

Gln Arg Ser Phe Thr Cys Ser Gln Leu Ser Leu Gln Gln Pro Ala Ala
        195                 200                 205

Ser Ser Pro Ser Ser Asn Thr Thr Ala Ala Thr Ala Ala Ile Val
    210                 215                 220

Pro Gly Ser Gln Leu Met Pro Ser Lys Ser Pro Ser Thr Gly Thr Thr
225                 230                 235                 240

Glu Ile Gly Ser His Glu Ser Ser His Gly Thr Pro Ser Gln Thr Thr
                245                 250                 255

Ala Lys Thr Trp Glu Leu Thr Ala Ser Ala Ser His Gln Pro Pro Gly
            260                 265                 270

Val Tyr Pro Gln Gly His Ser Asp Thr Thr Val Ala Ile Ser Thr Ser
        275                 280                 285

Thr Val Leu Leu Cys Gly Leu Ser Ala Val Ser Leu Leu Ala Cys Tyr
    290                 295                 300

Leu Lys Ser Arg Gln Thr Pro Pro Leu Ala Ser Val Glu Met Glu Ala
305                 310                 315                 320
```

Met Glu Ala Leu Pro Val Thr Gly Gly Thr Ser Ser Arg Asp Glu Asp
                325                 330                 335

Leu Glu Asn Cys Ser His His Leu
            340

<210> SEQ ID NO 80
<211> LENGTH: 286
<212> TYPE: PRT
<213> ORGANISM: Pan troglodytes

<400> SEQUENCE: 80

Met Glu Lys Phe Thr Trp His Thr Arg Gly Ile Thr Cys Pro Pro Pro
1               5                   10                  15

Met Ser Val Glu His Ala Asp Ile Trp Val Lys Ser Tyr Ser Leu Tyr
            20                  25                  30

Ser Arg Glu Arg Tyr Ile Cys Asn Ser Gly Phe Lys Arg Lys Ala Gly
        35                  40                  45

Thr Ser Ser Leu Thr Glu Cys Val Leu Asn Lys Ala Thr Asn Val Ala
    50                  55                  60

His Trp Thr Thr Pro Ser Leu Lys Cys Ile Arg Asp Pro Ala Leu Val
65                  70                  75                  80

Leu Gln Arg Pro Val Pro Pro Ser Thr Val Thr Thr Ala Gly Met Thr
                85                  90                  95

Pro Gln Pro Glu Ser Leu Ser Pro Ser Gly Lys Gly Ser Val Ala Val
            100                 105                 110

Thr Met Glu Asp Thr Phe Phe Met Glu Arg Glu Gln His Ser Tyr Ala
        115                 120                 125

Thr Pro Leu Gln Cys Arg Gly Ser His Leu Pro Gly Lys Asp Lys Glu
    130                 135                 140

Asp Arg Glu Asp Ala Glu His Lys Ala Ala Ser Val Pro Glu Arg Lys
145                 150                 155                 160

Leu Ile Arg Thr Leu Ser Ser His Thr Ala Arg Arg Val Gln Ala Arg
                165                 170                 175

Ala Gln Ala Ser Arg Val Ser His Ala Ala Pro Ser Val Leu Gly
            180                 185                 190

Gln Arg Ser Phe Thr Cys Ser Gln Leu Ser Leu Gln Gln Pro Ala Ala
        195                 200                 205

Ser Ser Pro Ser Ser Asn Thr Thr Ala Ala Thr Thr Ala Ala Ile Val
    210                 215                 220

Pro Gly Ser Gln Leu Met Pro Ser Lys Ser Pro Ser Thr Gly Thr Thr
225                 230                 235                 240

Glu Ile Gly Ser His Glu Ser Ser His Gly Thr Pro Ser Gln Thr Thr
                245                 250                 255

Ala Lys Thr Trp Glu Leu Thr Ala Ala Ser His Gln Pro Pro Gly
            260                 265                 270

Val Tyr Pro Gln Gly His Ser Asp Thr Thr Val Ala Ile Ser
        275                 280                 285

<210> SEQ ID NO 81
<211> LENGTH: 61
<212> TYPE: PRT
<213> ORGANISM: Pan troglodytes

<400> SEQUENCE: 81

Cys Pro Pro Pro Met Ser Val Glu His Ala Asp Ile Trp Val Lys Ser
1               5                   10                  15

Tyr Ser Leu Tyr Ser Arg Glu Arg Tyr Ile Cys Asn Ser Gly Phe Lys
            20                  25                  30

Arg Lys Ala Gly Thr Ser Ser Leu Thr Glu Cys Val Leu Asn Lys Ala
            35                  40                  45

Thr Asn Val Ala His Trp Thr Thr Pro Ser Leu Lys Cys
    50                  55                  60

<210> SEQ ID NO 82
<211> LENGTH: 15
<212> TYPE: PRT
<213> ORGANISM: Pantroglodytes

<400> SEQUENCE: 82

Ile Arg Asp Pro Ala Leu Val Leu Gln Arg Pro Val Pro Pro Ser
1               5                   10                  15

<210> SEQ ID NO 83
<211> LENGTH: 198
<212> TYPE: PRT
<213> ORGANISM: Pan troglodytes

<400> SEQUENCE: 83

Thr Val Thr Thr Ala Gly Met Thr Pro Gln Pro Glu Ser Leu Ser Pro
1               5                   10                  15

Ser Gly Lys Gly Ser Val Ala Val Thr Met Glu Asp Thr Phe Phe Met
            20                  25                  30

Glu Arg Glu Gln His Ser Tyr Ala Thr Pro Leu Gln Cys Arg Gly Ser
            35                  40                  45

His Leu Pro Gly Lys Asp Lys Glu Asp Arg Glu Asp Ala Glu His Lys
    50                  55                  60

Ala Ala Ser Val Pro Glu Arg Lys Leu Ile Arg Thr Leu Ser Ser His
65                  70                  75                  80

Thr Ala Arg Arg Val Gln Ala Arg Ala Gln Ala Ser Arg Val Ser His
                85                  90                  95

Ala Ala Ala Pro Ser Val Leu Gly Gln Arg Ser Phe Thr Cys Ser Gln
            100                 105                 110

Leu Ser Leu Gln Gln Pro Ala Ala Ser Ser Pro Ser Ser Asn Thr Thr
            115                 120                 125

Ala Ala Thr Thr Ala Ala Ile Val Pro Gly Ser Gln Leu Met Pro Ser
        130                 135                 140

Lys Ser Pro Ser Thr Gly Thr Thr Glu Ile Gly Ser His Glu Ser Ser
145                 150                 155                 160

His Gly Thr Pro Ser Gln Thr Thr Ala Lys Thr Trp Glu Leu Thr Ala
                165                 170                 175

Ser Ala Ser His Gln Pro Pro Gly Val Tyr Pro Gln Gly His Ser Asp
            180                 185                 190

Thr Thr Val Ala Ile Ser
        195

<210> SEQ ID NO 84
<211> LENGTH: 765
<212> TYPE: PRT
<213> ORGANISM: Rattus norvegicus

<400> SEQUENCE: 84

Ala Thr Gly Gly Ala Gly Cys Ala Thr Cys Ala Cys Ala Gly Ala Gly
1               5                   10                  15

Ala Ala Thr Cys Gly Thr Gly Gly Ala Ala Ala Thr Thr Ala Thr Gly

-continued

```
            20                  25                  30

Gly Gly Gly Ala Cys Cys Cys Ala Ala Cys Ala Gly Gly Gly Ala Ala
        35                  40                  45

Gly Ala Cys Ala Thr Cys Gly Ala Gly Ala Ala Gly Gly Gly Cys Ala
    50                  55                  60

Thr Cys Ala Cys Gly Thr Gly Cys Cys Cys Ala Ala Cys Gly Cys Cys
65                  70                  75                  80

Cys Ala Thr Ala Thr Cys Thr Ala Thr Thr Gly Ala Ala Cys Ala Cys
                85                  90                  95
Gly Cys Ala Gly Ala Cys Ala Thr Cys Cys Gly Gly Gly Thr Cys Ala
            100                 105                 110
Ala Gly Ala Ala Thr Thr Ala Cys Ala Gly Thr Gly Thr Gly Ala Ala
        115                 120                 125

Cys Thr Cys Cys Ala Gly Gly Gly Ala Gly Ala Gly Gly Thr Ala Thr
    130                 135                 140

Gly Thr Cys Thr Gly Thr Ala Ala Cys Thr Cys Thr Gly Gly Cys Thr
145                 150                 155                 160
Thr Cys Ala Ala Gly Cys Gly Gly Ala Ala Ala Gly Cys Ala Gly Gly
                165                 170                 175

Cys Ala Cys Ala Thr Cys Cys Ala Cys Cys Cys Thr Gly Ala Cys Cys
            180                 185                 190

Gly Ala Gly Thr Gly Cys Gly Thr Gly Ala Thr Cys Ala Ala Thr Ala
        195                 200                 205

Ala Gly Ala Ala Cys Ala Cys Gly Ala Ala Thr Gly Thr Gly Gly Cys
    210                 215                 220

Cys Cys Ala Cys Thr Gly Gly Ala Cys Ala Ala Cys Thr Cys Cys Cys
225                 230                 235                 240

Ala Ala Cys Cys Thr Cys Ala Ala Gly Thr Gly Thr Ala Thr Cys Ala
                245                 250                 255

Ala Gly Cys Cys Ala Gly Ala Ala Gly Cys Thr Thr Thr Ala Thr Cys
            260                 265                 270

Thr Cys Cys Cys Ala Ala Ala Thr Cys Ala Gly Ala Thr Ala Cys Cys
        275                 280                 285

Ala Cys Ala Gly Thr Gly Gly Cys Cys Ala Cys Ala Gly Ala Gly Ala
    290                 295                 300

Cys Ala Gly Cys Thr Ala Thr Thr Gly Thr Gly Cys Cys Thr Gly Gly
305                 310                 315                 320

Cys Thr Cys Cys Ala Gly Gly Cys Thr Gly Ala Cys Ala Cys Cys Ala
                325                 330                 335

Thr Cys Cys Cys Ala Ala Gly Cys Ala Gly Cys Thr Thr Cys Thr Gly
            340                 345                 350

Cys Ala Gly Gly Ala Ala Cys Thr Ala Cys Ala Gly Gly Gly Ala Cys
        355                 360                 365

Gly Gly Gly Cys Ala Gly Ala Cys Ala Cys Ala Ala Gly Thr Cys Cys
    370                 375                 380

Thr Cys Cys Cys Cys Ala Gly Cys Cys Cys Cys Ala Thr Cys Thr Cys
385                 390                 395                 400

Thr Thr Gly Cys Ala Ala Cys Ala Ala Cys Ala Ala Thr Gly Ala Cys
                405                 410                 415

Cys Thr Thr Gly Gly Ala Gly Cys Cys Thr Ala Cys Ala Gly Cys Cys
            420                 425                 430

Thr Cys Cys Ala Cys Cys Thr Cys Cys Cys Thr Cys Ala Gly Gly Ala
        435                 440                 445
```

```
Thr Ala Ala Cys Ala Gly Ala Gly Ala Thr Thr Cys Thr Cys Cys
    450                 455                 460

Gly Cys Ala Cys Ala Gly Thr Thr Cys Cys Gly Ala Ala Thr Gly
465                 470                 475                 480

Ala Cys Ala Ala Ala Ala Gly Gly Thr Gly Ala Gly Thr Ala Thr
                    485                 490                 495

Thr Thr Cys Thr Thr Thr Thr Gly Thr Thr Gly Ala Thr Gly Thr
            500                 505                 510

Gly Thr Thr Thr Ala Thr Ala Ala Cys Cys Ala Gly Gly Gly Cys Ala
        515                 520                 525

Cys Thr Ala Cys Ala Ala Ala Gly Cys Ala Gly Ala Cys Cys Cys Ala
    530                 535                 540

Gly Cys Ala Thr Gly Cys Thr Cys Ala Thr Cys Ala Gly Cys Cys Thr
545                 550                 555                 560

Gly Gly Thr Cys Cys Ala Gly Gly Cys Cys Ala Cys Thr Cys Thr Ala
                565                 570                 575

Gly Cys Ala Cys Ala Gly Thr Cys Gly Cys Cys Ala Gly Cys Ala Gly
                580                 585                 590

Thr Ala Thr Gly Cys Cys Cys Thr Thr Thr Gly Cys Cys Thr Cys Gly
        595                 600                 605

Cys Cys Gly Ala Ala Ala Thr Gly Thr Cys Thr Cys Cys Gly Thr Thr
    610                 615                 620

Ala Gly Ala Gly Ala Gly Cys Ala Ala Gly Cys Thr Thr Cys Thr Cys
625                 630                 635                 640

Ala Gly Cys Cys Gly Cys Gly Thr Cys Gly Thr Cys Gly Thr Gly Ala
                645                 650                 655

Gly Gly Thr Gly Gly Ala Ala Cys Cys Ala Thr Gly Gly Ala Ala
                660                 665                 670

Ala Cys Ala Gly Thr Ala Cys Cys Ala Thr Gly Ala Cys Thr Gly
        675                 680                 685

Thr Gly Ala Gly Gly Gly Cys Cys Cys Gly Cys Ala Gly Cys Ala Ala
    690                 695                 700

Gly Gly Ala Gly Gly Ala Cys Gly Ala Ala Gly Ala Cys Cys Ala Cys
705                 710                 715                 720

Ala Cys Gly Ala Cys Thr Thr Cys Ala Gly Ala Ala Ala Cys Thr Cys
                725                 730                 735

Ala Gly Gly Gly Ala Gly Ala Cys Cys Ala Gly Cys Cys Cys Ala Cys
                740                 745                 750

Gly Cys Gly Cys Gly Gly Ala Gly Thr Cys Thr Gly Ala
        755                 760                 765

<210> SEQ ID NO 85
<211> LENGTH: 254
<212> TYPE: PRT
<213> ORGANISM: Rattus norvegicus

<400> SEQUENCE: 85

Met Glu His His Arg Glu Ser Trp Lys Leu Trp Gly Pro Asn Arg Glu
1               5                   10                  15

Asp Ile Glu Lys Gly Ile Thr Cys Pro Thr Pro Ile Ser Ile Glu His
            20                  25                  30

Ala Asp Ile Arg Val Lys Asn Tyr Ser Val Asn Ser Arg Glu Arg Tyr
        35                  40                  45

Val Cys Asn Ser Gly Phe Lys Arg Lys Ala Gly Thr Ser Thr Leu Thr
```

```
            50                  55                  60
Glu Cys Val Ile Asn Lys Asn Thr Asn Val Ala His Trp Thr Thr Pro
 65                  70                  75                  80

Asn Leu Lys Cys Ile Lys Pro Glu Ala Leu Ser Pro Lys Ser Asp Thr
                 85                  90                  95

Thr Val Ala Thr Glu Thr Ala Ile Val Pro Gly Ser Arg Leu Thr Pro
                100                 105                 110

Ser Gln Ala Ala Ser Ala Gly Thr Thr Gly Thr Gly Arg His Lys Ser
                115                 120                 125

Ser Pro Ala Pro Ser Leu Ala Thr Thr Met Thr Leu Glu Pro Thr Ala
            130                 135                 140

Ser Thr Ser Leu Arg Ile Thr Glu Ile Ser Pro His Ser Ser Glu Met
145                 150                 155                 160

Thr Lys Gly Glu Tyr Phe Leu Leu Phe Asp Val Phe Ile Thr Arg Ala
                165                 170                 175

Leu Gln Ser Arg Pro Ser Met Leu Ile Ser Leu Val Gln Ala Thr Leu
                180                 185                 190

Ala Gln Ser Pro Ala Val Cys Pro Leu Pro Arg Arg Asn Val Ser Val
            195                 200                 205

Arg Glu Gln Ala Ser Gln Pro Arg Arg Val Glu Val Glu Thr Met Glu
210                 215                 220

Thr Val Pro Met Thr Val Arg Ala Arg Ser Lys Glu Asp Glu Asp His
225                 230                 235                 240

Thr Thr Ser Glu Thr Gln Gly Asp Gln Pro Thr Arg Gly Val
                245                 250
```

<210> SEQ ID NO 86
<211> LENGTH: 182
<212> TYPE: PRT
<213> ORGANISM: Rattus norvegicus

<400> SEQUENCE: 86

```
Met Glu His His Arg Glu Ser Trp Lys Leu Trp Gly Pro Asn Arg Glu
  1               5                  10                  15

Asp Ile Glu Lys Gly Ile Thr Cys Pro Thr Pro Ile Ser Ile Glu His
                 20                  25                  30

Ala Asp Ile Arg Val Lys Asn Tyr Ser Val Asn Ser Arg Glu Arg Tyr
             35                  40                  45

Val Cys Asn Ser Gly Phe Lys Arg Lys Ala Gly Thr Ser Thr Leu Thr
 50                  55                  60

Glu Cys Val Ile Asn Lys Asn Thr Asn Val Ala His Trp Thr Thr Pro
 65                  70                  75                  80

Asn Leu Lys Cys Ile Lys Pro Glu Ala Leu Ser Pro Lys Ser Asp Thr
                 85                  90                  95

Thr Val Ala Thr Glu Thr Ala Ile Val Pro Gly Ser Arg Leu Thr Pro
                100                 105                 110

Ser Gln Ala Ala Ser Ala Gly Thr Thr Gly Thr Gly Arg His Lys Ser
                115                 120                 125

Ser Pro Ala Pro Ser Leu Ala Thr Thr Met Thr Leu Glu Pro Thr Ala
            130                 135                 140

Ser Thr Ser Leu Arg Ile Thr Glu Ile Ser Pro His Ser Ser Glu Met
145                 150                 155                 160

Thr Lys Gly Glu Tyr Phe Leu Leu Phe Asp Val Phe Ile Thr Arg Ala
                165                 170                 175
```

Leu Gln Ser Arg Pro Ser
          180

<210> SEQ ID NO 87
<211> LENGTH: 61
<212> TYPE: PRT
<213> ORGANISM: Rattus norvegicus

<400> SEQUENCE: 87

Cys Pro Thr Pro Ile Ser Ile Glu His Ala Asp Ile Arg Val Lys Asn
1               5                   10                  15

Tyr Ser Val Asn Ser Arg Glu Arg Tyr Val Cys Asn Ser Gly Phe Lys
            20                  25                  30

Arg Lys Ala Gly Thr Ser Thr Leu Thr Glu Cys Val Ile Asn Lys Asn
        35                  40                  45

Thr Asn Val Ala His Trp Thr Thr Pro Asn Leu Lys Cys
    50                  55                  60

<210> SEQ ID NO 88
<211> LENGTH: 12
<212> TYPE: PRT
<213> ORGANISM: Rattus norvegicus

<400> SEQUENCE: 88

Ile Lys Pro Glu Ala Leu Ser Pro Lys Ser Asp Thr
1               5                   10

<210> SEQ ID NO 89
<211> LENGTH: 86
<212> TYPE: PRT
<213> ORGANISM: Rattus norvegicus

<400> SEQUENCE: 89

Thr Val Ala Thr Glu Thr Ala Ile Val Pro Gly Ser Arg Leu Thr Pro
1               5                   10                  15

Ser Gln Ala Ala Ser Ala Gly Thr Thr Gly Thr Gly Arg His Lys Ser
            20                  25                  30

Ser Pro Ala Pro Ser Leu Ala Thr Thr Met Thr Leu Glu Pro Thr Ala
        35                  40                  45

Ser Thr Ser Leu Arg Ile Thr Glu Ile Ser Pro His Ser Ser Glu Met
    50                  55                  60

Thr Lys Gly Glu Tyr Phe Leu Leu Phe Asp Val Phe Ile Thr Arg Ala
65                  70                  75                  80

Leu Gln Ser Arg Pro Ser
            85

<210> SEQ ID NO 90
<211> LENGTH: 93
<212> TYPE: DNA
<213> ORGANISM: Mus musculus

<400> SEQUENCE: 90
gagacccctc cctagctcac tacagtccag tgccaacagt agtgacacca aaggtgacct    60
cacagccaga gagcccctcc ccctctgcaa aag                                93

<210> SEQ ID NO 91
<211> LENGTH: 99
<212> TYPE: DNA
<213> ORGANISM: Pan troglodytes

<400> SEQUENCE: 91

```
gagaccctgc cctggttctc caaaggccag tgccaccctc acagtaacg acggcaggga      60 tgacccaca gccagagagc ctctcccctt ctggaaaag                              99
```

<210> SEQ ID NO 92
<211> LENGTH: 198
<212> TYPE: DNA
<213> ORGANISM: Rattus norvegicus

<400> SEQUENCE: 92

```
agccagaagc tttatctccc aaatcagata ccacagtggc cacagagaca gctattgtgc      60
ctggctccag gctgacacca tcccaagcag cttctgcagg aactacaggg acgggcagac     120
acaagtcctc cccagcccca tctcttgcaa caacaatgac cttggagcct acagcctcca    180
cctccctcag gataacag                                                   198
```

<210> SEQ ID NO 93
<211> LENGTH: 33
<212> TYPE: PRT
<213> ORGANISM: Homo sapiens

<400> SEQUENCE: 93

```
Arg Asp Pro Ala Leu Val His Gln Arg Pro Ala Pro Ser Thr Val
1               5                   10                  15

Thr Thr Ala Gly Val Thr Pro Gln Pro Glu Ser Leu Ser Pro Ser Gly
            20                  25                  30

Lys
```

<210> SEQ ID NO 94
<211> LENGTH: 31
<212> TYPE: PRT
<213> ORGANISM: Mus musculus

<400> SEQUENCE: 94

```
Arg Asp Pro Ser Leu Ala His Tyr Ser Pro Val Pro Thr Val Val Thr
1               5                   10                  15

Pro Lys Val Thr Ser Gln Pro Glu Ser Pro Ser Pro Ser Ala Lys
            20                  25                  30
```

<210> SEQ ID NO 95
<211> LENGTH: 33
<212> TYPE: PRT
<213> ORGANISM: Pan troglodytes

<400> SEQUENCE: 95

```
Arg Asp Pro Ala Leu Val Leu Gln Arg Pro Val Pro Ser Thr Val
1               5                   10                  15

Thr Thr Ala Gly Met Thr Pro Gln Pro Glu Ser Leu Ser Pro Ser Gly
            20                  25                  30

Lys
```

<210> SEQ ID NO 96
<211> LENGTH: 66
<212> TYPE: PRT
<213> ORGANISM: Rattus norvegicus

<400> SEQUENCE: 96

```
Lys Pro Glu Ala Leu Ser Pro Lys Ser Asp Thr Thr Val Ala Thr Glu
1               5                   10                  15

Thr Ala Ile Val Pro Gly Ser Arg Leu Thr Pro Ser Gln Ala Ala Ser
```

-continued

```
                    20                  25                  30

Ala Gly Thr Thr Gly Thr Gly Arg His Lys Ser Ser Pro Ala Pro Ser
                35                  40                  45

Leu Ala Thr Thr Met Thr Leu Glu Pro Thr Ala Ser Thr Ser Leu Arg
    50                  55                  60

Ile Thr
65
```

<210> SEQ ID NO 97
<211> LENGTH: 65
<212> TYPE: PRT
<213> ORGANISM: Mus musculus

<400> SEQUENCE: 97

```
Gly Thr Thr Cys Pro Pro Val Ser Ile Glu His Ala Asp Ile Arg
1               5                   10                  15

Val Lys Asn Tyr Ser Val Asn Ser Arg Glu Arg Tyr Val Cys Asn Ser
                20                  25                  30

Gly Phe Lys Arg Lys Ala Gly Thr Ser Thr Leu Ile Glu Cys Val Ile
                35                  40                  45

Asn Lys Asn Thr Asn Val Ala His Trp Thr Pro Ser Leu Lys Cys
    50                  55                  60

Ile
65
```

<210> SEQ ID NO 98
<211> LENGTH: 65
<212> TYPE: PRT
<213> ORGANISM: Pan troglodytes

<400> SEQUENCE: 98

```
Gly Ile Thr Cys Pro Pro Met Ser Val Glu His Ala Asp Ile Trp
1               5                   10                  15

Val Lys Ser Tyr Ser Leu Tyr Ser Arg Glu Arg Tyr Ile Cys Asn Ser
                20                  25                  30

Gly Phe Lys Arg Lys Ala Gly Thr Ser Ser Leu Thr Glu Cys Val Leu
                35                  40                  45

Asn Lys Ala Thr Asn Val Ala His Trp Thr Pro Ser Leu Lys Cys
    50                  55                  60

Ile
65
```

<210> SEQ ID NO 99
<211> LENGTH: 65
<212> TYPE: PRT
<213> ORGANISM: Rattus norvegicus

<400> SEQUENCE: 99

```
Gly Ile Thr Cys Pro Thr Pro Ile Ser Ile Glu His Ala Asp Ile Arg
1               5                   10                  15

Val Lys Asn Tyr Ser Val Asn Ser Arg Glu Arg Tyr Val Cys Asn Ser
                20                  25                  30

Gly Phe Lys Arg Lys Ala Gly Thr Ser Thr Leu Thr Glu Cys Val Ile
                35                  40                  45

Asn Lys Asn Thr Asn Val Ala His Trp Thr Pro Asn Leu Lys Cys
    50                  55                  60

Ile
65
```

```
<210> SEQ ID NO 100
<211> LENGTH: 20
<212> TYPE: DNA
<213> ORGANISM: Artificial
<220> FEATURE:
<223> OTHER INFORMATION: Sense primer for gamma chain

<400> SEQUENCE: 100
gaagagcaag cgccatgttg                                               20

<210> SEQ ID NO 101
<211> LENGTH: 20
<212> TYPE: DNA
<213> ORGANISM: Artificial
<220> FEATURE:
<223> OTHER INFORMATION: Antisense primer for gamma chain

<400> SEQUENCE: 101
tcaggtttca ggctttaggg                                               20
```